US010675264B2

(12) United States Patent
Green et al.

(10) Patent No.: US 10,675,264 B2
(45) Date of Patent: Jun. 9, 2020

(54) TERPENE-BASED COMPOSITIONS, METHODS OF PREPARATIONS AND USES THEREOF

(71) Applicant: ELEVATE TECHNOLOGIES LLC, San Juan, PR (US)

(72) Inventors: Wayne Green, Encinitas, CA (US); Shea Alderete, San Clemente, CA (US); Justin Freyre, Encinitas, CA (US)

(73) Assignee: Elevate Technologies LLC, San Juan, PR (US)

(*) Notice: Subject to any disclaimer, the term of this patent is extended or adjusted under 35 U.S.C. 154(b) by 0 days.

(21) Appl. No.: 15/889,112

(22) Filed: Feb. 5, 2018

(65) Prior Publication Data

US 2018/0369192 A1 Dec. 27, 2018

Related U.S. Application Data

(60) Provisional application No. 62/456,047, filed on Feb. 7, 2017.

(51) Int. Cl.

| | |
|---|---|
| ***A61K 36/185*** | (2006.01) |
| ***A61K 31/352*** | (2006.01) |
| ***C12Q 1/6895*** | (2018.01) |
| ***A61K 31/01*** | (2006.01) |
| ***A61K 31/015*** | (2006.01) |
| ***A61P 25/00*** | (2006.01) |

(Continued)

(52) U.S. Cl.

CPC ............ *A61K 31/352* (2013.01); *A61K 31/01* (2013.01); *A61K 31/015* (2013.01); *A61K 31/045* (2013.01); *A61K 31/192* (2013.01); *A61K 36/185* (2013.01); *A61P 25/00* (2018.01); *C11B 9/00* (2013.01); *C12Q 1/6827* (2013.01); *C12Q 1/6895* (2013.01); *C12Q 2600/156* (2013.01)

(58) Field of Classification Search

CPC .................................................. A61K 36/185

See application file for complete search history.

(56) References Cited

U.S. PATENT DOCUMENTS

2006/0222723 A1 10/2006 Bevilacqua
2014/0271940 A1 9/2014 Wurzer

FOREIGN PATENT DOCUMENTS

WO WO 2016-103254 A1 6/2016
WO WO 2016-123160 A1 8/2016
WO WO 2016-199148 A1 12/2016

OTHER PUBLICATIONS

International Search Report and Written Opinion for PCT/US2018/016913 dated Jun. 8, 2018.

(Continued)

*Primary Examiner* — Rosanne Kosson

(74) *Attorney, Agent, or Firm* — Knobbe, Martens, Olson & Bear, LLP

(57) ABSTRACT

The present disclosure generally relates to terpene-based compositions for applications in the pharmaceutical and recreational fields. In some embodiments, the compositions are enriched compositions or non-naturally occurring compositions which contain defined concentrations of one or more cannabis-derived chemical compounds, such as terpenes and cannabinoids that have a distinctive characteristic that mimics that of a cannabis plant matter or a product thereof. Also provided in some embodiments of the disclosure are methods for the preparation of the compositions, as well as methods for use thereof.

15 Claims, 12 Drawing Sheets

Specification includes a Sequence Listing.

"JetFuel" Strain - Terpene Profile

(51) Int. Cl.

| | |
|---|---|
| ***A61K 31/192*** | (2006.01) |
| ***A61K 31/045*** | (2006.01) |
| ***C11B 9/00*** | (2006.01) |
| ***C12Q 1/6827*** | (2018.01) |

(56) References Cited

OTHER PUBLICATIONS

Andrea et al. J. Agric. Food Chem. 51:4978-4983, 2003.
Dagulo et al. J. Food Sci. 75:C199-207, 2010.
Diego et al. (1998) Int. J. Neurosci. 96:217-224.
El-Alfy et al., 2010, Pharmacology Biochemistry and Behavior 95 (4): 434-42).
Hendriks and Bruins, Biol. Mass Spectrom. 10:377-381, 1983.
Neuberger et al., Neuropsychopharmacology. 29:1925-1932, 2004.
Jella et al. J. Agric. Food Chem. 46:242-247, 1998.
Knasko (1992) Chem. Senses. 17;27-35.
Mucci et al., Food Chem. 141:3167-3176, 2013.
Musenga et al. J. Sep. Sci. 29:1251-1258, 2006.
Reineccius TA et al. Journal of Food Science, 68(4), 1234-1239, 2003.
Rubiano et al., Ing. Compet. vol. 17 No. 2 Cali 2015.
Satoh and Sugawara, Analytical Sciences. 19:139-146, 2003.
Scalarone et al., J. Mass Spectrom. 40:1527-1535, 2005.
Sugawara et al. J. Home Econ. Jpn. 49:1281-1290, 1998.
Sugawara et al. Molecules. 18:3312-3338, 2013.
Trofin, I. G. et al., "Identification and Characterization of Special Types of Herbal Cannabis", U.P.B. Sci. Bull., Series B, vol. 74, Iss. 1, 2012, pp. 119-130.
Villa et al. J. Pharm. Biomed. Anal. 44:755-762, 2007.
Yamamoto et al., Molecular encapsulation of citral or d-limonene flavor by spray drying.
Yang et al. J. Nat. Prod. 72:484-487, 2009.
Zhang et al., Food Chem. 138:208-213, 2013.

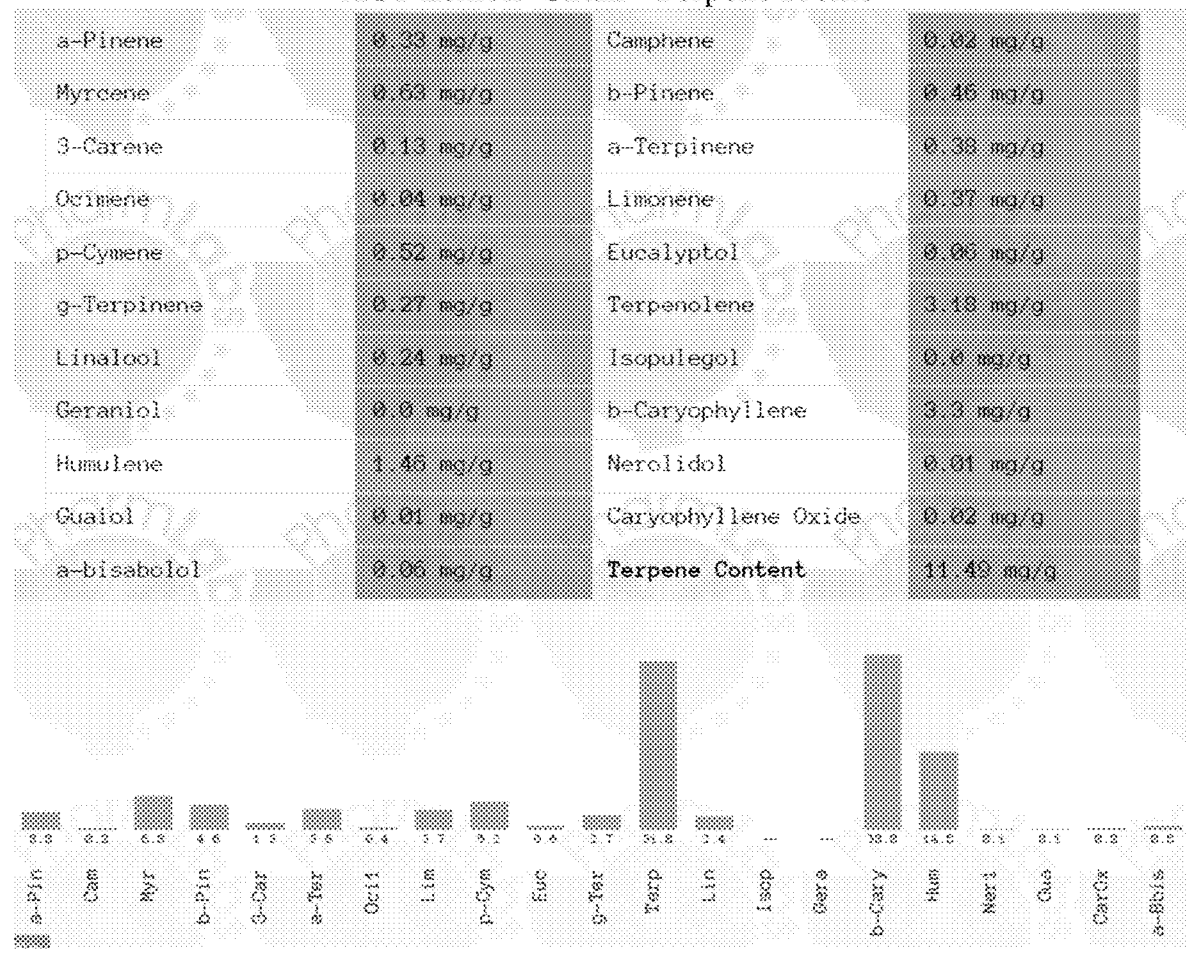

"AG1 Lemon" Strain - Terpene Profile

| | | | |
|---|---|---|---|
| a-Pinene | 0.33 mg/g | Camphene | 0.02 mg/g |
| Myrcene | 0.63 mg/g | b-Pinene | 0.46 mg/g |
| 3-Carene | 0.13 mg/g | a-Terpinene | 0.38 mg/g |
| Ocimene | 0.04 mg/g | Limonene | 0.37 mg/g |
| p-Cymene | 0.52 mg/g | Eucalyptol | 0.06 mg/g |
| g-Terpinene | 0.27 mg/g | Terpenolene | 3.18 mg/g |
| Linalool | 0.24 mg/g | Isopulegol | 0.0 mg/g |
| Geraniol | 0.0 mg/g | b-Caryophyllene | 3.3 mg/g |
| Humulene | 1.46 mg/g | Nerolidol | 0.01 mg/g |
| Guaiol | 0.01 mg/g | Caryophyllene Oxide | 0.02 mg/g |
| a-bisabolol | 0.06 mg/g | **Terpene Content** | 11.49 mg/g |

*FIG. 1*

“AG2 Orange” Strain - Terpene Profile

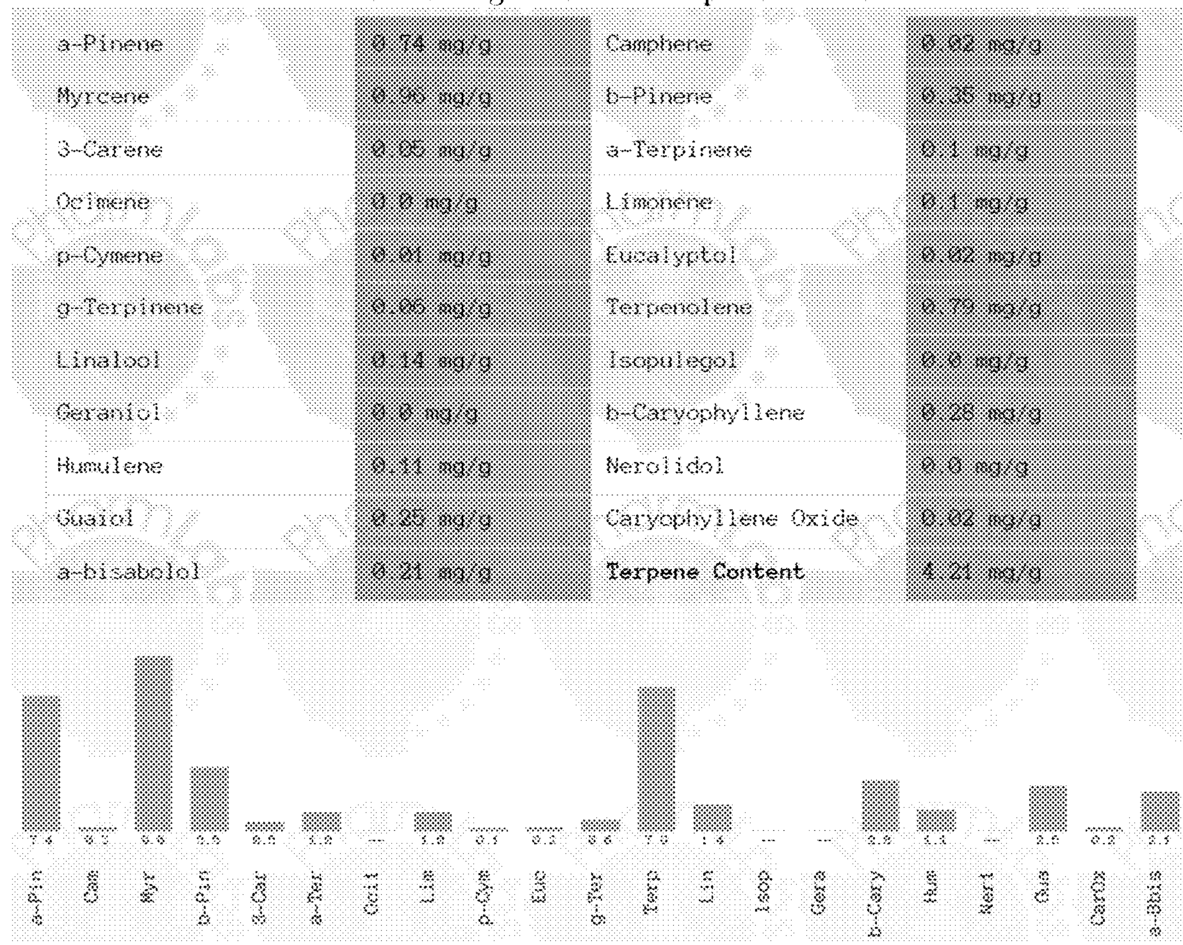

| | | | |
|---|---|---|---|
| a-Pinene | 0.74 mg/g | Camphene | 0.02 mg/g |
| Myrcene | 0.96 mg/g | b-Pinene | 0.35 mg/g |
| 3-Carene | 0.05 mg/g | a-Terpinene | 0.1 mg/g |
| Ocimene | 0.0 mg/g | Limonene | 0.1 mg/g |
| p-Cymene | 0.01 mg/g | Eucalyptol | 0.02 mg/g |
| g-Terpinene | 0.06 mg/g | Terpenolene | 0.79 mg/g |
| Linalool | 0.14 mg/g | Isopulegol | 0.0 mg/g |
| Geraniol | 0.0 mg/g | b-Caryophyllene | 0.28 mg/g |
| Humulene | 0.11 mg/g | Nerolidol | 0.0 mg/g |
| Guaiol | 0.25 mg/g | Caryophyllene Oxide | 0.02 mg/g |
| a-bisabolol | 0.21 mg/g | **Terpene Content** | 4.21 mg/g |

*FIG. 2*

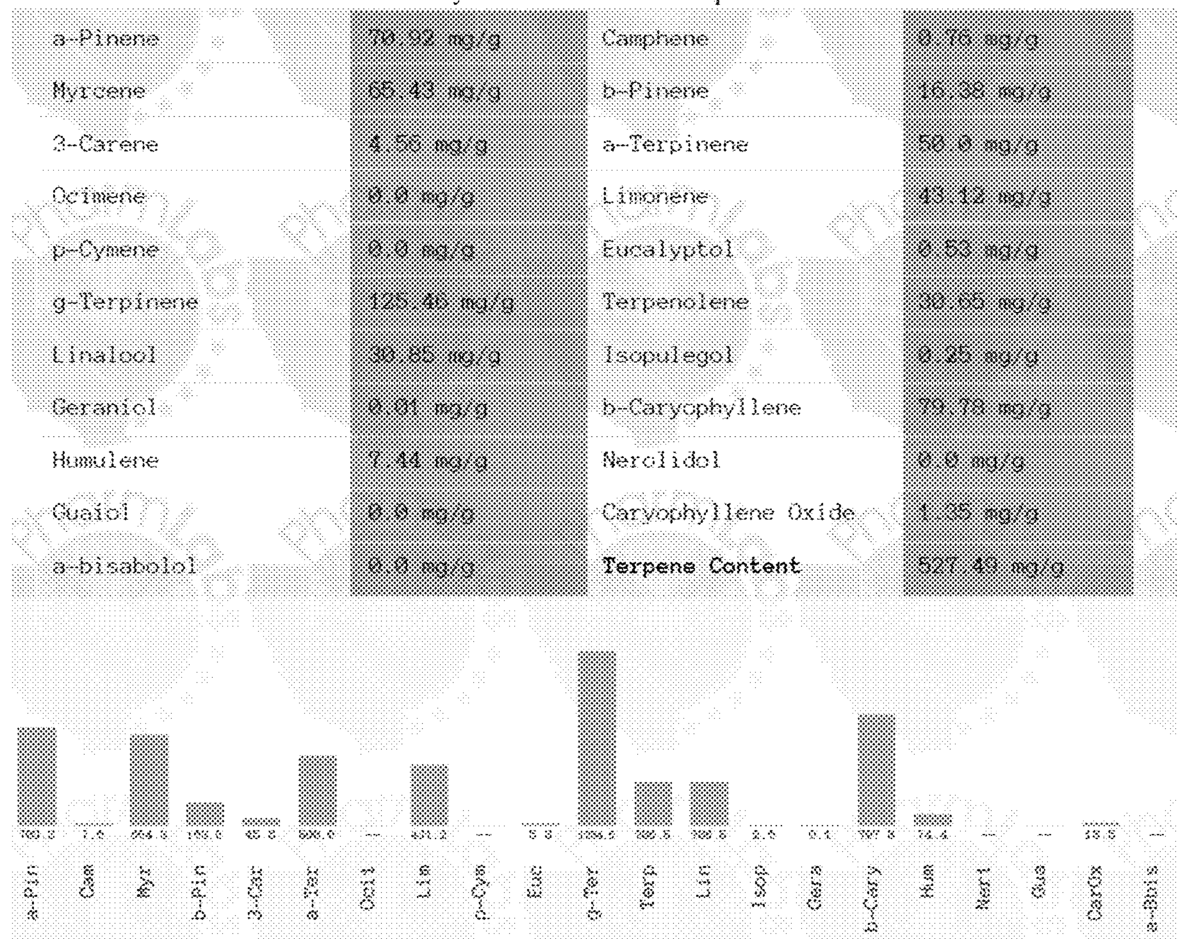

"Blueberry OG" Strain - Terpene Profile

| | | | |
|---|---|---|---|
| a-Pinene | 70.92 mg/g | Camphene | 0.76 mg/g |
| Myrcene | 65.43 mg/g | b-Pinene | 16.38 mg/g |
| 3-Carene | 4.56 mg/g | a-Terpinene | 50.0 mg/g |
| Ocimene | 0.0 mg/g | Limonene | 43.12 mg/g |
| p-Cymene | 0.0 mg/g | Eucalyptol | 0.53 mg/g |
| g-Terpinene | 125.46 mg/g | Terpenolene | 30.65 mg/g |
| Linalool | 30.85 mg/g | Isopulegol | 0.25 mg/g |
| Geraniol | 0.01 mg/g | b-Caryophyllene | 79.78 mg/g |
| Humulene | 7.44 mg/g | Nerolidol | 0.0 mg/g |
| Guaiol | 0.0 mg/g | Caryophyllene Oxide | 1.35 mg/g |
| a-bisabolol | 0.0 mg/g | **Terpene Content** | 527.49 mg/g |

*FIG. 3*

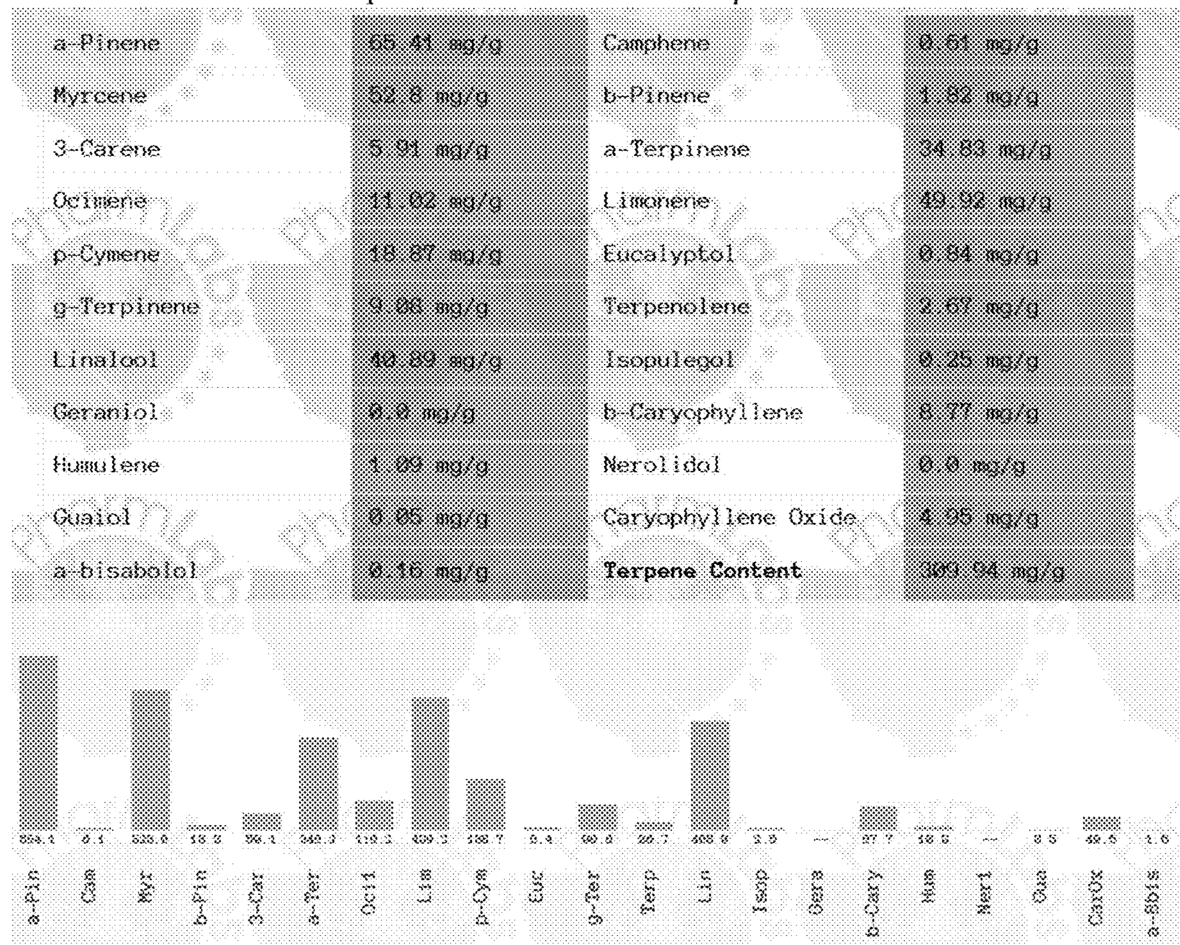

"Keep Tahoe OG" Strain - Terpene Profile

| Terpene | Content | Terpene | Content |
|---|---|---|---|
| a-Pinene | 65.41 mg/g | Camphene | 0.61 mg/g |
| Myrcene | 52.8 mg/g | b-Pinene | 1.82 mg/g |
| 3-Carene | 5.91 mg/g | a-Terpinene | 34.83 mg/g |
| Ocimene | 11.02 mg/g | Limonene | 49.92 mg/g |
| p-Cymene | 18.87 mg/g | Eucalyptol | 0.84 mg/g |
| g-Terpinene | 9.08 mg/g | Terpenolene | 2.67 mg/g |
| Linalool | 40.89 mg/g | Isopulegol | 0.25 mg/g |
| Geraniol | 0.0 mg/g | b-Caryophyllene | 8.77 mg/g |
| Humulene | 1.09 mg/g | Nerolidol | 0.0 mg/g |
| Guaiol | 0.05 mg/g | Caryophyllene Oxide | 4.95 mg/g |
| a-bisabolol | 0.16 mg/g | **Terpene Content** | 309.94 mg/g |

*FIG. 4*

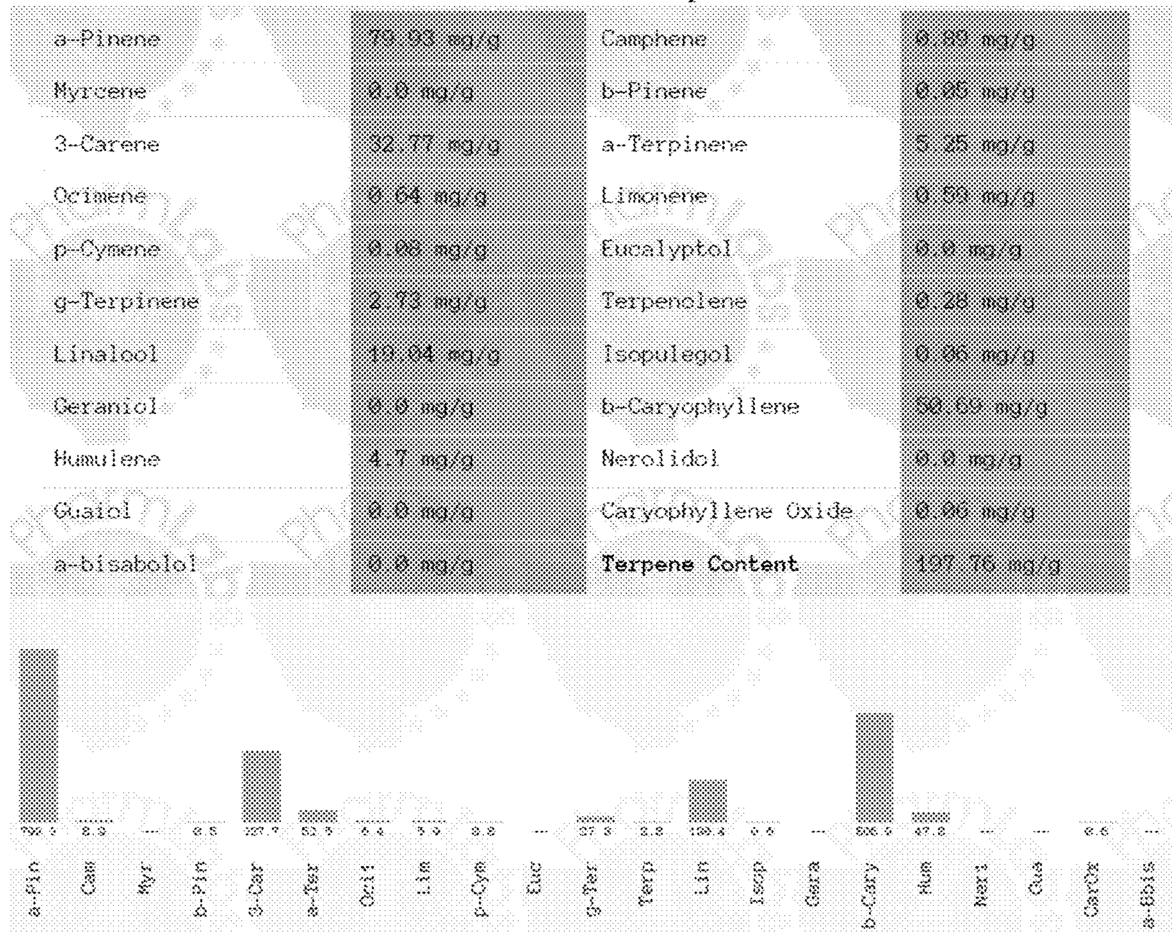

"ACDC PX" Strain - Terpene Profile

| | | | |
|---|---|---|---|
| a-Pinene | 79.93 mg/g | Camphene | 0.89 mg/g |
| Myrcene | 0.0 mg/g | b-Pinene | 0.05 mg/g |
| 3-Carene | 32.77 mg/g | a-Terpinene | 5.25 mg/g |
| Ocimene | 0.64 mg/g | Limonene | 0.59 mg/g |
| p-Cymene | 0.08 mg/g | Eucalyptol | 0.0 mg/g |
| g-Terpinene | 2.73 mg/g | Terpenolene | 0.28 mg/g |
| Linalool | 19.04 mg/g | Isopulegol | 0.06 mg/g |
| Geraniol | 0.0 mg/g | b-Caryophyllene | 50.69 mg/g |
| Humulene | 4.7 mg/g | Nerolidol | 0.0 mg/g |
| Guaiol | 0.0 mg/g | Caryophyllene Oxide | 0.06 mg/g |
| a-bisabolol | 0.0 mg/g | **Terpene Content** | 197.76 mg/g |

*FIG. 5*

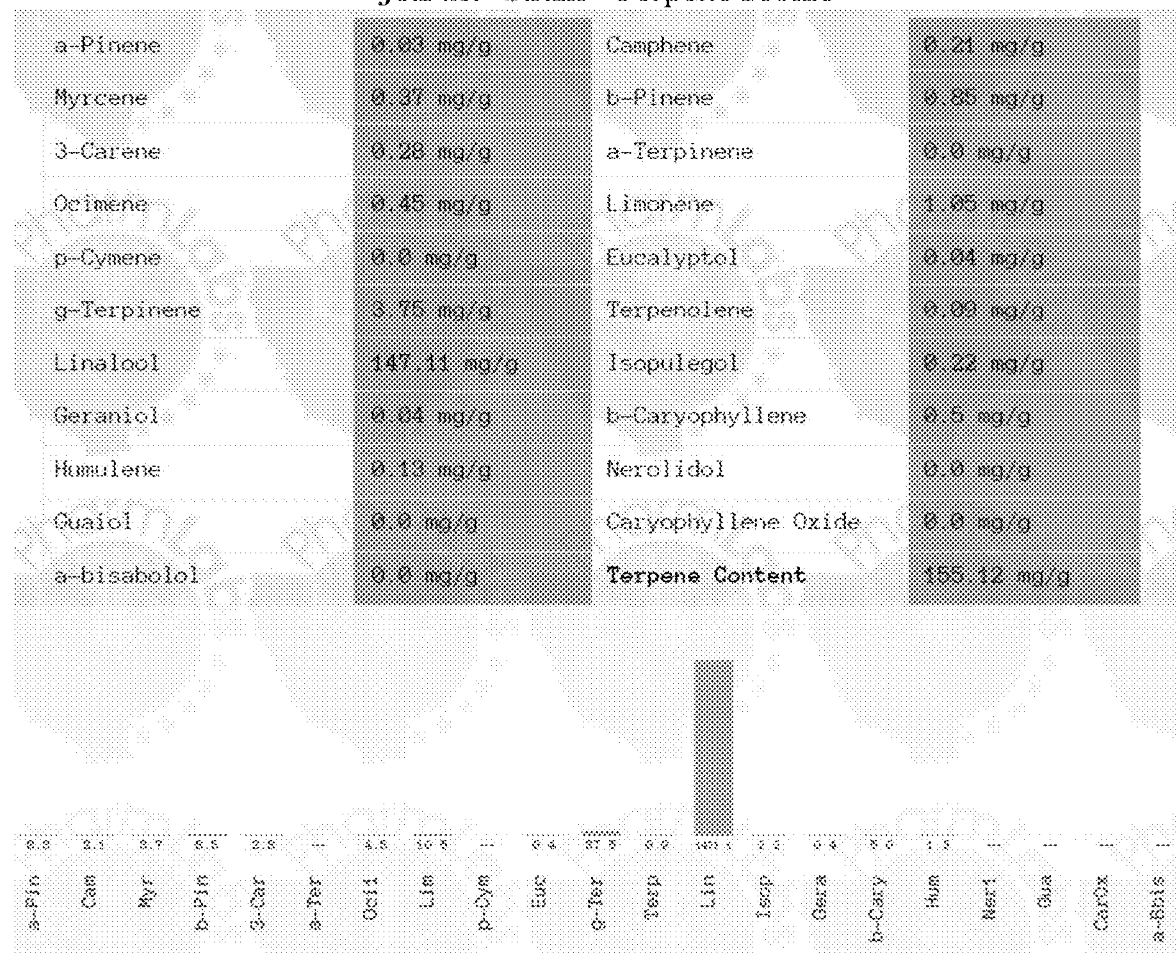

"JetFuel" Strain - Terpene Profile

| | | | |
|---|---|---|---|
| a-Pinene | 0.03 mg/g | Camphene | 0.21 mg/g |
| Myrcene | 0.37 mg/g | b-Pinene | 0.85 mg/g |
| 3-Carene | 0.28 mg/g | a-Terpinene | 0.0 mg/g |
| Ocimene | 0.45 mg/g | Limonene | 1.05 mg/g |
| p-Cymene | 0.0 mg/g | Eucalyptol | 0.04 mg/g |
| g-Terpinene | 3.75 mg/g | Terpenolene | 0.09 mg/g |
| Linalool | 147.11 mg/g | Isopulegol | 0.22 mg/g |
| Geraniol | 0.04 mg/g | b-Caryophyllene | 0.5 mg/g |
| Humulene | 0.13 mg/g | Nerolidol | 0.0 mg/g |
| Guaiol | 0.0 mg/g | Caryophyllene Oxide | 0.0 mg/g |
| a-bisabolol | 0.0 mg/g | **Terpene Content** | 155.12 mg/g |

*FIG. 6*

"Watermelon OG" Strain - Terpene Profile

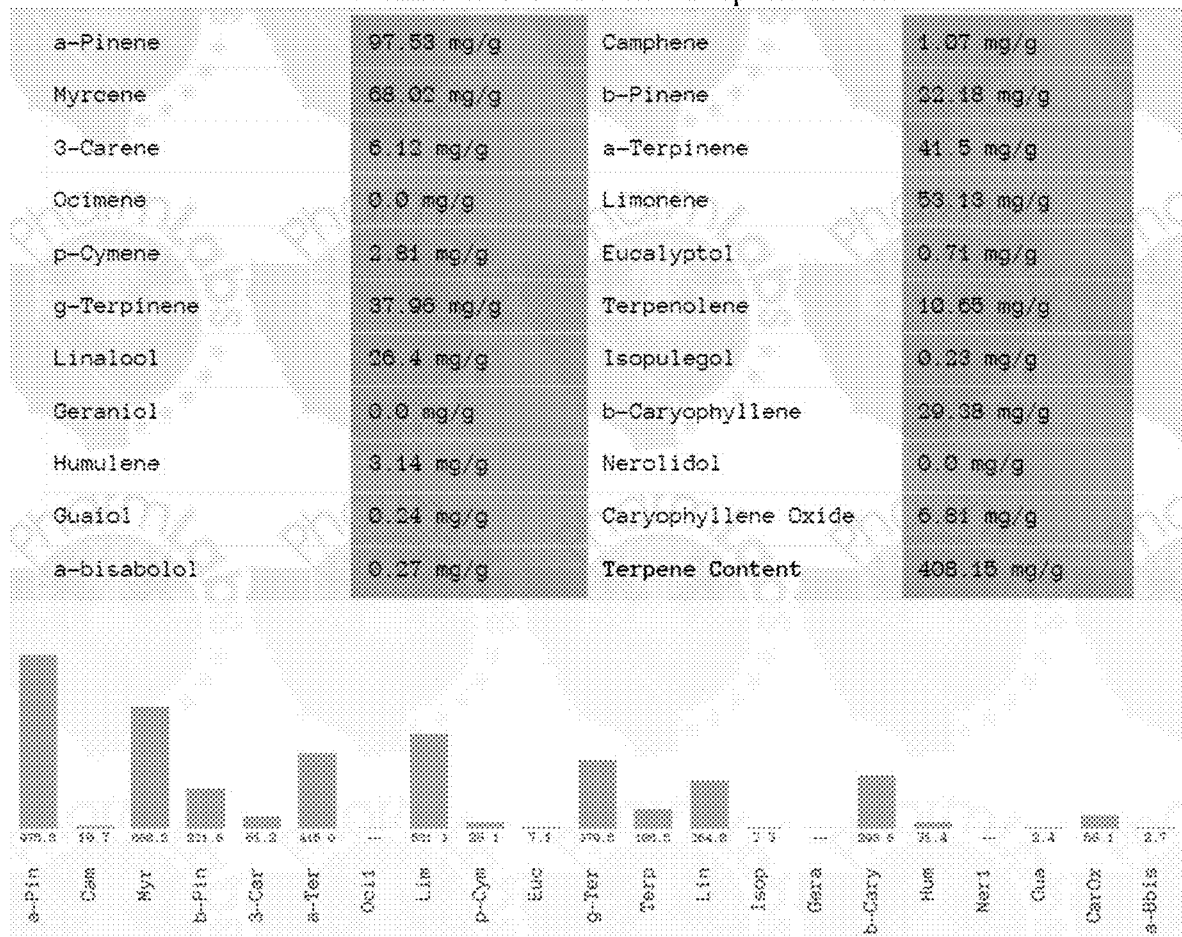

| | | | |
|---|---|---|---|
| a-Pinene | 97.53 mg/g | Camphene | 1.07 mg/g |
| Myrcene | 68.02 mg/g | b-Pinene | 22.18 mg/g |
| 3-Carene | 6.13 mg/g | a-Terpinene | 41.5 mg/g |
| Ocimene | 0.0 mg/g | Limonene | 53.13 mg/g |
| p-Cymene | 2.81 mg/g | Eucalyptol | 0.71 mg/g |
| g-Terpinene | 37.96 mg/g | Terpenolene | 10.65 mg/g |
| Linalool | 28.4 mg/g | Isopulegol | 0.23 mg/g |
| Geraniol | 0.0 mg/g | b-Caryophyllene | 29.38 mg/g |
| Humulene | 3.14 mg/g | Nerolidol | 0.0 mg/g |
| Guaiol | 0.24 mg/g | Caryophyllene Oxide | 6.81 mg/g |
| a-bisabolol | 0.27 mg/g | Terpene Content | 408.15 mg/g |

*FIG. 7*

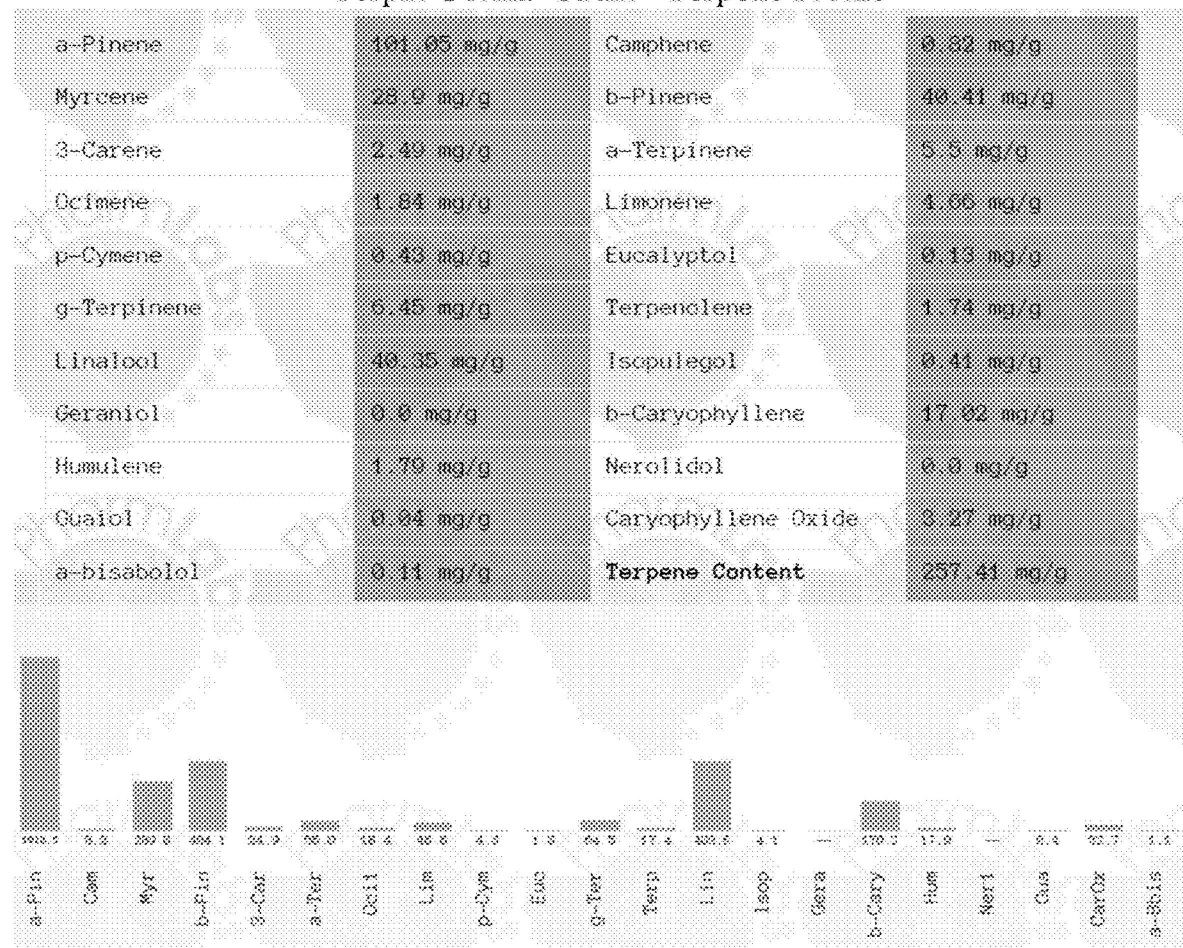

"Terpin Gorilla" Strain - Terpene Profile

| | | | |
|---|---|---|---|
| a-Pinene | 101.05 mg/g | Camphene | 0.32 mg/g |
| Myrcene | 28.9 mg/g | b-Pinene | 40.41 mg/g |
| 3-Carene | 2.49 mg/g | a-Terpinene | 5.5 mg/g |
| Ocimene | 1.84 mg/g | Limonene | 4.06 mg/g |
| p-Cymene | 0.43 mg/g | Eucalyptol | 0.13 mg/g |
| g-Terpinene | 6.45 mg/g | Terpenolene | 1.74 mg/g |
| Linalool | 40.35 mg/g | Iscpulegol | 0.41 mg/g |
| Geraniol | 0.0 mg/g | b-Caryophyllene | 17.02 mg/g |
| Humulene | 1.79 mg/g | Nerolidol | 0.0 mg/g |
| Guaiol | 0.04 mg/g | Caryophyllene Oxide | 3.27 mg/g |
| a-bisabolol | 0.11 mg/g | **Terpene Content** | 257.41 mg/g |

*FIG. 8*

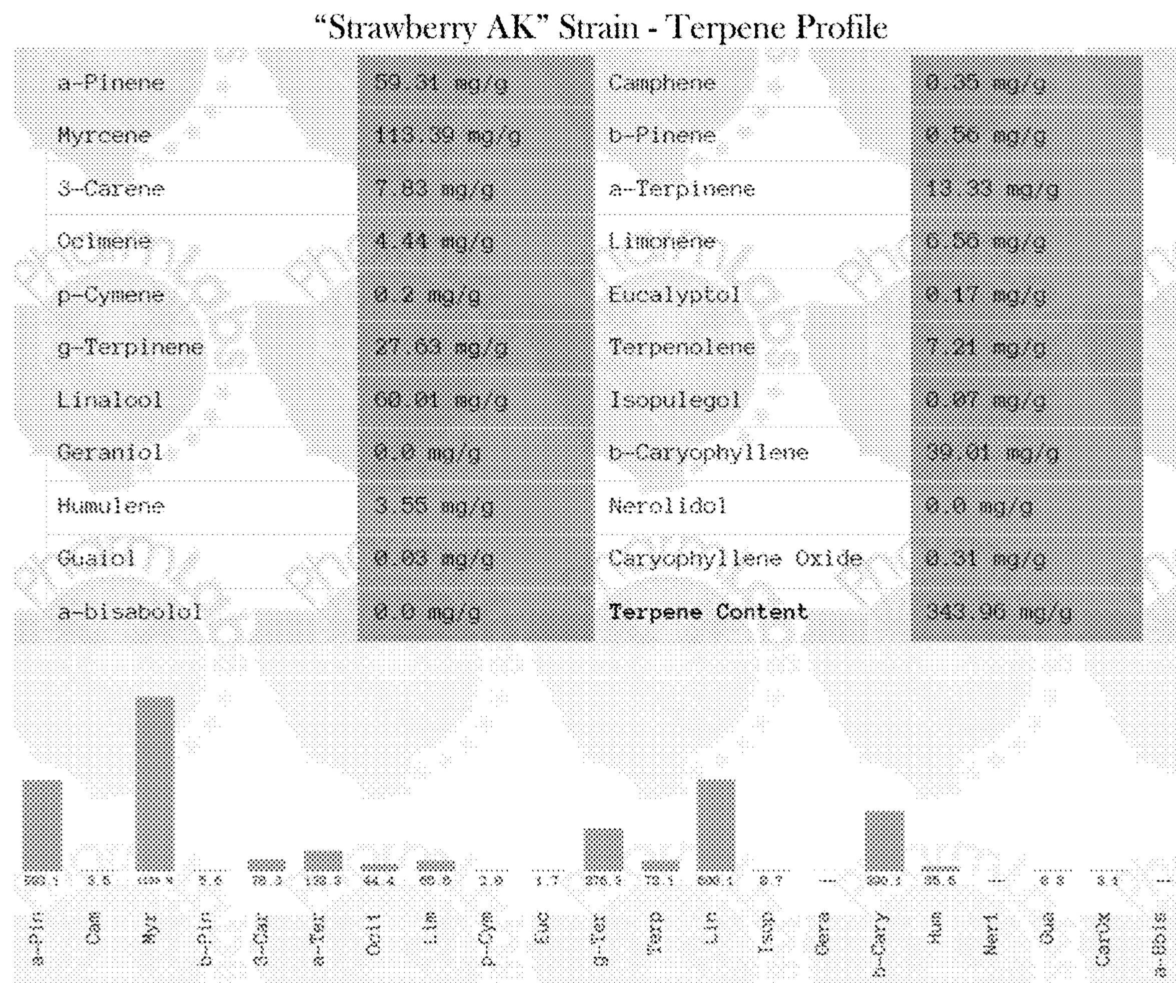

"Strawberry AK" Strain - Terpene Profile

| | | | |
|---|---|---|---|
| a-Pinene | 59.31 mg/g | Camphene | 0.35 mg/g |
| Myrcene | 113.39 mg/g | b-Pinene | 0.56 mg/g |
| 3-Carene | 7.83 mg/g | a-Terpinene | 13.33 mg/g |
| Ocimene | 4.44 mg/g | Limonene | 6.56 mg/g |
| p-Cymene | 0.2 mg/g | Eucalyptol | 0.17 mg/g |
| g-Terpinene | 27.63 mg/g | Terpenolene | 7.21 mg/g |
| Linalool | 60.01 mg/g | Isopulegol | 0.07 mg/g |
| Geraniol | 0.0 mg/g | b-Caryophyllene | 39.01 mg/g |
| Humulene | 3.55 mg/g | Nerolidol | 0.0 mg/g |
| Guaiol | 0.03 mg/g | Caryophyllene Oxide | 0.31 mg/g |
| a-bisabolol | 0.0 mg/g | **Terpene Content** | 343.96 mg/g |

*FIG. 9*

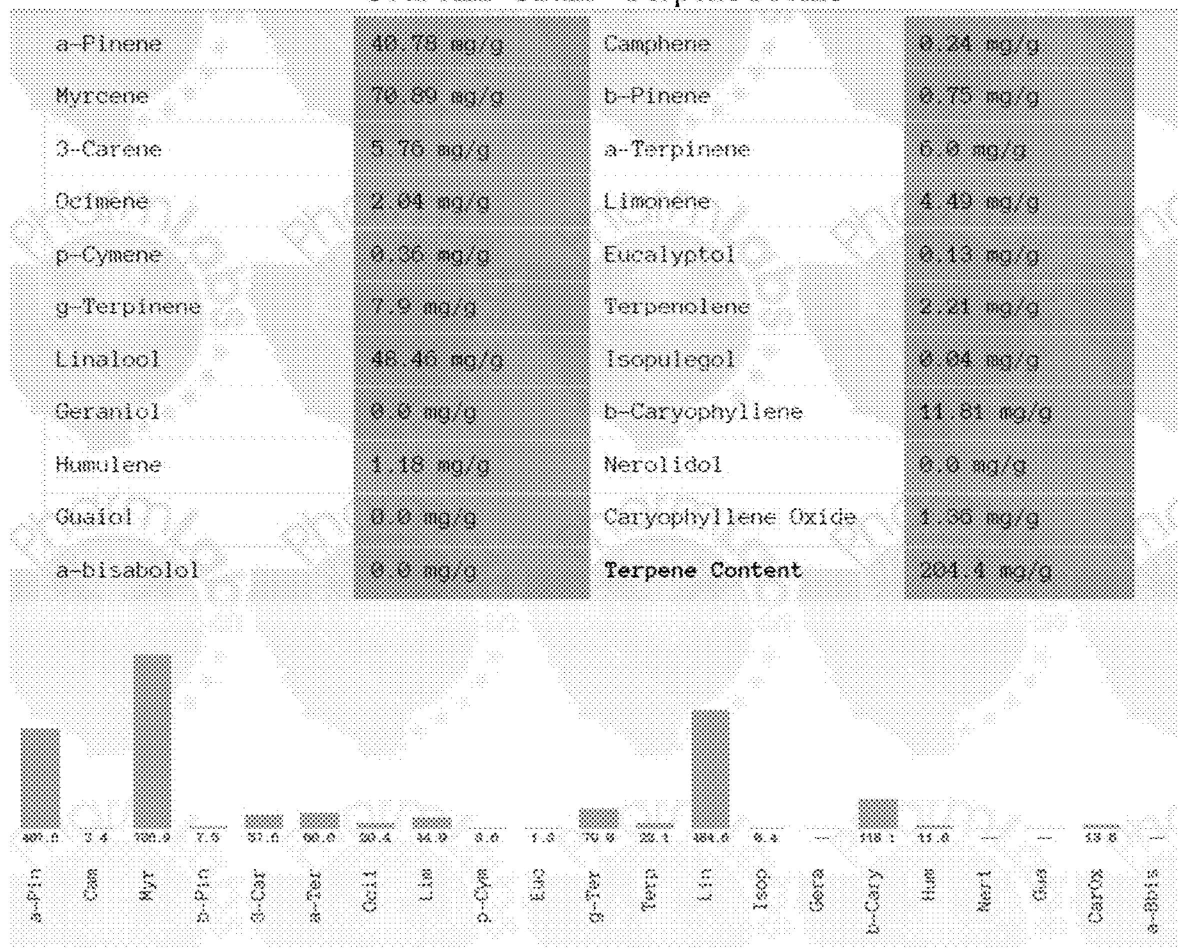

"Sour AK" Strain - Terpene Profile

| | | | |
|---|---|---|---|
| a-Pinene | 40.78 mg/g | Camphene | 0.24 mg/g |
| Myrcene | 70.89 mg/g | b-Pinene | 0.75 mg/g |
| 3-Carene | 5.76 mg/g | a-Terpinene | 6.0 mg/g |
| Ocimene | 2.04 mg/g | Limonene | 4.49 mg/g |
| p-Cymene | 0.36 mg/g | Eucalyptol | 0.13 mg/g |
| g-Terpinene | 7.9 mg/g | Terpenolene | 2.21 mg/g |
| Linalool | 48.46 mg/g | Isopulegol | 0.04 mg/g |
| Geraniol | 0.0 mg/g | b-Caryophyllene | 11.81 mg/g |
| Humulene | 1.18 mg/g | Nerolidol | 0.0 mg/g |
| Guaiol | 0.0 mg/g | Caryophyllene Oxide | 1.38 mg/g |
| a-bisabolol | 0.0 mg/g | **Terpene Content** | 204.4 mg/g |

*FIG. 10*

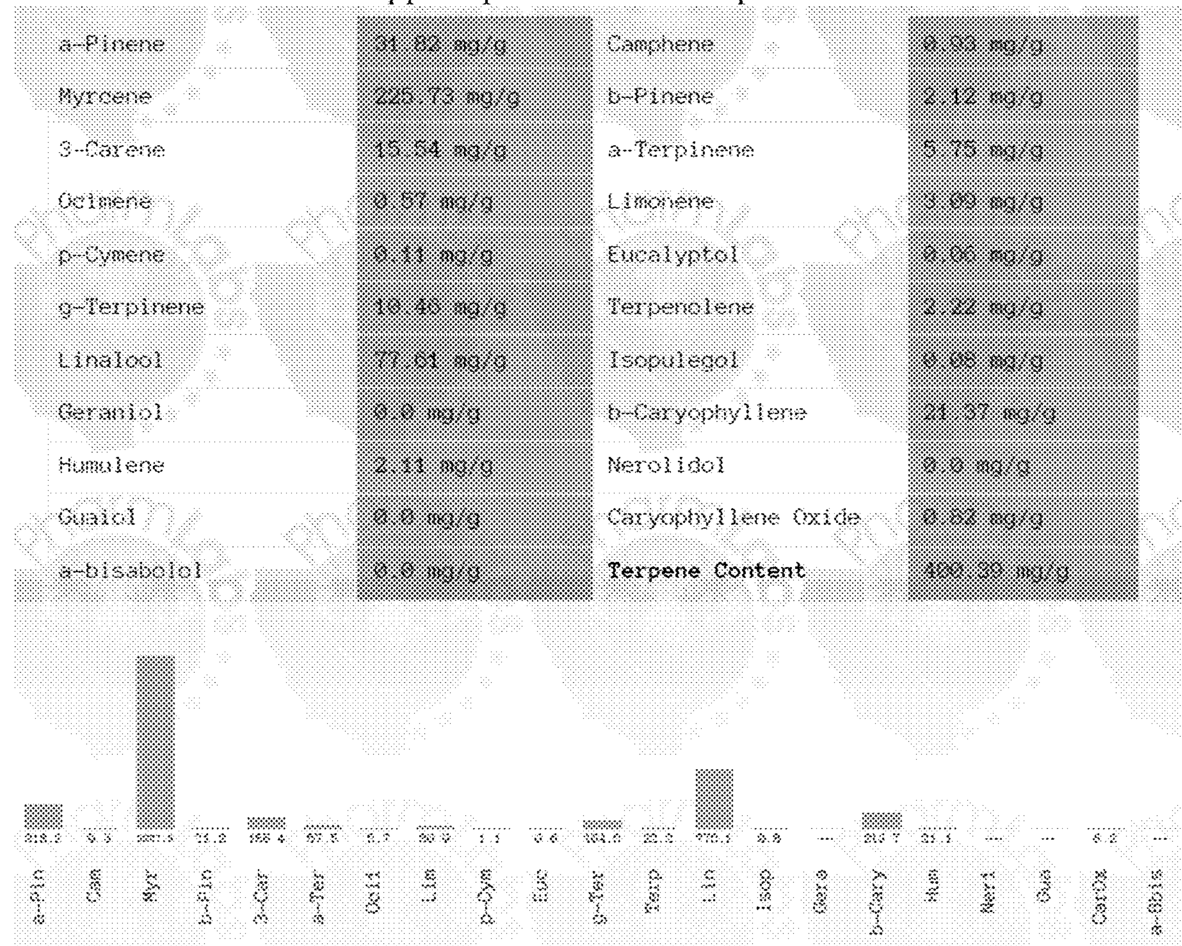

"Pineapple Xpress" Strain - Terpene Profile

| | | | |
|---|---|---|---|
| a-Pinene | 31.82 mg/g | Camphene | 0.93 mg/g |
| Myrcene | 225.73 mg/g | b-Pinene | 2.12 mg/g |
| 3-Carene | 15.54 mg/g | a-Terpinene | 5.75 mg/g |
| Ocimene | 0.57 mg/g | Limonene | 3.09 mg/g |
| p-Cymene | 0.11 mg/g | Eucalyptol | 0.06 mg/g |
| g-Terpinene | 10.46 mg/g | Terpenolene | 2.22 mg/g |
| Linalool | 77.61 mg/g | Isopulegol | 0.08 mg/g |
| Geraniol | 0.0 mg/g | b-Caryophyllene | 21.57 mg/g |
| Humulene | 2.11 mg/g | Nerolidol | 0.0 mg/g |
| Guaiol | 0.0 mg/g | Caryophyllene Oxide | 0.62 mg/g |
| a-bisabolol | 0.0 mg/g | **Terpene Content** | 400.39 mg/g |

*FIG. 11*

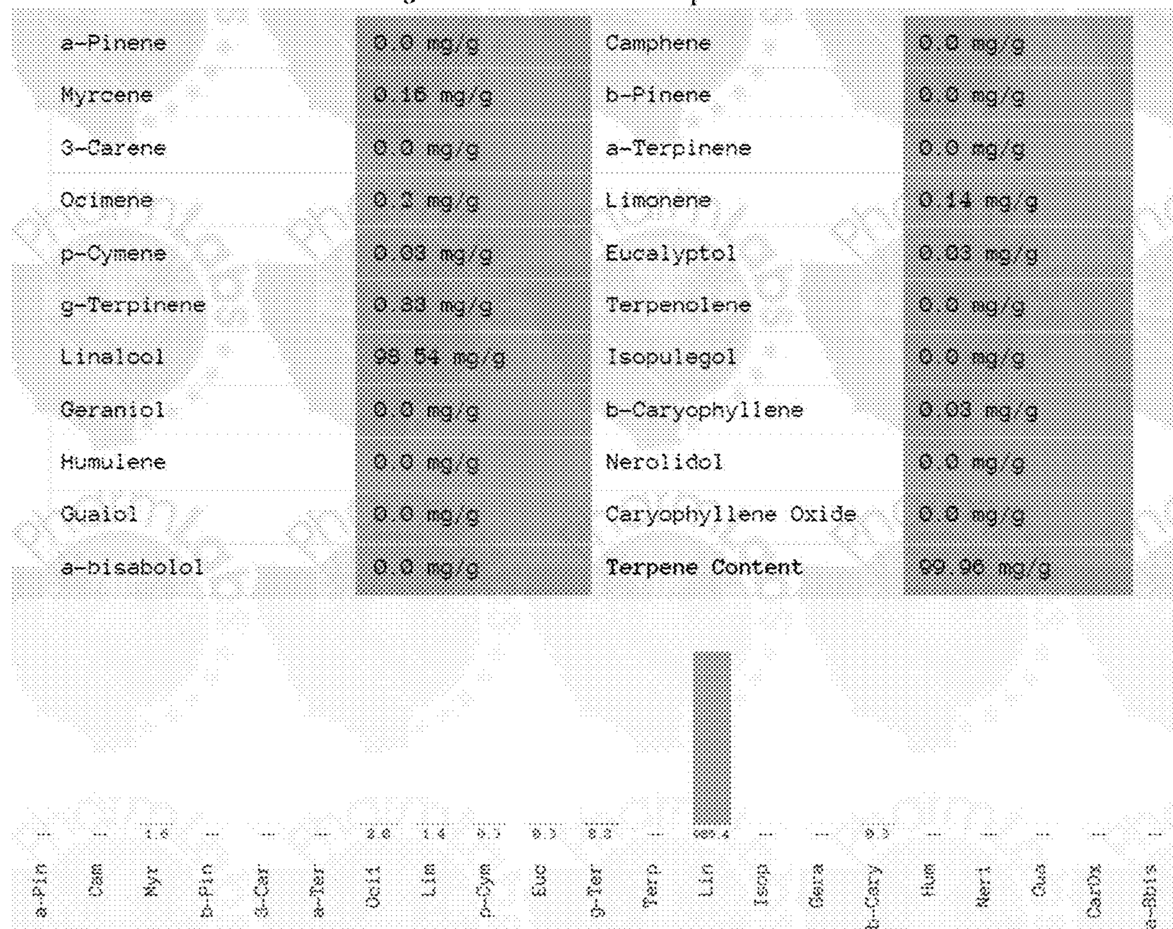

"TT JetFuel" Strain - Terpene Profile

| | | | |
|---|---|---|---|
| a-Pinene | 0.0 mg/g | Camphene | 0.0 mg/g |
| Myrcene | 0.15 mg/g | b-Pinene | 0.0 mg/g |
| 3-Carene | 0.0 mg/g | a-Terpinene | 0.0 mg/g |
| Ocimene | 0.5 mg/g | Limonene | 0.14 mg/g |
| p-Cymene | 0.03 mg/g | Eucalyptol | 0.03 mg/g |
| g-Terpinene | 0.33 mg/g | Terpenolene | 0.0 mg/g |
| Linalool | 98.54 mg/g | Isopulegol | 0.0 mg/g |
| Geraniol | 0.0 mg/g | b-Caryophyllene | 0.03 mg/g |
| Humulene | 0.0 mg/g | Nerolidol | 0.0 mg/g |
| Guaiol | 0.0 mg/g | Caryophyllene Oxide | 0.0 mg/g |
| a-bisabolol | 0.0 mg/g | Terpene Content | 99.96 mg/g |

*FIG. 12*

TERPENE-BASED COMPOSITIONS, METHODS OF PREPARATIONS AND USES THEREOF

CROSS-REFERENCE TO RELATED APPLICATIONS

The present application claims priority to U.S. Provisional Application Ser. No. 62/456,047, filed on Feb. 7, 2017, the disclosure of which is incorporated herein by reference in its entirety.

INCORPORATION OF THE SEQUENCE LISTING

The material in the accompanying sequence listing is hereby incorporated by reference into this application. The accompanying sequence listing text file, named WGREE-001A_Sequence_Listing.txt, was created on Feb. 5, 2018 and is 70 KB. The file can be assessed using Microsoft Word on a computer that uses Windows OS.

FIELD

Some embodiments relate to compositions for imparting one or more desired effects to a subject in which a plurality of chemical compounds which are known to occur in a cannabis strain and are associated with at least one desired effect in a subject are enriched and wherein the amounts or levels of the plurality of chemical compounds with respect to one another in said composition are about the amounts or levels of the plurality of chemical compounds with respect to one another in said cannabis strain. Some embodiments relate to terpene-based compositions for applications in the pharmaceutical and recreational fields. Also provided in some embodiments of the disclosure are methods for the preparation of the compositions, as well as methods for use thereof.

BACKGROUND

*Cannabis* is a genus of the flowering plant *Cannabis* which has long been used for drug and industrial purposes, fiber (hemp), for seed and seed oils, for medicinal purposes, and as a recreational drug. Industrial hemp products are made from *Cannabis* plants selected to produce an abundance of fiber. The *Cannabis* plant is an annual, dioecious, flowering herb indigenous to central Asia and the Indian subcontinent. The *Cannabis* plant material has been reported to contain suitable and desirable compounds, useful in various pharmaceutical dosage forms and methods of medical treatment. Cannabinoids, terpenoids, and flavonoids are included amongst the various suitable and desirable compounds.

The medicinal and psychoactive properties of the *Cannabis* plant have been documented for centuries. Growing evidence suggests that *Cannabis* is a safe, versatile and potentially inexpensive drug. It has been reported as being beneficial to patients suffering from a wide range of symptoms experienced in connection with various, often very serious, medical conditions. For example, *Cannabis* has been reported as being useful to alleviate symptoms associated with cancer, anorexia, chronic pain, spasticity, arthritis, migraine and many other illnesses. As a result, recent research into the use of cannabis-derived products for the treatment of a variety of diseases and conditions is reaching a feverish pace. In the United States, *Cannabis* has become an important, emerging medical option in a number of states. It is quickly becoming clear that drug formulations containing specific cannabis-derived chemical compounds can have dramatic affect in improving the lives of many patients. This extends well past the treatment of nausea, glaucoma, or pain relief which has been traditionally treated with cannabis as a “shotgun” approach. It has become clear that the use of targeted cannabis-derived chemical compounds for a specific ailment is much more effective.

The physiological and pharmacological effects of cannabis-derived products depend upon a number of factors, including the dosage level and the route of administration. In *Cannabis*, the content and composition of terpenes are strongly inherited and therefore have been widely used as biochemical markers in chemo-systematic studies to characterize plant species, provenances, clones and hybrids thereof. *Cannabis* plants can exhibit wide variation in the quantity and type of chemical compounds that they produce. In fact, a wide variability in terpenes, terpenoids, and/or cannabinoids content in different strains of *Cannabis* has been reported. In addition, as is also the case for many other plant species, *Cannabis* plants often exhibit dynamic biochemical changes when attacked by diseases and herbivores and in response to abiotic stresses, resulting in the induced production and release of aroma volatiles that are beneficial for direct or indirect defense. As a result, plant materials harvested from cannabis plants and products derived therefrom typically exhibit great variations in their chemical composition and quality.

Therefore, there is growing need for compositions, systems, and methods for the preparation of drug product formulations, for both medicinal and recreational use, in large quantity and with more consistent quality.

SUMMARY

This section provides a general summary of the present application, and is not comprehensive of its full scope or all of its features.

In one aspect, some embodiments disclosed herein relate to method of making a composition for imparting one or more desired effects to a subject. The method includes preparing a composition in which a plurality of chemical compounds which are known to occur in a cannabis strain and are associated with at least one desired effect in a subject are enriched, wherein the amounts or levels of the plurality of chemical compounds with respect to one another in the composition are about the amounts or levels of the plurality of chemical compounds with respect to one another in the cannabis strain.

Implementations of embodiments of the method according to this aspect and other aspects of the present disclosure can include one or more of the following features. In some embodiments, the preparation of the composition includes (i) obtaining a first enriched or purified composition of a first chemical compound from among the plurality of chemical compounds associated with at least one desired effect in a subject and which is known to occur in a cannabis strain, and (ii) combining the first enriched or purified composition with a second enriched or purified composition of a second chemical compound from among the plurality of chemical compounds associated with at least one desired effect in a subject and which is known to occur in the cannabis strain. In some embodiments, the plurality of chemical compounds are selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements. In some embodiments, the plurality of chemical compounds includes at least one terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the plurality of chemical compounds includes at least one terpene compound selected from the group consisting of caryophyllene, limonene, linalool, myrcene, α-pinene, and β-pinene.

In some embodiments disclosed herein, the amounts or levels of the plurality of chemical compounds relative to one another in the composition are about the amounts or levels of the plurality of chemical compounds relative to one another in a cannabis strain selected from FIGS. 1-12. In some embodiments, the total amount of terpenes in the composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume.

In some embodiments of the present disclosure, the composition further includes an essential oil. In some embodiments, the essential is lime oil. In some particular embodiments, the final concentration of essential oil in the composition is at least about 0.1%, at least about 0.2%, at least about 0.5%, at least about 1%, at least about 2%, at least about 3%, at least about 4%, at least about 5%, or at least about 10% by volume. In yet some embodiments, the final concentration of essential oil in the composition is from about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume.

In some embodiments disclosed herein, the plurality of chemical compounds includes one or more cannabinoid compound. In some embodiments, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CB G), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume.

In some embodiments of the present disclosure, the composition further includes a medium-chain fatty acid triester of glycerol, which is also known as medium-chain triglyceride—MCT. In some embodiments, the MCT includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the ratio of the MCT amount to the amount of the at least one terpene compound is from about 1:1000 to about 1000:1 by volume. In some embodiments, the ratio of the MCT amount to the amount of the at least one terpene compound is about 100:1 to about 3:1 by volume.

In some embodiments disclosed herein, the cannabis strain is a hybrid cannabis strain or an inbred cannabis strain. In some embodiments, the cannabis strain is a strain of *Cannabis sativa, Cannabis indica*, or *Cannabis ruderalis*. In some embodiments, the cannabis strain is a cannabis strain selected from the group consisting of ACDC PX, AG1 Lemon, AG2 Orange, Bluebbery OG, Jet Fuel, Kalashnikova, Keep Tahoe OG, Pineapple Xpress, Sour AK, Strawberry AK, Terpin Gorilla, and Watermelon OG. In some embodiments, a representative seed sample of the cannabis strain has been deposited under NCIMB Nos. 41541, 42254, 42255, 42256, 42257, and 42258.

In one aspect, some embodiments disclosed herein relate to a method for characterizing a cannabis strain, which includes identifying one or more genetic characteristics present in a biological sample from the cannabis strain wherein the one or more genetic characteristics are associated with a desired level or amount of one or more chemical compounds in the cannabis strain which is associated with at least one desired effect in a subject. In some embodiments, the method includes determining a plurality of genetic characteristics in a biological sample from the cannabis strain. In some embodiments, the plurality of genetic characteristics includes at least 2, at least 5, at least 10, at least 15, at least 20, at least 25, at least 50, or at least 100 genetic characteristics. In some embodiments, the plurality of genetic characteristics in the biological sample includes: (i) at least one molecular genetic marker selected from the group consisting of a simple sequence repeat (SSR), a cleaved amplified polymorphic sequence (CAPS), a simple sequence length polymorphism (SSLP), a restriction fragment length polymorphism (RFLP), a random amplified polymorphic DNA (RAPD) marker, a single nucleotide polymorphism (SNP), an amplified fragment length polymorphism (AFLP), an insertion, a deletion, an InDel mutation, an epigenetic alteration, a splicing variant, and a haplotype created from two or more of the above described molecular genetic marker; or (ii) at least one molecular genetic marker in conjunction with one or more phenotypic measurements, microarray data, analytical measurements (e.g., an RNA/protein overexpression, and an aberrant RNA/protein expression), biochemical measurements, environmental measurements, or transcription levels. In some embodiments, the identification of one or more genetic characteristics in the biological sample includes performing an analytical assay selected from the group consisting of nucleic acid sequencing, polypeptide sequencing, restriction digestion, nucleic acid amplification-based assays, nucleic acid hybridization assay, capillary electrophoresis, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), in-silico comparative genomics, and an enzymatic activity assay. In some embodiments, the identification of the one or more genetic characteristics in the biological sample comprises an antibody-based assay selected form the group consisting of ELISA, immunohistochemistry, western blotting, mass spectrometry, flow cytometry, protein-microarray, immunofluorescence, and a multiplex detection assay. In some embodiments, the one or more genetic characteristics in the biological sample is selected from the genetic characteristics described by Bakel et al. (supra, 2011)

In some embodiments, the method according to this aspect and other aspects of the present disclosure includes determining a plurality of genetic characteristics associated with a desired level or amount of a plurality of chemical compounds in the cannabis strain. In some embodiments, the plurality of chemical compounds includes at least 2, at least 3, at least 4, at least 5, at least 10, at least 15, at least 20, at least 25, at least 30, at least 35, or at least 40 chemical compounds.

In one aspect, some embodiments disclosed herein relate to a method of determining a profile of the amounts or levels of a plurality of chemical compounds associated with at least one desired effect in a subject, the method includes (i) obtaining a cannabis plant sample including the plurality chemical compounds, and (ii) determining the amounts or levels of the plurality chemical compounds in the cannabis plant sample.

In some embodiments of the methods disclosed herein, the determination of the level or amount of the plurality of chemical compounds includes an analytical assay selected from gas chromatography (GC), flame ionization detector (FID), thin layer chromatography (TLC) analysis, and high performance liquid chromatography (HPLC).

In one aspect, some embodiments disclosed herein relate to a composition for imparting one or more desired effects to a subject, wherein a plurality of chemical compounds which are known to occur in a cannabis strain and are associated with at least one desired effect in a subject are enriched in the composition and wherein the amounts or levels of the plurality of chemical compounds with respect to one another in the composition are about the amounts or levels of the plurality of chemical compounds with respect to one another in the cannabis strain. Implementations of embodiments of the composition according to this aspect and other aspects of the disclosure can include one or more of the following features. In some embodiments, the composition includes (i) a first enriched or purified composition of a first chemical compound from among the plurality of chemical compounds associated with at least one desired effect in a subject and which is known to occur in a cannabis strain, and (ii) a second enriched or purified composition of a second chemical compound from among the plurality of chemical compounds associated with at least one desired effect in a subject and which is known to occur in the cannabis strain. In some embodiments, the plurality of chemical compounds includes at least one terpene compound selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other element. In some embodiments, the plurality of chemical compounds includes at least one terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the plurality of chemical compounds includes at least one terpene compound selected from the group consisting of caryophyllene, limonene, linalool, myrcene, α-pinene, and β-pinene. In some embodiments, the amounts or levels of the plurality of chemical compounds relative to one another in the composition are about the amounts or levels of the plurality of chemical compounds relative to one another in a cannabis strain selected from FIGS. 1-12. In some embodiments, the total amount of terpenes in the composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume.

In some embodiments disclosed herein, the composition further includes an essential oil. In some embodiments, the essential is lime oil. In some embodiments, the final concentration of essential oil in the composition is at least about 0.1%, at least about 0.2%, at least about 0.5%, at least about 1%, at least about 2%, at least about 3%, at least about 4%, at least about 5%, or at least about 10% by volume. In some embodiments, the final concentration of lime oil in the composition is from about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume.

In some embodiments disclosed herein, the composition further includes one or more cannabinoid compound. In some embodiments, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA) active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA), active analogues and derivatives of any one thereof. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In some embodiments, the composition further comprises a medium-chain fatty acid triester of glycerol (medium-chain triglyceride—MCT). In some embodiments, the MCT includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the ratio of the MCT amount to the amount of the at least one terpene compound is from about 1:1000 to about 1000:1 by volume. In some embodiments, the ratio of the MCT amount to the amount of the at least one terpene compound is from about 100:1 to about 3:1 by volume.

In some embodiments disclosed herein, the cannabis strain is a hybrid cannabis strain or an inbred cannabis strain. In some embodiments, the cannabis strain is a strain of *Cannabis sativa, Cannabis indica*, or *Cannabis ruderalis*. In some embodiments, the cannabis strain is a cannabis strain selected from the group consisting of ACDC PX, Blubbery OG, Jet Fuel, Kalashnikova, Keep Tahoe OG, Pineapple Xpress, Sour AK, Strawberry AK, Terpin Gorilla, and Watermelon OG. In some embodiments, a representative seed sample of the cannabis strain has been deposited under NCIMB Nos. 41541, 42254, 42255, 42256, 42257, and 42258.

In one aspect, some embodiments of the present disclosure relate to a non-naturally occurring composition for conferring a desired effect to a subject, the composition including one or more cannabis terpene and a medium-chain triglyceride (MCT). In some embodiments, the one or more cannabis terpene is selected from the group consisting of monoterpenes, diterpenes, triterpenes, hemiterpenes, sesquiterpenes, sesterterpenes, sesquarterpenes, and notisoprenoids. In some embodiments, the one or more cannabis terpene is selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene.

In some embodiments, the non-naturally occurring composition of the present disclosure includes at least two cannabis terpenes selected from the group consisting of caryophyllene, myrcene, and α-pinene. In some embodiments, the non-naturally occurring composition further includes one or more additional cannabis terpene compounds selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the one or more additional cannabis terpene compounds is selected from the group consisting of the one or more terpene compounds are selected from the group consisting of caryophyllene, myrcene, α-pinene, limonene, linalool, and β-pinene.

In some embodiments, the total amount of terpenes in the composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the non-naturally occurring composition of the present disclosure further includes an amount of an essential oil. In some embodiments, the essential oil is lime oil. In some embodiments, the final concentration of essential oil in the composition is at least about 0.1%, at least about 0.2%, at least about 0.5%, at least about 1%, at least about 2%, at least about 3%, at least about 4%, at least about 5%, or at least about 10% by volume. In some embodiments, the final concentration of essential oil in the composition is from about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the non-naturally occurring composition of the present disclosure further includes one or more cannabinoid compound. In some embodiments, the at least one cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In some embodiments, the medium-chain triglyceride (MCT) of the non-naturally occurring composition of the present disclosure includes at least one medium-chain fatty acid having an aliphatic tail of 6-12 carbon atoms. In some embodiments, the at least one medium-chain fatty acid is selected from the group consisting of caproic acid (hexanoic acid), caprylic acid (ocanoic acid), capric acid (decanoic acid), and lauric acid (dodecanoic acid). In some embodiments, the at least one medium-chain fatty acid comprises caprylic acid. In some embodiments, the ratio of the MCT amount to the amount of the one or more cannabis terpene is of from about 1:1000 to 1000:1 by volume. In some embodiments, the ratio of the MCT amount to the amount of the one or more cannabis terpene is of about 100:1 to 3:1 by volume. In some embodiments, the desired effect is selected from the list consisting of reduced anxiety, reduced depression, improved alertness, cognitive ability enhancement, mood improvement, improved sleep quality, nausea reduction, pain relief, spasm relief, seizure decrease, muscle relaxation, antimicrobial, anti-diabetes, blood circulation improvement, psoriasis relief, anti-inflammation, relief of connective tissue disorder, bone stimulation, relief of rheumatoid arthritis, anti-oxidation, improvement to mobility (e.g., arthritis, multiple sclerosis), improvements to skin conditions (e.g., blemishes, scars, insect bites, hives, pimples), reduced seizures (epilepsy), reduction in hypertension, improved memory loss (e.g., dementia, Alzheimer's), reduced dependency on drugs (e.g. opioids, nicotine, alcohol), inhibition of cancer growth, increased metabolism, improvements to autoimmune disorders, appetite stimulation, reduced concussive injuries, and enhancement of skin penetration for transdermal delivery of therapeutic drug.

In some embodiments, the composition of the present disclosure is further formulated for administration orally, transdermally, topically, or parenterally. In some embodiments, the composition the present disclosure is further formulated into a form selected from a tablet, a vaporizer inhalant, a capsule, a gel, a power, an oral spray, a chewable gum, a sublingual film or lozenge, and a transdermal patch.

The foregoing summary is illustrative only and is not intended to be in any way limiting. In addition to the illustrative embodiments and features described herein, further aspects, embodiments, objects and features of the application will become fully apparent from the drawings and the detailed description and the claims.

BRIEF DESCRIPTION OF THE DRAWINGS

FIG. 1 illustrates an exemplary terpene profile of a plant sample derived from flower tissues of the cannabis strain "AG1 Lemon." The specific amounts of each of the terpene compounds present in the sample and the total terpene content are indicated.

FIG. 2 shows an exemplary terpene profile of a plant sample derived from flower tissues of the cannabis strain "AG2 Orange." The specific amounts of each of the terpene compounds present in the sample and the total terpene content are indicated.

FIG. 3 illustrates an exemplary terpene profile of a plant sample derived from the cannabis strain "Blueberry OG." The specific amounts of each of the terpene compounds present in the sample and the total terpene content are indicated.

FIG. 4 shows an exemplary terpene profile of a plant sample derived from the cannabis strain "Keep Tahoe OG." The specific amounts of each of the terpene compounds present in the sample and the total terpene content are indicated.

FIG. 5 is an exemplary terpene profile of a plant sample derived from the cannabis strain "ACDC PX." The specific amounts of each of the terpene compounds present in the sample and the total terpene content are indicated.

FIG. 6 shows an exemplary terpene profile of a plant sample derived from the cannabis strain "JetFuel." The specific amounts of each of the terpene compounds present in the sample and the total terpene content are indicated.

FIG. 7 illustrates an exemplary terpene profile of a plant sample derived from the cannabis strain "Watermelon OG." The specific amounts of each of the terpene compounds present in the sample and the total terpene content are indicated.

FIG. 8 is an exemplary terpene profile of a plant sample derived from the cannabis strain "Terpin Gorilla." The specific amounts of each of the terpene compounds present in the sample and the total terpene content are indicated.

FIG. 9 is an exemplary terpene profile of a plant sample derived from the cannabis strain "Strawberry AK." The specific amounts of each of the terpene compounds present in the sample and the total terpene content are indicated.

FIG. 10 shows an exemplary terpene profile of a plant sample derived from the cannabis strain "Sour AK." The specific amounts of each of the terpene compounds present in the sample and the total terpene content are indicated.

FIG. 11 shows an exemplary terpene profile of a plant sample derived from the cannabis strain "Pineapple Xpress." The specific amounts of each of the terpene compounds present in the sample and the total terpene content are indicated.

FIG. 12 shows an exemplary terpene profile of a plant sample derived from the cannabis strain "TT JetFuel." The specific amounts of each of the terpene compounds present in the sample and the total terpene content are indicated.

DETAILED DESCRIPTION

The present disclosure generally relates to methods and compositions including one or more chemical compounds which are known to occur in a *Cannabis* plant. Some embodiments disclosed herein relate to enriched formulations that are biomimetic to the aroma, flavor, and pharmaceutical effect of various biochemicals naturally present in particular strains of the *Cannabis* plant, including terpenes and cannabinoids. In some embodiments, these chemical compounds are formulated with one or more fatty acids in order to enhance the bioavailability of the chemical compounds' in the resulting formulations in humans, animals, and other biological systems. In some embodiments, these enriched formulations are prepared by recreating the desirable effects of existing *Cannabis* strains, based on knowledge acquired using genomic and/or analytical chemistry techniques. The precursors to the resulting formulations may be, for example, chemical extracts of the *Cannabis* plant or natural or synthetic versions of the chemicals present in *Cannabis*. One main function of these enriched formulations can be to replace the synergistic effects of *Cannabis* compounds when such effects would be lost in the extraction of cannabinoids from *Cannabis*. In some embodiments, the enriched formulations of the disclosure are prepared with the desired *Cannabis* compounds and one or more medium-chain fatty acid triester of glycerol, which is also known as medium-chain triglyceride—MCT, to provide enhanced bioavailability in the human body. For example, in some embodiments, the synergistic interaction between terpenes and cannabinoids, at times referred to as the "Entourage Effect", in the human body is preserved with the addition of formulations discussed in this disclosure. The synergy provides the user a more holistic experience whether utilized for recreational or medicinal purposes. As discussed further below, several formulations disclosed herein have been reported to relieve certain ailments in patients, such as anxiety in PTSD patients.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this disclosure.

References in the following detailed description to "one embodiment," "an embodiment," "an example embodiment," and the like, indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms "administration" and "administering", as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof.

A "bioavailability enhancer" as used herein is an agent or combination of agents that enhance the rate and/or extent of absorption of a compound, such as a *Cannabis*-derived compound, that reaches the systemic circulation and is available at the site of action. A bioavailability enhancer may also improve tissue distribution and targeting of the compound. Examples of bioavailability enhancers include, but are not limited to, liposomes, vitamin E, TPGS (d-α-tocopheryl polyethylene glycol 1000 succinate); acetylated monoglycerides; mono-, di-, and triglyceride esters of medium-chain (6-12 carbon atoms in length) and long-chain (more than 12 carbon atoms in length) fatty acids; esters of fatty acids and glycols or glycerol; esters of mixed fatty acids and glycols or glycerol; diesters of propylene glycol having from about 7 to about 55 carbon atoms; propylene glycol esters of capric and caprylic acids; citric acid, malic acid, ascorbic acid, fumarie acid, caproic acid, caprylic acid, cholic acid, glycocholic acid, sodium cholate, sodium lauryl sulfate, palmitoyl carnitin, cyclosporin A, polyoxyethylene/polyoxypropylene copolymers and other soluble polymers, solid lipid nanoparticles, and mixtures thereof. Soluble bioavailability-enhancing polymers to which compounds may be coupled to as targetable carriers or as compounds which are metabolized into a desired *Cannabis* compound include polyvinylpyrrolidone, pyran copolymer, polyhydroxylpropylmethacrylamide-phenoi, polyhydroxyethylasparta-midephenol, or polyethyleneoxide-polylysine substituted with palmitoyl residues. Furthermore, the compounds or drugs may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

As used herein, "concentrate" or "essential oil" refers to a substance obtained by extracting a raw material, using a solvent, wherein the solvent has substantially been removed. In some embodiments, the process of extracting a raw material using a solvent includes a hot solvent extraction. In some embodiments, the process of extracting a raw material using a solvent includes supercritical fluid extraction (SFE), such as, e.g., a fractional supercritical fluid extraction (FSFE).

As such, the term "*Cannabis* concentrate" or "*Cannabis* essential oil" refers to a substance obtained by extracting *Cannabis* (or any part thereof), wherein the solvent has substantially been removed. The *Cannabis* concentrate can be further enriched with certain desired products (e.g., cannabinoids, terpenoids, and/or flavonoids) from the *Cannabis* plant material.

As used herein, the term "cultivar" refers to a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

As used herein, "enrich" refers to an increase the concentration or amount of one substance, relative to the concentration or amount of another substance; or one material containing a higher concentration or amount of a substance, compared to a second material's concentration or amount of that substance. For example, in some embodiments, an a composition enriched for a *Cannabis* compound may have a higher concentration or amount of the compound relative to the concentration or amount of the compound in the *Cannabis* strain in which the compound is present. The increase in the amount (weight/mass) can be at least about 1%, at least about 5%, at least about 10%, at least about 25%, or at least about 50%. Likewise, the increase in concentration can be at least about 1%, at least about 5%, at least about 10%, at least about 25%, or at least about 50%. In reference to "higher concentration" and "lower concentration," the difference in concentration can be at least about 1%, at least about 5%, at least about 10%, at least about 25%, or at least about 50%.

"Entourage compound" is a compound that can increase the effects of one or more naturally-occurring ligands that bind to one or more receptors, but that has little or no affinity for the receptor. In a preferred, but non-limiting embodiment, an entourage compound increases the effects of a naturally-occurring ligand that binds to one or more cannabinoid receptors, but the entourage compound has little or no affinity for the cannabinoid receptor.

As used herein, "extract" refers to a composition obtained by extracting a raw material, using a solvent system. The term "extract of *Cannabis*" refers to a composition obtained by extracting *Cannabis* (or any part thereof). In some embodiments, the process of extracting a raw material using a solvent includes a hot solvent extraction. In some embodiments, the process of extracting a raw material using a solvent includes supercritical fluid extraction (SFE), such as, e.g., a fractional supercritical fluid extraction (FSFE). In reference to *Cannabis*, suitable extracts include, e.g., hash oil, tincture, or combination thereof.

As used herein, the term "inbreeding" refers to the production of offspring via the mating between relatives. The plants resulting from the inbreeding process are referred to herein as "inbred plants" or "inbreds".

As used herein, a "line" refers to a population of plants derived from a single cross, backcross or selfing. The individual offspring plants are not necessarily identical to one another. As distinguished from a "variety," a "line" displays less variation between individuals, generally (although not exclusively) by virtue of several generations of self-pollination. For purposes of this disclosure, a "line" is defined sufficiently broadly to include a group of plants vegetatively or clonally propagated from a single parent plant, using stem cuttings or tissue culture techniques. "Vegetative propagation", as used herein, refers to asexual propagation of the plant that is accomplished by taking and propagating cuttings, by grafting or budding, by layering, by division of plants, or by separation of specialized structure, such as stem, roots, tubers, rhizomes, or bulbs.

The term "breeding line", as used herein, refers to a line of a cultivated crop having commercially valuable or agronomically desirable characteristics, as opposed to wild varieties or landraces. The term includes reference to an elite breeding line or elite line, which represents a line of plants used to produce commercial F1 hybrids. An elite breeding line is obtained by breeding and selection for superior agronomic performance comprising a multitude of agronomically desirable traits.

The term "hybrid", as used herein, refers to any offspring of a cross between two genetically non-identical individuals. The parental plants may be related, as in production of a modified single cross, or unrelated. F1 hybrid, as used herein, refers to the first generation progeny of the cross of two genetically dissimilar plants.

The term "plant part" refers to any part of a plant including, but not limited to, organelles, single cells and cell tissues such as plant cells that are intact in plants, cell clumps and tissue cultures from which cannabis plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, and calli. The two main parts of plants grown in some sort of media, such as soil, are often referred to as the "above-ground" part, also often referred to as the "shoots", and the "below-ground" part, also often referred to as the "roots". The term "cannabis plant material" is to be interpreted as encompassing plant material derived from one or more *Cannabis* plants.

As used herein, "progeny" includes descendants of a particular plant or plant line. Progeny of an instant plant include seeds formed on F1, F2, F3, F4, F5, F6 and subsequent generation plants, or seeds formed on BC1, BC2, BC3, and subsequent generation plants, or seeds formed on F1BC1, FiBC2, FiBC3, and subsequent generation plants. The designation F1 refers to the progeny of a cross between two parents that are genetically distinct. The designations F2, F3, F4, F5 and F6 refer to subsequent generations of self- or sib-pollinated progeny of an F1 plant "Synergy" refers to the phenomenon where a first compound stimulates a first level of a particular activity, where a second compound stimulates a second level of the same particular activity, and where the presence of both compounds results in a third level of the same particular activity, where the third level is greater than the additive sum of the first level and the second level. Synergy can occur where the first compound and second compound are used at the same time, or where the first compound and second compound are used sequentially As used herein, "trichome" refers to a fine outgrowth or appendage on plants and certain protists. They are of diverse structure and function. In reference to *Cannabis*, the trichome is a glandular trichome that occurs most abundantly on the floral calyxes and bracts of female plants.

The term "variety" as used herein has the meaning to the corresponding definition in the International Convention for the Protection of New Varieties of Plants (UPOV Treaty). Thus, "variety" refers to a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc., are presented merely for ease of reading the specification and claims. The use of headings in the specification or claims does not require the steps or elements be performed in alphabetical or numerical order or the order in which they are presented.

Methods of the Disclosure

In one aspect, some embodiments disclosed herein relate to a method of making a composition for imparting one or more desired effects to a subject. The method includes preparing a composition in which a plurality of chemical compounds which are known to occur in a cannabis strain and are associated with at least one desired effect in a subject are enriched, wherein the amounts or levels of the plurality of chemical compounds with respect to one another in the composition are about the amounts or levels of the plurality of chemical compounds with respect to one another in the cannabis strain.

In principle, the methods according to the present disclosure can be applied to any plant, strain, varieties, and/or lines. Particularly suitable species include members of the plant family Cannabaceae. In some embodiments, the plant species is a species belonging to the genera *Cannabis* and *Humulus*. Non-limiting examples of *Humulus* species suitable for the compositions and methods disclosed herein include *Humulus japonicus* (syn. *H. scandens*), *Humulus lupulus, Humulus lupulus* var. *lupulus, Humulus lupulus* var. *cordifolius, Humulus lupulus* var. *lupuloides* (syn. *H. americanus*), *Humulus lupulus* var. *neomexicanus*, and *Humulus lupulus* var. *pubescens*. In some embodiments, the plant species is a species belonging to the genus *Cannabis.*

*Cannabis* is a genus of flowering plant that includes three species (and seven taxa) or subspecies, *C. sativa, C. indica*, and *C. ruderalis*. The plant is an annual, dioecious, flowering herb indigenous to central Asia and the Indian subcontinent. *Cannabis* is commonly reproduced by self-pollination and fertilization. This type of sexual reproduction facilitates the preservation of plant and variety characteristics during breeding and seed production. The preservation of these characteristics is often important to plant breeders for producing *Cannabis* plants having desired traits. *Cannabis* normally has imperfect flowers, with staminate "male" and pistillate "female" flowers occurring on separate plants. It is not unusual, however, for individual plants to bear both male and female flowers. Although monoecious plants are often referred to as "hermaphrodites", true hermaphrodites (which are less common) bear staminate and pistillate structures together on individual flowers, whereas monoecious plants bear male and female flowers at different locations on the same plant. Male flowers are normally borne on loose panicles, and female flowers are borne on racemes.

*Cannabis* is diploid, having a chromosome complement of 2n=20, although polyploid individuals have been artificially produced. The first genome sequence of *Cannabis*, which is estimated to be 820 Mb in size, was published in 2011 by Bakel et al., (*Genome Biology* 12(10): R102, 2011). All known strains of *Cannabis* are wind-pollinated and the fruit is an achene. Most strains of *Cannabis* are short day plants, with the possible exception of *C. sativa* subsp. *sativa* var. *spontanea* (=*C. ruderalis*), which is commonly described as "auto-flowering" and may be day-neutral.

The *Cannabis* plant material has been reported to contain suitable and desirable compounds, useful in various pharmaceutical dosage forms and methods of medical treatment. The suitable and desirable compounds may include, for example, one or more the following classes of compounds: cannabinoids, terpenoids, and flavonoids. These compounds can be obtained from the *Cannabis* in a pure or enriched state. The compounds obtained from the *Cannabis* can be in the form of an extract of *Cannabis*, or a concentrate of *Cannabis.*

For example, *Cannabis* has long been used for hemp fiber, for hemp oils, for medicinal purposes, and as a recreational drug. Industrial hemp products are made from cannabis plants selected to produce an abundance of fiber. The *Cannabis* plant can produce a wide variety of chemicals and compounds. About 140 of these belong to a large class of aromatic organic hydrocarbons known as terpenes and terpenoids. The main difference between terpenes and terpenoids is that terpenes are hydrocarbons; whereas, terpenoids have been denatured by oxidation (which may occur during drying and curing the flowers) or chemically modified.

Terpenes are synthesized in cannabis in secretory cells inside glandular trichomes, and production is increased with light exposure. These terpenes are mostly found in high concentrations in unfertilized female cannabis flowers prior to senescence (the condition or process of deterioration with age). The essential oil is extracted from the plant material by steam distillation or vaporization. Many terpenes vaporize around the same temperature as the cannabinoid Δ(9)-tetrahydrocannabinol (THC) which boils at about 157° C., but some terpenes are more volatile than others. Terpenes also play an important role by providing the plant with natural protection from bacteria and fungus, insects and other environmental stresses.

Terpenes have been found to be essential building blocks of complex plant hormones and molecules, pigments, sterols and even cannabinoids. Most notably, terpenes are responsible for the pleasant or not so pleasant, aromas of cannabis and the physiological effects associated with them. Patients will often ask to smell the cannabis when selecting their medicine. The idea is that certain aromas help identify different strains and their effects.

It has been reported that medical marijuana strains can vary greatly from one source to another, and even from one harvest to another. Those with relatively high concentrations of specific terpenes do, however, make them easier to identify by their smell than other strains. Most agree that varieties that smell of musk or of clove deliver sedative, relaxing effects (high level of the terpene myrcene); piney smells help promote mental alertness and memory retention (high level of the terpene pinene); and lemony aromas are favored for general uplift in mood and attitude (high level of limonene).

*Cannabis* plants can exhibit wide variation in the quantity and type of cannabinoids they produce. The mixture of cannabinoids produced by a plant is known as the plant's cannabinoid profile. Selective breeding has been used to control the genetics of plants and modify the cannabinoid profile. For example, strains that are used as fiber (commonly called hemp) are bred such that they are low in psychoactive chemicals like THC. Strains used in medicine are often bred for high CBD content, and strains used for recreational purposes are usually bred for high THC content or for a specific chemical balance. Some cannabis strains have been bred to produce minimal levels of tetrahydrocannabinol (THC), the principal psychoactive constituent. Many cannabis plants have been selectively bred to produce a maximum of cannabinoids (such as THC and/or CDB), which can be obtained by curing the flowers. Various compounds, including hashish and hash oil, can be extracted from the cannabis plant.

Accordingly, in some embodiments, the methods disclosed herein include a biological sample from a *Cannabis* plant. Generally, the biological sample can be any sample derived from a cannabis plant, and can be, for example, a nucleic acid sample, a protein sample, or a plant part. The term "plant part" refers to any part of a plant including, but not limited to, organelles, single cells and cell tissues such as plant cells that are intact in plants, cell clumps and tissue cultures from which cannabis plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, and calli. The two main parts of plants grown in some sort of media, such as soil, are often referred to as the "above-ground" part, also often referred to as the "shoots", and the "below-ground" part, also often referred to as the "roots". In some embodiments, the cannabis plant part can include flower tissues and/or trichomes.

Suitable cannabis species include *Cannabis sativa, Cannabis indica*, or *Cannabis ruderalis*. Hybrid cannabis strains and inbred cannabis strains are both suitable. Non-limiting examples of preferred cannabis strains include, but not limited to ACDC PX, AG1 Lemon, AG2 Orange, Agent Orange, Blackberry Kush, Blue Dream, Bluebbery OG, Bubba Kush, Cherry Pie, Durban Poison, Fire OG, Girl Scout Cookies, Gorilla Glue, Grape Ape, Green Crack, Headband, Jack Herer, Jet Fuel, Kalashnikova, Keep Tahoe OG, Kosher Kush, Master Kush, OG Kush, Pineapple Express, Pineapple Xpress, Purple Haze, Purple Kush, Purple Trainwreck, SFV OG, Skywalker OG, Sour AK, Sour Diesel, Strawberry AK, Super Lemon Haze, Super Silver Haze, Tahoe OG, Terpin Gorilla, Trainwreck, Watermelon OG, White Widow. Additional examples of preferred cannabis strains include, but are not limited to, cannabis strains that have been deposited under NCIMB Nos. 41541, 42254, 42255, 42256, 42257, and 42258.

Accordingly, in some embodiments, the methods according to the present disclosure include a cannabis strain selected from the group consisting of ACDC PX, AG1 Lemon, AG2 Orange, Bluebbery OG, Jet Fuel, Kalashnikova, Keep Tahoe OG, Pineapple Xpress, Sour AK, Strawberry AK, Terpin Gorilla, and Watermelon OG. In some preferred embodiments, the cannabis strain is AG1 Lemon strain or AG2 Orange strain. In some embodiments, a representative seed sample of the cannabis strain has been deposited under NCIMB Nos. 41541, 42254, 42255, 42256, 42257, and 42258.

Implementations of embodiments of the method according to this aspect and other aspects of the present disclosure can include one or more of the following features. In some embodiments, the preparation of the composition includes (i) obtaining a first enriched or purified composition of a first chemical compound from among the plurality of chemical compounds associated with at least one desired effect in a subject and which is known to occur in a cannabis strain, and (ii) combining the first enriched or purified composition with a second enriched or purified composition of a second chemical compound from among the plurality of chemical compounds associated with at least one desired effect in a subject and which is known to occur in the cannabis strain. In some embodiments, the plurality of chemical compounds include one or more compounds selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements.

Terpenes

In some embodiments of methods and compositions disclosed herein, the plurality of enriched chemical compounds can include one or more terpene compounds. Terpenes are a large and diverse class of organic compounds, produced by a variety of plants. They are often strong smelling and thus may have had a protective function. Terpenes are derived biosynthetically from units of isoprene, which has the molecular formula C5H8. The basic molecular formulae of terpenes are multiples of that, (C5H8)n where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids. Typically known for their olfactory stimulation, they are commonly used in the manufacture of chewing gum, candies and mints. They are also recognized for their diverse biological activity, often being touted as components which synergize with other endogenous and exogenous ligands. They are also recognized as entourage compounds, meaning that they increase the effects of ligands that bind to some receptors, while the terpenes themselves, have little affinity for the receptor.

In cannabis plants, terpenes naturally are biosynthesized from units of isoprene, which can be linked to form linear chains or rings. In increasing length, the terpenes include hemiterpenes (single isoprenoid unit), monoterpenes (two units), sesquiterpenes (three units), diterpenes (four units), sesterterpenes (five units), triterpenes (six units), and so on. Terpenes are also known as terpenoids.

The fragrance of fruits and flowers is primarily due to aerosolized terpenes that are registered by the olfactory receptor neurons in the nose. In citrus fruits, the major aromatic compounds are limonene (LIM) and eucalyptol (EUC), which are both terpenes. The aromatic compounds of clove oil include eugenol and β-caryophyllene (BCP), which are terpenes. The aromatic compounds of peppermint include LIM, menthone, and menthol, which are all terpenes.

The terpene composition of a sample, such as a plant, flower, fruit, leaves, etc. can be analyzed with analytical tools, such as chromatography or mass spectrometry. Nonetheless, establishing the actual type and amount of terpene in a sample can be difficult because there may be hundreds of different terpenes in a sample, and terpenes with very different properties may differ by only the stereochemistry at a single carbon atom. See, for example, the well-known difference between R-(−)-carvone, which smells like spearmint, and S-(+)-cavone, which smells like caraway. Accordingly, determining the type and amount of each terpene in a sample will often require the use of complimentary analytical techniques, such as LC-MS and GC-MS.

Some examples of terpenes, and their classification, are as follows.

Hemiterpenes: Examples of hemiterpenes, which do not necessarily have an odor, are 2-methyl-1,3-butadiene, hemialboside, and hymenoside.

Monoterpenes: pinene, α-pinene, β-pinene, cis-pinane, trans-pinane, cis-pinanol, trans-pinanol (Erman and Kane (2008) Chem. Biodivers. 5:910-919), limonene; linalool; myrcene; eucalyptol; α-phellandrene; β-phellandrene; α-ocimene; β-ocimene, cis-ocimene, ocimene, Δ-3-carene; fenchol; sabinene, borneol, isoborneol, camphene, camphor, phellandrene, α-phellandrene, α-terpinene, geraniol, linalool, nerol, menthol, myrcene, terpinolene, α-terpinolene, β-terpinolene, γ-terpinolene, Δ-terpinolene, α-terpineol, and trans-2-pinanol.

Sesquiterpenes: caryophyllene, caryophyllene oxide, humulene, α-humulene, α-bisabolene; β-bisabolene; santalol; selinene; nerolidol, bisabolol; α-cedrene, β-cedrene, β-eudesmol, eudesm-7(11)-en-4-ol, selina-3,7(11)-diene, guaiol, valencene, α-guaiene, β-guaiene, A-guaiene, guaiene, farnesene, α-farnesene, β-farnesene, elemene, α-elemene, β-elemene, γ-elemene, A-elemene, germacrene, germacrene A, germacrene B, germacrene C, germacrene D, and germacrene E.

Diterpenes: oridonin, phytol, and isophytol.

Triterpenes: ursolic acid, oleanolic acid.

1.5 ene": guaia-1(10),11-diene can be characterized as 1.5 ene. Guaia-1(10),11-diene is halfway between a monoterpene and diterpene, in terms of how many isoprenoid units are present. Monoterpene is $C_{10}H_{16}$, and diterpene is $C_{20}H_{32}$. Guaia-1(10),11-diene is $C_{15}H_{24}$. Isoprene is $C_5H_8$ (two double bonds).

Terpenoids, also known as isoprenoids, are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Plant terpenoids are used extensively for their aromatic qualities. They play a role in traditional herbal remedies and are under investigation for antibacterial, antineoplastic, and other pharmaceutical functions. The terpene Linalool for example, has been found to have anti-convulsant properties (Elisabetsky et al., Phytomedicine, May 6(2):107-13 1999). Well-known terpenoids include citral, menthol, camphor, salvinorin A in the plant *Salvia divinorum*, and the cannabinoids found in *Cannabis*. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

In some embodiments of the present disclosure, the plurality of enriched chemical compounds which are known to occur in a cannabis strain and are associated with at least one desired effect in a subject includes at least one cannabis terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds can include at least one, at least two, at least three, at least four, at least five, at least six, at least seven, at least eight, at least nine, at least ten, at least eleven, or at least twelve terpene compounds. In some embodiments, the plurality of chemical compounds can include 1, 2, 3, 4, 5, 6, 7, 8, 9, or 10 terpene compounds. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the plurality of chemical compounds includes at least one terpene compound selected from the group consisting of caryophyllene, limonene, linalool, myrcene, α-pinene, and β-pinene. In some embodiments, the plurality of chemical compounds includes at least one terpene compound selected from the group consisting of caryophyllene, myrcene, and α-pinene.

In accordance with the methods and compositions of the present disclosure, terpene compounds can be acquired commercially, in various purities, and are useful biochemical agents for a variety of olfactory and physiologically stimulating purposes. There are suppliers of terpenes that are pure and homogeneous, contract laboratories that synthesize terpenes, and contract laboratories that purify terpenes from natural products, e.g., essential oils, are available (see, e.g., Sigma-Aldrich, St. Louis, Mo.; TCI America, Portland, Oreg.; Arizona Chemical, Jacksonville, Fla.). Without implying any limitation, the term "pure" can refer to a terpene that is over 95% pure, over 98% pure, over 99% pure, over 99.5% pure, over 99.9% pure, over 99.99% pure, and the like. Generally, the term "pure" does not take into account any solvent that may be used for dissolving the terpene, such as a solvent that is ethanol, acetone, tetrahydrofuran, and so on. In other words, unless specified otherwise, either explicitly or by the context, any solvent that is present is not relevant to the characterization of a given terpene as pure and homogeneous.

Generally, the one or more terpene compounds can be incorporated in the compositions and methods of the present disclosure in any suitable concentrations, which can be determined based on requirements of specific end applications. In this regard, a number of physiological parameters have been developed in the past decades and documented in various studies of mammalian, such as human, subject's response to administration of terpene compounds. These parameters include blood oxygen saturation, pulse rate, breathing rate, eye-blinks, skin conductance, skin temperature, and surface electromyogram (Heuberger et al., Neuropsychopharmacology. 29:1925-1932, 2004). Various subjective parameters can also be tested, in subject response to terpenes, including subjective attentiveness, mood, cheerfulness, subjective relaxation, vigor, calmness, and alertness (see, e.g., Heuberger et al (2004) Neuropsychopharmacology. 29:1925-1932; Diego et al. (1998) Int. J. Neurosci. 96:217-224; Knasko (1992) Chem. Senses. 17; 27-35), have a number of sensory tests can also be used for assessing subjective responses to variety of terpene-containing oils (Sugawara et al. J. Home Econ. Jpn. 49:1281-1290, 1998; Sugawara et al. Molecules. 18:3312-3338, 2013; Satoh and Sugawara, Analytical Sciences. 19:139-146, 2003). In these tests, the terpene-containing oils were tested for subjective impressions, that is, fresh-stale, soothing-activating, airy-heavy, plain-rich, natural-unnatural, elegant-unrefined, soft-strong, pleasant-unpleasant, warm-cool, comfortable-uncomfortable, woodsy-not woodsy, floral-peppery, lively-dull. Sugawara's group also provided methods for the statistical analysis of data on subjective response, for example, calculation of the p value and electroencephalography data.

In some embodiments, the amounts or levels of the plurality of terpene compounds relative to one another in the composition are about the amounts or levels of the plurality of terpene compounds relative to one another in a cannabis strain. In some preferred embodiments, the amounts or levels of the plurality of terpene compounds relative to one another in the composition are about the amounts or levels of the plurality of terpene compounds relative to one another in a cannabis strain as set forth in FIGS. 1-12.

In some embodiments, the total amount of terpenes in the prepared composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the total amount of terpenes in the composition is about 25%, about 50%, or about 75% of the total volume.

Isolation and Analysis of Terpenes

In accordance with the present disclosure, cannabis terpenes can be purified, analyzed, and identified, by any one of methodologies and techniques known in the art. Non-limiting examples of suitable methodologies and techniques include high pressure liquid chromography (HPLC), gas chromatography, and other chromatographic techniques (see, e.g., Musenga et al. J. Sep. Sci. 29:1251-1258, 2006; Yang et al. J. Nat. Prod. 72:484-487, 2009; Jella et al. J. Agric. Food Chem. 46:242-247, 1998; Andrea et al. J. Agric. Food Chem. 51:4978-4983, 2003; Villa et al. J. Pharm. Biomed. Anal. 44:755-762, 2007).

Other suitable techniques suitable for analysis and/or quantification of cannabis terpenes and other chemicals include, but are not limited to, mass spectrometry (Hendriks and Bruins, Biol. Mass Spectrom. 10:377-381, 1983); gas chromatography-mass spectrometry (GC-MS) (Gadulo et al. J. Food Sci. 75:C199-207, 2010), nuclear magnetic resonance (NMR) (Mucci et al., Food Chem. 141:3167-3176, 2013; Zhang et al., Food Chem. 138:208-213, 2013); mass spectroscopy; and Matrix-Assisted Laser Desorption/Ionization Time-of-Flight mass spectrometry (MALDI-TOF) (Scalarone et al., J. Mass Spectrom. 40:1527-1535, 2005).

Essential Oils

In some embodiments, the methods and compositions as disclosed herein can further include one or more specific essential oils. The essential oil suitable for the methods and compositions disclosed herein can generally be any essential oil and can include, but are not limited to, almond oil, anise oil, armoise oil, bergamote oil, cajeput oil, cardamom oil, cinnamon leaf oil, citronella oil, clove oil, cymbopogon oil (lemongrass), cypress oil, eucalyptus oil, fennel oil, geranium oil, girfole oil, grapefruit oil, jasmine oil, lavandin oil, lemon oil, lime oil, mandarin oil, mint oil, myrtle oil, neroli bigarade oil, ocimum oil, orange oil, patchouli oil, pepper oil, petitgrain oil, pine oil, rosemary oil, santalum oil, spearmint oil, thyme oil, valerian oil, verbena oil, vetiver oil, and wintergreen oil. In some particular embodiments, the methods and compositions disclosed herein include an amount of lime oil. In some embodiments, the methods and compositions as disclosed herein can exclude one or more of the essential oils above. In some particular embodiments, the methods and compositions disclosed herein specifically exclude lime oil. In some embodiments, the compositions and methods disclosed herein specifically exclude essential oil (i.e., no essential oil is present).

In principle, the one or more essential oil can be incorporated into the compositions and methods of the disclosure at any suitable concentrations. In some particular embodiments, the final concentration of essential oil in the compositions and methods disclosed herein is at least about 0.1%, at least about 0.2%, at least about 0.5%, at least about 1%, at least about 2%, at least about 3%, at least about 4%, at least about 5%, or at least about 10%, at least about 15%, or at least about 20% by volume. In various embodiments of the disclosure, the final concentration of essential oil in the composition is from about 0.1% to about 10%, from about 0.1% to about 15%, from about 0.5% to about 20%, about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the final concentration of essential oil in the compositions and methods disclosed herein is about 5%, 10%, or 15%. In some embodiments, the final concentration of essential oil in the compositions and methods disclosed herein is about 5%. In some embodiments, the final concentration of essential oil in the compositions and methods disclosed herein is about 15%.

Cannabinoids

In some embodiments of methods and compositions disclosed herein, the plurality of enriched chemical compounds can include one or more cannabinoid compounds. Cannabinoids are among the most studied group of secondary metabolites in *Cannabis*. Most exist in two forms, as acids and in neutral (decarboxylated) forms. The acid form is designated by an "A" at the end of its acronym (i.e. THCA). The cannabinoids are synthesized in the plant as acid forms, and while some decarboxylation does occur in the plant, it increases significantly post-harvest and the kinetics-increase at high temperatures. The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

Phytocannabinoids, also called natural cannabinoids or herbal cannabinoids, are compounds produced by botanicals, most commonly *Cannabis sativa* L. and are often found in both carboxylated, acidic, and neutral forms, such as cannabidiolic acid (CBDA) and cannabidiol (CBD), respectively. Neutral phytocannabinoids can be derived from heating cannabinoid acids to perform the event referred to as decarboxylation. At least 85 different cannabinoids have been isolated from the *Cannabis* plants (El-Alfy et al., 2010, *Pharmacology Biochemistry and Behavior* 95 (4): 434-42).

Various cultivars of *Cannabis sativa* L. can produce varying cannabinoid ratios and unique and diverse cannabinoid profiles, with their cannabinoids being produced in the trichomes of the plant, often in a sticky icky resinous form comprised with associated terpenes. These components are cytotoxic to the plant and are thus produced and stored in the trichomes to ward of predators and used in chemical botanical warfare.

In some embodiments, the plurality of enriched chemical compounds can include at least one, at least two, at least three, at least four, at least five, at least six, at least seven, at least eight, at least nine, at least ten, at least eleven, or at least twelve cannabinoid compounds. In some embodiments, the plurality of enriched chemical compounds can include 1, 2, 3, 4, 5, 6, 7, 8, 9, or 10 cannabinoid compounds. In some embodiments of the disclosure, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA). In some embodiments, the methods and compositions as disclosed herein can exclude one or more of the cannabinoid compounds described above. In some particular embodiments, the methods and compositions disclosed herein specifically exclude THC and/or CBD. In some embodiments, the compositions and methods disclosed herein specifically exclude cannabinoids (i.e., no cannabinoid is present).

Generally, the one or more cannabinoid compounds can be incorporated in the compositions and methods of the present disclosure in any suitable concentrations, which can be determined based on requirements of specific end applications. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In various embodiments of the disclosure, the amount of the one or more cannabinoid compound is from about 1% to about 50%, from about 10% to about 80%, from about 20% to about 90%, from about 30% to about 98% from about 5% to about 15%, from about 10% to about 25%, from about 20% to about 35%, from about 30% to about 45%, from about 40% to about 55%, or from about 80% to about 98% of the total volume.

Medium-Chain Triglyceride—MCT

In some embodiments, the methods and compositions disclosed herein can include one or more medium-chain fatty acid triester of glycerol, which is also known as medium-chain triglyceride—MCT. Medium-chain triglycerides (MCTs) are triglycerides whose fatty acids have an aliphatic tail of 6-12 carbon atoms. The fatty acids found in MCTs are called medium-chain fatty acids (MCFAs). Like all triglycerides, MCTs are composed of a glycerol backbone and three fatty acids. In the case of MCTs, 2 or 3 of the fatty acid chains attached to glycerol are of medium length. Non-limiting examples of MCFAs include caproic acid (C6:0), caprylic acid (C8:0), capric acid (C10:0), and lauric acid (C12:0). In addition, apart from the above listed straight chain (unbranched chain) fatty acids, side chain (branched chain) fatty acids, e.g. nonanoic acid, are other examples of medium-chain fatty acids. MCTs are bland compared to other fats and do, not generate off-notes (dissonant tastes) as quickly as long-chain triglycerides (LCTs). They are also more polar than LCTs. The addition of MCT was used initially as a dilutant. However, recent research indicates that the MCT creates a more bioavailable composition. In addition, due to their ability to be absorbed rapidly by the body, medium-chain triglycerides have found use in the treatment of a variety of malabsorption ailments. Because of these attributes, they are widely used as solvents for flavors and oral medicines and vitamins.

Accordingly, in some embodiments of the disclosure, the MCT of the compositions and methods disclosed herein includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the methods and compositions as disclosed herein can exclude one or more of the MCTs described above. In some embodiments, the compositions and methods disclosed herein specifically exclude MCTs (i.e., no MCT is present). In some embodiments, when the methods and compositions as disclosed herein include one or more MCTs, at least one of the one or more MCTs is an MCT derived from cannabis seed.

In some embodiments, the ratio of the MCT amount to the amount of the at least one terpene compound is from about 1:1000 to about 1000:1 by volume. In various embodiments of the disclosure, the ratio of the MCT amount to the amount of the at least one terpene compound is from about 1:1000 to about 100:1, from about 1:1000 to about 10:1, from about 100:1 to about 10:1, from about 1:500 to about 500:1, from about 1:100 to about 100:1, from about 1:20 to about 20:1, from about 10:1 to about 1:10, from about 1:50 to about 5:1, from about 1:2 to about 2:1. In some embodiments, the ratio of the MCT amount to the amount of the at least one terpene compound is about 100:1 to about 3:1 by volume. In some embodiments, the ratio of the MCT amount to the amount of the at least one terpene compound is about 50:1, about 40:1, about 30:1, about 20:1, about 10:1, about 5:1, about 3:1, about 2:1, or about 1:1. In some embodiments, the ratio of the MCT amount to the amount of the at least one terpene compound is about 3:1.

In one aspect, some embodiments disclosed herein relate to a method for characterizing a cannabis strain, which includes identifying one or more genetic characteristics present in a biological sample from the cannabis strain wherein the one or more genetic characteristics are associated with a desired level or amount of one or more chemical compounds in the cannabis strain which is associated with at least one desired effect in a subject.

In some embodiments, the method includes determining a plurality of genetic or epigenetic characteristics in a biological sample from the cannabis strain. The number of genetic or epigenetic characteristics can generally be any numbers. For example, in some embodiments, the plurality of genetic or epigenetic characteristics includes at least 2, at least 5, at least 10, at least 15, at least 20, at least 25, at least 50, or at least 100 genetic or epigenetic characteristics. In general, the plurality of genetic or epigenetic characteristics can be selected from any types of genetic or epigenetic characteristics or a combination of any thereof. For example, in some embodiments, the plurality of genetic or epigenetic characteristics in the biological sample can include at least one molecular genetic marker selected from the group consisting of a simple sequence repeat (SSR), a cleaved amplified polymorphic sequence (CAPS), a simple sequence length polymorphism (SSLP), a restriction fragment length polymorphism (RFLP), a random amplified polymorphic DNA (RAPD) marker, a single nucleotide polymorphism (SNP), an amplified fragment length polymorphism (AFLP), an insertion, a deletion, an InDel mutation, an epigenetic alteration, a splicing variant, and a haplotype created from two or more of the above described molecular genetic marker. In some embodiments, the plurality of genetic or epigenetic characteristics in the biological sample can include at least one molecular genetic marker in conjunction with one or more phenotypic measurements, microarray data, analytical measurements (e.g., an RNA/protein overexpression, and an aberrant RNA/protein expression), biochemical measurements, environmental measurements, or transcription levels.

In accordance with the present disclosure, genetic or epigenetic characteristics in the biological sample can be identified by one or more methodologies or techniques known in the art. Non-limiting examples of methodologies or techniques suitable for the identification of one or more genetic or epigenetic characteristics in the biological sample as disclosed herein includes performing an analytical assay selected from the group consisting of nucleic acid sequencing, polypeptide sequencing, restriction digestion, nucleic acid amplification-based assays, nucleic acid hybridization assay, capillary electrophoresis, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), in-silico comparative genomics, methylation analysis, linkage disequilibrium analysis, bioinformatics analysis, and an enzymatic activity assay. In some embodiments, the identification of the one or more genetic or epigenetic characteristics in the biological sample comprises an antibody-based assay selected form the group consisting of ELISA, immunohistochemistry, western blotting, mass spectrometry, flow cytometry, protein-microarray, immunofluorescence, and a multiplex detection assay. In some embodiments, the one or more genetic or epigenetic characteristics is selected from the genetic markers described by Bakel et al. (*Genome Biology* 12(10): R102, 2011), the content of which is hereby incorporated by reference in its entirety. In some embodiments, the one or more genetic or epigenetic characteristics in the biological sample is selected from the PE2EUKC3372906, PE2EUKC3373261, PE2EUKC3373508, PE2EUKC3373607, PE2EUKC3375323, PE2EUKC3376354, PE2EUKC3378841, PE2EUKC3379537, PE2EUKC3383039 alleles of the cannabinoid synthase gene. In some embodiments, the one or more genetic or epigenetic characteristics in the biological sample is selected from the PE2EUKC3373123, PE2EUKC3373262, PE2EUKC3373344, PE2EUKC3373785, PE2EUKC3373853, PE2EUKC3373917, PE2EUKC3374045, PE2EUKC3374046, PE2EUKC3374480, PE2EUKC3374792, PE2EUKC3374920, PE2EUKC3374958, PE2EUKC3376119, PE2EUKC3376254, PE2EUKC3376800, PE2EUKC3376880, PE2EUKC3376881, PE2EUKC3377036, PE2EUKC3377775, PE2EUKC3377954, PE2EUKC3378831, PE2EUKC3379063, PE2EUKC3379603, PE2EUKC3385636, PE2EUKC3398153 alleles of the terpene synthase genes. In some embodiments, the one or more genetic or epigenetic characteristics includes at least 2, at least 3, at least 4, at least 5, at least 6, at least 10, at least 20, at least 50, or at least 100 genetic or epigenetic characteristics. In some embodiments, the method according to this aspect and other aspects of the present disclosure includes determining a plurality of genetic or epigenetic characteristics associated with a desired level or amount of a plurality of chemical compounds in the cannabis strain. In some embodiments, the plurality of chemical compounds in the cannabis strain is selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements. In some embodiments, the plurality of chemical compounds in the cannabis strain includes at least one terpene compounds. In some embodiments, the plurality of chemical compounds in the cannabis strain includes at least one cannabinoid compounds. In some embodiments, the plurality of chemical compounds includes at least 2, at least 3, at least 4, at least 5, at least 10, at least 15, at least 20, at least 25, at least 30, at least 35, or at least 40 chemical compounds.

In a related aspect, the present disclosure also provides a method of determining a profile of the amounts or levels of a plurality of chemical compounds associated with at least one desired effect in a subject, the method includes (i) obtaining a cannabis plant sample including the plurality chemical compounds, and (ii) determining the amounts or levels of the plurality chemical compounds in the cannabis plant sample.

Accordingly, in some embodiments, the present disclosure relates to the enrichment or isolation and analysis of naturally-occurring chemical compounds from a cannabis plant, and also the preparation of enriched chemical compositions that mimic those compositions found in nature.

In some embodiments, the method according to this aspect includes: generating a library of chemical profiles, obtaining a biological sample, analyzing a chemical profile of the sample to identify a plurality of chemical compounds in the sample; quantifying the chemical compounds identified; and generating a database of chemical profiles based on those quantities. In some embodiments, the method further includes preparing an enriched chemical composition or a blend of chemical compounds that mimics one or more of the compositions and/or profiles represented in the database.

The sample can be from any plant or other natural product, including species of the genera *Cannabis* and *Humulus*. The analysis step may comprise separating chemical compounds from a mixture, genetic analysis, chemotaxonomic analysis, compound extraction, gas chromatography flame ionization detection, chemical formula identification, chromatography, or any other analytical chemistry technique described herein or otherwise known in the art. Chemical compounds such as, terpenes can be identified based on their chromatography profiles or other chemical properties of the analyzed compounds. Terpenes identified can be those listed in FIGS. 1-12, or any other terpenes. Terpenes may be quantified based on their mass fraction, percent weight, mole fraction, percentage by volume, or the like. The compounds and their quantities can be assembled as a library or database, or any other data management format known in the art. In embodiments that involve creating a prepared blend that mimics a naturally-occurring composition, the synthetic blend may comprise one or more naturally-occurring chemical compounds described herein, all of those chemical compounds, or a combination thereof.

In some embodiments, the present disclosure provides a composition that is further formulated into a liquid form. Non-limiting examples of suitable liquid formulation include a transparent liquid, a translucent liquid, an opaque liquid, a slurry, an emulsion, a suspension, a gel, and the like. The designation of liquid, slurry, emulsion, gel, and so on, refers to this characterization as determined at room temperature (e.g., about 23 degrees centigrade).

In some embodiments, one or more of various additional components can be included in the compositions as disclosed herein in order to achieve the desired properties. Suitable components include, but are not limited to, dipropylene glycol, phytol, isophytol, diethyl phthalate, isoparaffins, paraffins, silicon oils, perfluorinated aliphatic ethers, polyethylene glycols, glycol ethers, glycol ether esters, esters, ketones, propylene glycol, ethanol, dimethicone, and cyclomethicone.

In some embodiments, one or more solvents can be included. For example, solvents such as propylene glycol are commonly used in electronic cigarette (e-cigarette) formulations. For example, the addition of 10-70% cannabinoids to a mixture of terpenes and propylene glycol creates an emulsified mixture suitable for use in e-cigarettes.

In accordance with the present disclosure, the chemical profile of a biological sample, such as a plant, flower, fruit, leaves, etc. can be analyzed with one or more analytical assays and techniques such as, for example, chromatography or mass spectrometry. Nonetheless, establishing the actual type and amount of terpene in a sample can be difficult because there may be hundreds of different terpenes in a sample, and terpenes with very different properties may differ by only the stereochemistry at a single carbon atom. See, for example, the well-known difference between R-(−)-carvone, which smells like spearmint, and S-(+)-cavone, which smells like caraway. Accordingly, determining the type and amount of each terpene in a sample will often require the use of complimentary analytical techniques, such as LC-MS and GC-M.

Quantitative analysis of a plant's cannabinoid profile is often determined by gas chromatography (GC), or more reliably by gas chromatography combined with mass spectrometry (GC/MS). Liquid chromatography (LC) techniques are also possible and, unlike GC methods, can differentiate between the acid and neutral forms of the cannabinoids.

Accordingly, in some embodiments of the methods disclosed herein, the determination of the level or amount of the plurality of chemical compounds includes an analytical assay selected from gas chromatography (GC), flame ionization detector (FID), thin layer chromatography (TLC) analysis, and high performance liquid chromatography (HPLC). In certain embodiments, the analytical assay used to determine the level or amount of the plurality of chemical compounds includes a GC-FID or GC-MS with headspace analyzer. In certain embodiments, the analytical assay used to determine the level or amount of the plurality of chemical compounds includes in injection analysis with GC-FID or HPLC.

In principle, the methods according to the present disclosure can be applied to any cannabis plant, strain, varieties, and/or lines. Particularly suitable species include members of the genera *Cannabis* and *Humulus*. In some embodiments, the plant species is a species belonging to the genus *Cannabis*.

Suitable cannabis species include *Cannabis sativa, Cannabis indica*, or *Cannabis ruderalis*. Hybrid cannabis strains and inbred cannabis strains are both suitable. Non-limiting examples of preferred cannabis strains include, but not limited to ACDC PX, AG1 Lemon, AG2 Orange, Agent Orange, Blackberry Kush, Blue Dream, Bluebbery OG, Bubba Kush, Cherry Pie, Durban Poison, Fire OG, Girl Scout Cookies, Gorilla Glue, Grape Ape, Green Crack, Headband, Jack Herer, Jet Fuel, Kalashnikova, Keep Tahoe OG, Kosher Kush, Master Kush, OG Kush, Pineapple Express, Pineapple Xpress, Purple Haze, Purple Kush, Purple Trainwreck, SFV OG, Skywalker OG, Sour AK, Sour Diesel, Strawberry AK, Super Lemon Haze, Super Silver Haze, Tahoe OG, Terpin Gorilla, Trainwreck, Watermelon OG, White Widow. Additional examples of preferred cannabis strains include, but are not limited to, cannabis strains that have been deposited under NCIMB Nos. 41541, 42254, 42255, 42256, 42257, and 42258.

Accordingly, in some embodiments, the compositions and methods according to the present disclosure include a cannabis strain selected from the group consisting of ACDC PX, AG1 Lemon, AG2 Orange, Bluebbery OG, Jet Fuel, Kalashnikova, Keep Tahoe OG, Pineapple Xpress, Sour AK, Strawberry AK, Terpin Gorilla, and Watermelon OG. In some preferred embodiments, the cannabis strain is AG1 Lemon strain or AG2 Orange strain. In some embodiments, a representative seed sample of the cannabis strain has been deposited under NCIMB Nos. 41541, 42254, 42255, 42256, 42257, and 42258.

COMPOSITIONS OF THE DISCLOSURE

In one aspect, some embodiments disclosed herein relate to a composition for imparting one or more desired effects to a subject, wherein a plurality of chemical compounds which are known to occur in a cannabis strain and are associated with at least one desired effect in a subject are enriched in the composition and wherein the amounts or levels of the plurality of chemical compounds with respect to one another in the composition are about the amounts or levels of the plurality of chemical compounds with respect to one another in the cannabis strain. As described in further detail below, implementations of embodiments of the composition according to this aspect and other aspects of the disclosure can include one or more of the following features.

In some embodiments, the composition includes (i) a first enriched or purified composition of a first chemical compound from among the plurality of chemical compounds associated with at least one desired effect in a subject and which is known to occur in a cannabis strain, and (ii) a second enriched or purified composition of a second chemical compound from among the plurality of chemical compounds associated with at least one desired effect in a subject and which is known to occur in the cannabis strain.

In some embodiments, the plurality of chemical compounds includes at least one terpene compound selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements.

In some embodiments, the plurality of chemical compounds which are known to occur in a cannabis strain and are associated with at least one desired effect in a subject includes at least one cannabis terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds can include at least one, at least two, at least three, at least four, at least five, at least six, at least seven, at least eight, at least nine, at least ten, at least eleven, or at least twelve terpene compounds. In some embodiments, the plurality of chemical compounds includes 1, 2, 3, 4, 5, 6, 7, 8, 9, or 10 terpene compounds. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, In some embodiments, the plurality of chemical compounds includes at least one terpene compound selected from the group consisting of caryophyllene, limonene, linalool, myrcene, α-pinene, and β-pinene. In some embodiments, the plurality of chemical compounds includes at least one terpene compound selected from the group consisting of caryophyllene, myrcene, and α-pinene.

Generally, the one or more terpene compounds can be incorporated in the compositions of the present disclosure in any suitable concentrations, which can be determined based on requirements of specific end applications. In some embodiments, the amounts or levels of the plurality of terpene compounds relative to one another in the composition are about the amounts or levels of the plurality of terpene compounds relative to one another in a cannabis strain. In some preferred embodiments, the amounts or levels of the plurality of terpene compounds relative to one another in the composition are about the amounts or levels of the plurality of terpene compounds relative to one another in a cannabis strain as set forth in FIGS. 1-12. In some embodiments, the total amount of terpenes in the prepared composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the total amount of terpenes in the composition is about 25%, about 50%, or about 75% of the total volume.

In some embodiments, the compositions as disclosed herein can further include one or more specific essential oils. The essential oil suitable for the compositions disclosed herein can generally be any essential oil and can include, but are not limited to, almond oil, anise oil, armoise oil, bergamote oil, cajeput oil, cardamom oil, cinnamon leaf oil, citronella oil, clove oil, cymbopogon oil (lemongrass), cypress oil, eucalyptus oil, fennel oil, geranium oil, girfole oil, grapefruit oil, jasmine oil, lavandin oil, lemon oil, lime oil, mandarin oil, mint oil, myrtle oil, neroli bigarade oil, ocimum oil, orange oil, patchouli oil, pepper oil, petitgrain oil, pine oil, rosemary oil, santalum oil, spearmint oil, thyme oil, valerian oil, verbena oil, vetiver oil, and wintergreen oil. In some particular embodiments, the compositions disclosed herein include an amount of lime oil. In some embodiments, the compositions as disclosed herein can exclude one or more of the essential oils above. In some particular embodiments, the compositions disclosed herein specifically exclude lime oil. In some embodiments, the compositions disclosed herein specifically exclude essential oil (i.e., no essential oil is present).

In principle, the one or more essential oil can be incorporated into the compositions of the disclosure at any suitable concentrations. In some particular embodiments, the final concentration of essential oil in the compositions disclosed herein is at least about 0.1%, at least about 0.2%, at least about 0.5%, at least about 1%, at least about 2%, at least about 3%, at least about 4%, at least about 5%, or at least about 10%, at least about 15%, or at least about 20% by volume. In various embodiments of the disclosure, the final concentration of essential oil in the composition is from about 0.1% to about 10%, from about 0.1% to about 15%, from about 0.5% to about 20%, about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the final concentration of essential oil in the compositions disclosed herein is 5%, 10%, or 15%. In some embodiments, the final concentration of essential oil in the compositions disclosed herein is 5%. In some embodiments, the final concentration of essential oil in the compositions disclosed herein is 15%.

In some embodiments disclosed herein, the composition further includes one or more cannabinoid compound. In some embodiments, the one or more cannabinoid compound includes at least one phytocannabinoid. In some embodiments, the composition can include at least one, at least two, at least three, at least four, at least five, at least six, at least seven, at least eight, at least nine, at least ten, at least eleven, or at least twelve cannabinoid compounds. In some embodiments, the comp can include 1, 2, 3, 4, 5, 6, 7, 8, 9, or 10 cannabinoid compounds. In some embodiments of the disclosure, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA). In some embodiments, the compositions as disclosed herein can exclude one or more of the cannabinoid compounds described above. In some particular embodiments, the compositions disclosed herein specifically exclude THC and/or CBD. In some embodiments, the compositions disclosed herein specifically exclude cannabinoids (i.e., no cannabinoid is present).

Generally, the one or more cannabinoid compounds can be incorporated in the compositions of the present disclosure in any suitable concentrations, which can be determined based on requirements of specific end applications. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In various embodiments of the disclosure, the amount of the one or more cannabinoid compound is from about 1% to about 50%, from about 10% to about 80%, from about 20% to about 90%, from about 30% to about 98% from about 5% to about 15%, from about 10% to about 25%, from about 20% to about 35%, from about 30% to about 45%, from about 40% to about 55%, or from about 80% to about 98% of the total volume.

In some embodiments, the composition can further include a medium-chain fatty acid triester of glycerol (medium-chain triglyceride—MCT). In some embodiments, the MCT of the compositions disclosed herein includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the methods and compositions as disclosed herein can exclude one or more of the MCTs described above. In some embodiments, the compositions and methods disclosed herein specifically exclude MTCs (i.e., no MCT is present).

In some embodiments, the ratio of the MCT amount to the amount of the at least one terpene compound is from about 1:1000 to about 1000:1 by volume. In various embodiments of the disclosure, the ratio of the MCT amount to the amount of the at least one terpene compound is from about 1:1000 to about 100:1, from about 1:1000 to about 10:1, from about 100:1 to about 10:1, from about 1:500 to about 500:1, from about 1:100 to about 100:1, from about 1:20 to about 20:1, from about 10:1 to about 1:10, from about 1:50 to about 5:1, from about 1:2 to about 2:1. In some embodiments, the ratio of the MCT amount to the amount of the at least one terpene compound is about 100:1 to about 3:1 by volume. In some embodiments, the ratio of the MCT amount to the amount of the at least one terpene compound is about 50:1, about 40:1, about 30:1, about 20:1, about 10:1, about 5:1, about 3:1, about 2:1, or about 1:1. In some embodiments, the ratio of the MCT amount to the amount of the at least one terpene compound is about 3:1.

In one aspect, some embodiments of the present disclosure relate to a non-naturally occurring composition for conferring a desired effect to a subject, the composition including one or more cannabis terpene and a medium-chain triglyceride (MCT).

In some embodiments of this aspect, the one or more cannabis terpene can be selected from the group consisting of monoterpenes, diterpenes, triterpenes, hemiterpenes, sesquiterpenes, sesterterpenes, sesquarterpenes, and notisoprenoids. In some embodiments, the one or more terpene compound includes at least one, at least two, at least three, at least four, at least five, at least six, at least seven, at least eight, at least nine, at least ten, at least eleven, or at least twelve terpene compounds. In some embodiments, the one or more terpene compound includes 1, 2, 3, 4, 5, 6, 7, 8, 9, or 10 terpene compounds. In some embodiments, the one or more cannabis terpene is selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene.

In some embodiments, the non-naturally occurring composition of the present disclosure includes at least two cannabis terpenes selected from the group consisting of caryophyllene, myrcene, and α-pinene. In some embodiments, the non-naturally occurring composition further includes one or more additional cannabis terpene compounds selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the one or more additional cannabis terpene compounds is selected from the group consisting of the one or more terpene compounds are selected from the group consisting of caryophyllene, myrcene, α-pinene, limonene, linalool, and β-pinene.

The one or more terpene compounds can be generally incorporated in the non-naturally occurring compositions of the present disclosure in any suitable concentrations, which can be determined based on requirements of specific end applications. In some embodiments, the total amount of terpenes in the prepared composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the total amount of terpenes in the composition is about 25%, about 50%, or about 75% of the total volume.

In some embodiments, the non-naturally occurring compositions as disclosed herein can further include one or more specific essential oils. The essential oil suitable for the non-naturally occurring compositions disclosed herein can generally be any essential oil and can include, but are not limited to, almond oil, anise oil, armoise oil, bergamote oil, cajeput oil, cardamom oil, cinnamon leaf oil, citronella oil, clove oil, cymbopogon oil (lemongrass), cypress oil, eucalyptus oil, fennel oil, geranium oil, girfole oil, grapefruit oil, jasmine oil, lavandin oil, lemon oil, lime oil, mandarin oil, mint oil, myrtle oil, neroli bigarade oil, ocimum oil, orange oil, patchouli oil, pepper oil, petitgrain oil, pine oil, rosemary oil, santalum oil, spearmint oil, thyme oil, valerian oil, verbena oil, vetiver oil, and wintergreen oil. In some particular embodiments, the non-naturally occurring compositions disclosed herein include an amount of lime oil. In some embodiments, the non-naturally occurring compositions as disclosed herein can exclude one or more of the essential oils above. In some particular embodiments, the non-naturally occurring compositions disclosed herein specifically exclude lime oil. In some embodiments, the non-naturally occurring compositions disclosed herein specifically exclude essential oil (i.e., no essential oil is present).

In some embodiments, the final concentration of essential oil in the non-naturally occurring compositions disclosed herein is at least about 0.1%, at least about 0.2%, at least about 0.5%, at least about 1%, at least about 2%, at least about 3%, at least about 4%, at least about 5%, or at least about 10%, at least about 15%, or at least about 20% by volume. In various embodiments of the disclosure, the final concentration of essential oil in the composition is from about 0.1% to about 10%, from about 0.1% to about 15%, from about 0.5% to about 20%, about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the final concentration of essential oil in the non-naturally occurring compositions disclosed herein is 5%, 10%, or 15%. In some embodiments, the final concentration of essential oil in the non-naturally occurring compositions disclosed herein is 5%. In some embodiments, the final concentration of essential oil in the non-naturally occurring compositions disclosed herein is 15%.

In some embodiments, the non-naturally occurring composition of the present disclosure further includes one or more cannabinoid compound. In some embodiments, the one or more cannabinoid compounds includes at least one phytocannabinoid. In some embodiments, the non-naturally occurring composition can include at least one, at least two, at least three, at least four, at least five, at least six, at least seven, at least eight, at least nine, at least ten, at least eleven, or at least twelve cannabinoid compounds. In some embodiments, the non-naturally occurring composition can include 1, 2, 3, 4, 5, 6, 7, 8, 9, or 10 cannabinoid compounds. In some embodiments, the at least one cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CB G), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA). In some embodiments, the non-naturally occurring compositions as disclosed herein can exclude one or more of the cannabinoid compounds described above. In some particular embodiments, the non-naturally occurring compositions disclosed herein specifically exclude THC and/or CBD. In some embodiments, the non-naturally occurring compositions disclosed herein specifically exclude cannabinoids (i.e., no cannabinoid is present).

Generally, the one or more cannabinoid compounds can be incorporated in the non-naturally occurring compositions of the present disclosure in any suitable concentrations, which can be determined based on requirements of specific end applications. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In various embodiments of the disclosure, the amount of the one or more cannabinoid compound is from about 1% to about 50%, from about 10% to about 80%, from about 20% to about 90%, from about 30% to about 98% from about 5% to about 15%, from about 10% to about 25%, from about 20% to about 35%, from about 30% to about 45%, from about 40% to about 55%, or from about 80% to about 98% of the total volume.

In some embodiments, the medium-chain triglyceride (MCT) of the non-naturally occurring composition of the present disclosure includes at least one medium-chain fatty acid having an aliphatic tail of 6-12 carbon atoms. In some embodiments, the at least one medium-chain fatty acid is selected from the group consisting of caproic acid (hexanoic acid), caprylic acid (ocanoic acid), capric acid (decanoic acid), and lauric acid (dodecanoic acid). In some embodiments, the at least one medium-chain fatty acid comprises caprylic acid. In some embodiments, the ratio of the MCT amount to the amount of the at least one terpene compound is from about 1:1000 to about 1000:1 by volume. In various embodiments of the disclosure, the ratio of the MCT amount to the amount of the at least one terpene compound is from about 1:1000 to about 100:1, from about 1:1000 to about 10:1, from about 100:1 to about 10:1, from about 1:500 to about 500:1, from about 1:100 to about 100:1, from about 1:20 to about 20:1, from about 10:1 to about 1:10, from about 1:50 to about 5:1, from about 1:2 to about 2:1. In some embodiments, the ratio of the MCT amount to the amount of the at least one terpene compound is about 100:1 to about 3:1 by volume. In some embodiments, the ratio of the MCT amount to the amount of the at least one terpene compound is about 50:1, about 40:1, about 30:1, about 20:1, about 10:1, about 5:1, about 3:1, about 2:1, or about 1:1. In some embodiments, the ratio of the MCT amount to the amount of the at least one terpene compound is about 3:1.

In some embodiments, the desired effect in a subject can generally by any desired effect known to be associated with one or more of the chemical compounds which are known to occur in a cannabis strain. Non-limiting examples of the desired effect in a subject include, but are not limited to, reduced anxiety, reduced depression, improved alertness, cognitive ability enhancement, mood improvement, improved sleep quality, nausea reduction, pain relief, spasm relief, seizure decrease, muscle relaxation, antimicrobial, anti-diabetes, blood circulation improvement, psoriasis relief, anti-inflammation, relief of connective tissue disorder, bone stimulation, relief of rheumatoid arthritis, anti-oxidation, improvement to mobility (e.g., arthritis, multiple sclerosis), improvements to skin conditions (e.g., blemishes, scars, insect bites, hives, pimples), reduced seizures (epilepsy), reduction in hypertension, improved memory loss (e.g., dementia, Alzheimer's), reduced dependency on drugs (e.g. opioids, nicotine, alcohol), inhibition of cancer growth, increased metabolism, improvements to autoimmune disorders, appetite stimulation, reduced concussive injuries, and enhancement of skin penetration for transdermal delivery of therapeutic drug.

Without implying any limitation, other flavoring ingredients and/or modifiers can be included in the compositions and methods of the present disclosure. Non-limiting examples of such flavoring ingredients and/or modifiers include sweeteners, 4-hydroxy-2,5-dimethyl-3(2H)-furanone (strawberry), ethyl butyrate (apple, fruity), isoamyl acetate (banana), propyl hexanoate (pineapple, fruity), allyl hexanoate (pineapple, fruity), valencene (orange, fresh fruity), methyl anthranilate (also known as methyl 2-aminobenzoate) (grape), methyl butyrate (fruity, apple, pineapple), benzyl acetate (fruity, strawberry), p-mentha-8-thiol-3-one (grapefruit), (1S,4S)-trans-p-menthan-8-thiol-3-one acetate (black currant, exotic), (1R,4S)-cis-p-menthan-8-thiol-3-one acetate (fruity, sweet).

In some embodiments, the compositions of the present disclosure can be further formulated for administration orally, transdermally, topically, or parenterally. In some embodiments, the compositions of the present disclosure can be further formulated into a form selected from a tablet, a vaporizer inhalant, a capsule, a gel, a power, an oral spray, a chewable gum, a sublingual film or lozenge, and a transdermal patch. As used herein, "oral delivery" or "oral administration" refers to a route of administration wherein the pharmaceutical dosage form is taken through the mouth. Oral administration is a part of enteral administration, which also includes buccal (dissolved inside the cheek), sublabial (dissolved under the lip) and sublingual administration (dissolved under the tongue). Enteral medications come in various forms, including: tablets to swallow, chew or dissolve in water or under the tongue; capsules and chewable capsules (with a coating that dissolves in the stomach or bowel to release the medication there); time-release or sustained-release tablets and capsules (which release the medication gradually); powders or granules; teas; drops; and liquid medications or syrups. As used herein, "dermal delivery" or "dermal administration" refers to a route of administration wherein the pharmaceutical dosage form is taken to, or through, the dermis (i.e., layer of skin between the epidermis (with which it makes up the cutis) and subcutaneous tissues).

As used herein, "transdermal patch" or "adhesive topical patch" refers to a medicated adhesive patch that is placed on the skin to deliver a specific dose of medication through the skin and into the bloodstream. A transdermal patch or transdermal system (TDS) is a medicated adhesive patch that is placed on the skin to deliver a specific dose of drug through the skin and into the bloodstream. An advantage of a transdermal drug delivery route over other types of medication delivery such as oral, topical, intravenous, intramuscular, etc. is that the patch provides a controlled release of the medication into the patient, usually through either a porous membrane covering a reservoir of medication or through body heat melting thin layers of medication embedded in the adhesive. The main disadvantage to transdermal delivery systems stems from the fact that the skin is a very effective barrier; as a result, only medications whose molecules are small enough to penetrate the skin can effectively be delivered by this method.

The transdermal patch serves as an alternative dosage form for patients who experience dysphagia (difficulty in swallowing). Additional reasons to use transdermal patches include the convenience of a dosage form that can be taken without water as well as the inability of the patient to eat or drink (e.g., nausea and/or vomiting).

In some embodiments, the compositions of the present disclosure can be encapsulated for protection of aroma compounds for use in foods and other applications. As used herein, "capsule" refers to a solid pharmaceutical oral dosage form wherein the active (and inactive) ingredient is encapsulated. Encapsulation refers to a range of techniques used to enclose medicines in a relatively stable shell known as a capsule, allowing them to, for example, be taken orally or be used as suppositories. The two main types of capsules include hard-shelled capsules, which are typically made using gelatin and contain dry, powdered ingredients or miniature pellets made by, e.g. processes of extrusion or spheronisation. These are made in two halves: a lower-diameter "body" that is filled and then sealed using a higher-diameter "cape". The second main type of capsules include soft-shelled capsules, primarily used for oils and for active ingredients that are dissolved or suspended in oil. Both of these classes of capsules are made from aqueous solutions of gelling agents like such as animal protein mainly gelatin; and plant polysaccharides or their derivatives like carrageenans and modified forms of starch and cellulose. Other ingredients can be added to the gelling agent solution like plasticizers such as glycerin and/or sorbitol to decrease the capsule's hardness, coloring agents, preservatives, disintegrants, lubricants and surface treatment. In certain embodiments, the compositions of the present disclosure can be encapsulated with β-cyclodextrin. Methods, systems, and related materials useful for molecular encapsulation of flavor compounds derived from *Cannabis* are known in the art (Reineccius T A et al. *Journal of Food Science,* 68(4), 1234-1239, 2003; Yamamoto et al., *Molecular encapsulation of citral or d-limonene flavor by spray drying*; Rubiano et al., Ing. Compet. vol. 17 no. 2 Cali 2015). In certain embodiments, the compositions of the present disclosure are encapsulated in alginate beads as a protection and delivery system.

The discussion of the general methods and compositions given herein is intended for illustrative purposes only. Other alternative methods, compositions, and alternatives will be apparent to those of skill in the art upon review of this disclosure, and are to be included within the spirit and purview of this application.

EXAMPLES

Additional alternatives are disclosed in further detail in the following examples, which are not in any way intended to limit the scope of the claims.

Example 1

Generating Terpene Profiles of *Cannabis* Strains

In this Example, plant samples from 12 cannabis strains were analyzed for their chemical properties. The analytical process typically involved obtaining a cannabis plant sample, followed by analyzing a chemical profile of the plant samples to identify chemical compounds therein. In some analyses, the analytical process involved gas chromatography (GC) coupled with flame ionization detector (FID). In some other analyses, the analytical process involved high performance liquid chromatography (HPLC). The analysis step may further comprise other processes for extracting compounds or otherwise preparing the sample for analysis. Additionally, in some analyses, a gas chromatography-mass spectrometry (GCMS) was used to identify compounds using solid-phase micro-extraction (SPME). The analytical process also included quantifying chemical compounds by mass fraction, percent weight, mole fraction, percentage by volume. The determined quantities can be used to further determine ratios of chemical compounds to one another in the respective plant samples. Subsequently, those determined quantities, ratios, or other chemical properties were entered into a database of chemical profiles. In some experiments, the chemical profile database was used in conjunction with a genetic database with corresponding genetic or epigenetic characteristics identified in the plant samples.

Example 2

Chemical Profiling of *Cannabis* Strain AG1 Lemon

This Example describes the terpene profile of a sample derived from the cannabis strain "AG1 Lemon". Flower tissues were used. The analytical assay was GC/FID with Headspace Analyzer.

FIG. 1 provides an exemplary terpene profile of a plant sample derived from flower tissues of the cannabis strain "AG1 Lemon." The specific amounts of each of the terpene compounds present in the sample and the total terpene content are indicated.

Example 3

Chemical Profiling of *Cannabis* Strain AG2 Orange

This Example describes the terpene profile of a sample derived from the cannabis strain AG2 Orange. Flower tissues were used. The analytical assay was GC/FID with Headspace Analyzer.

FIG. 2 provides an exemplary terpene profile of a plant sample derived from flower tissues of the cannabis strain "AG2 Orange." The specific amounts of each of the terpene compounds present in the sample and the total terpene content are indicated Example 4

Chemical Profiling of *Cannabis* Strain "Blueberry OG"

This Example describes the terpene profile of a sample derived from the cannabis strain "Blueberry OG". Flower tissues were used. The analytical assay was GC/FID with Headspace Analyzer.

FIG. 3 provides an exemplary terpene profile of a plant sample derived from the cannabis strain "Blueberry OG." The specific amounts of each of the terpene compounds present in the sample and the total terpene content are indicated.

Example 5

Chemical Profiling of *Cannabis* Strain "Keep Tahoe OG"

This Example describes the terpene profile of a sample derived from the cannabis strain "Keep Tahoe OG". Flower tissues were used. The analytical assay was GC/FID with Headspace Analyzer.

FIG. 4 provides an exemplary terpene profile of a plant sample derived from the cannabis strain "Keep Tahoe OG." The specific amounts of each of the terpene compounds present in the sample and the total terpene content are indicated.

Example 6

Chemical Profiling of *Cannabis* Strain "ACDC PX"

This Example describes the terpene profile of a sample derived from the cannabis strain "ACDC PX". Flower tissues were used. The analytical assay was GC/FID with Headspace Analyzer.

FIG. 5 provides a terpene profile of a plant sample derived from the cannabis strain "ACDC PX." The specific amounts of each of the terpene compounds present in the sample and the total terpene content are indicated.

Example 7

Chemical Profiling of *Cannabis* Strain "JetFuel"

This Example describes the terpene profile of a sample derived from the cannabis strain "JetFuel". Edible/tinctures (alcohol extracts of flower tissue) were used. The analytical assay was high performance liquid chromatography (HPLC).

FIG. 6 provides an exemplary terpene profile of a plant sample derived from the cannabis strain "JetFuel." The specific amounts of each of the terpene compounds present in the sample and the total terpene content are indicated.

Example 8

Chemical Profiling of *Cannabis* Strain "Watermelon OG"

This Example describes the terpene profile of a sample derived from the cannabis strain "Watermelon OG". Edible/tinctures (alcohol extracts of flower tissue) were used. The analytical assay was high performance liquid chromatography (HPLC).

FIG. 7 provides an exemplary terpene profile of a plant sample derived from the cannabis strain "Watermelon OG." The specific amounts of each of the terpene compounds present in the sample and the total terpene content are indicated.

Example 9

Chemical Profiling of *Cannabis* Strain Terpin Gorilla

This Example describes the terpene profile of a sample derived from the cannabis strain "Terpin Gorilla". Flower tissues were used. The analytical assay was GC/FID with Headspace Analyzer.

FIG. 8 provides an exemplary terpene profile of a plant sample derived from the cannabis strain "Terpin Gorilla." The specific amounts of each of the terpene compounds present in the sample and the total terpene content are indicated.

Example 10

Chemical Profiling of *Cannabis* Strain "Strawberry AK"

This Example describes the terpene profile of a sample derived from the cannabis strain "Strawberry AK". Flower tissues were used. The analytical assay was GC/FID with Headspace Analyzer.

FIG. 9 provides an exemplary terpene profile of a plant sample derived from the cannabis strain "Strawberry AK." The specific amounts of each of the terpene compounds present in the sample and the total terpene content are indicated.

Example 11

Chemical Profiling of *Cannabis* Strain "Sour AK"

This Example describes the terpene profile of a sample derived from the cannabis strain "Sour AK". Flower tissues were used. The analytical assay was GC/FID with Headspace Analyzer.

FIG. 10 provides an exemplary terpene profile of a plant sample derived from the cannabis strain "Sour AK." The specific amounts of each of the terpene compounds present in the sample and the total terpene content are indicated.

Example 12

Chemical Profiling of *Cannabis* Strain "Pineapple Xpress"

This Example describes the terpene profile of a sample derived from the cannabis strain "Pineapple Xpress". Flower tissues were used. The analytical assay was GC/FID with Headspace Analyzer.

FIG. 11 provides an exemplary terpene profile of a plant sample derived from the cannabis strain "Pineapple Xpress." The specific amounts of each of the terpene compounds present in the sample and the total terpene content are indicated.

Example 13

Chemical Profiling of *Cannabis* Strain "TT JetFuel"

This Example describes the terpene profile of a sample derived from the cannabis strain "TT JetFuel". A concentrate from alcohol extraction was used. The analytical assay was GC/FID with Headspace Analyzer.

FIG. 12 provides an exemplary terpene profile of a plant sample derived from the cannabis strain "TT JetFuel." The specific amounts of each of the terpene compounds present in the sample and the total terpene content are indicated.

Example 15

Enriched Terpene Formulations

A number of enriched, non-naturally occurring terpene-based compositions were prepared. These formulations were derived from cannabis extracts through fractional distillation produced fractions, which were enriched (80% or greater) for a specific terpene. The MCT included in the formulations described in this example was derived from cannabis seed oil and enriched/purified to produce a fraction (80% or greater) caprylic acid. The specific terpene compounds present in each of Formulations 1-4 and their respective concentrations are described below.

FORMULATION 1: Enriched "Keep Tahoe OG". A terpene mixture with specific terpene compounds was prepared. The specific terpenes in the terpene mixture and respective concentrations are shown below.

| Compound | Amount (%) |
|---|---|
| Myrcene | 15.0% |
| Caryophyllene | 35.0% |
| α-Pinene | 12.0% |
| Linalool | 15.0% |
| Lime Oil | 15.0% |
| Limonene | 5.0% |

Final concentrations of the terpene mixture and enhancer (MCT) in FORMULATION 1 were 25% of terpene mixture and 75% of enhancer (MCT).

FORMULATION 2: Enriched "A Kalashnikova vTT1.0". A terpene mixture with specific terpene compounds was prepared. The specific terpenes in the terpene mixture and respective concentrations are shown below.

| Compound | Amount (%) |
|---|---|
| Myrcene | 45.0% |
| Caryophyllene | 20.0% |
| α-Pinene | 20.0% |
| Linalool | 10.0% |
| Lime Oil | 5.0% |

Final concentrations of the terpene mixture and enhancer (MCT) in FORMULATION 2 were 25% of terpene mixture and 75% of enhancer (MCT).

FORMULATION 3: Enriched "Terpin Gorilla". A terpene mixture with specific terpene compounds was prepared. The specific terpenes in the terpene mixture and respective concentrations are shown below.

| Compound | Amount (%) |
|---|---|
| Myrcene | 15% |
| Caryophyllene | 30% |
| α-Pinene | 35% |
| Lime Oil | 5% |
| β-Pinene | 15% |

Final concentrations of the terpene mixture and enhancer (MCT) in FORMULATION 3 were 50% of terpene mixture PineneMix and 50% of a cannabis extract.

FORMULATION 4: Enriched "ACDCvTT1.0". A terpene mixture with specific terpene compounds was prepared. The specific terpenes in the terpene mixture and respective concentrations are shown below.

| Compound | Amount (%) |
|---|---|
| Myrcene | 75.0% |
| Caryophyllene | 10.0% |
| α-Pinene | 10.0% |
| Linalool | 5.0% |

Final concentrations of the terpene mixture and enhancer (MCT) in FORMULATION 4 were 25% of terpene mixture and 75% of enhancer (MCT). The MCT used in this formulation is caprylic MCT.

What is claimed is:

1. A non-naturally occurring composition for administration to a subject, said composition comprising one or more cannabis terpenes and a medium-chain triglyceride (MCT), wherein the medium chain triglyceride comprises at least one medium-chain fatty acid selected from the group consisting of caproic acid (hexanoic acid), caprylic acid (ocanoic acid), capric acid (decanoic acid), and lauric acid (dodecanoic acid).

2. The composition of claim 1, wherein said composition is formulated for administration to said subject orally, transdermally, topically, or parenterally.

3. The composition of claim 1, wherein said composition is formulated into a form selected from the group consisting of a liquid, a tablet, a vaporizer inhalant, a capsule, a gel, a powder, an oral spray, a chewable gum, a sublingual film or lozenge, and a transdermal patch.

4. The composition of claim 1, wherein the MCT comprises at least one medium-chain fatty acid having an aliphatic tail of 6-12 carbon atoms.

5. The composition of claim 1, wherein the medium-chain fatty acid comprises caprylic acid.

6. The composition of claim 1, wherein the ratio of the MCT amount to the amount of the at least one terpene compound is from about 100:1 to about 3:1 by volume.

7. The composition of claim 1, wherein the composition comprises at least one terpene compound selected from the group consisting of monoterpenes, diterpenes, triterpenes, hemiterpenes, sesquiterpenes, sesterterpenes, sesquarterpenes, and notisoprenoids.

8. The composition of claim 1, wherein the composition comprises at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpinolene, terpinene, terpineol, and valencene.

9. The composition of claim 1, wherein the one or more cannabis terpenes at least one terpene compound selected from the group consisting of caryophyllene, limonene, linalool, myrcene, α-pinene, and β-pinene.

10. The composition of claim 1, wherein said composition further comprises an essential oil.

11. The composition of claim 1, wherein the composition further comprises a plurality of chemical compounds which are known to occur in a cannabis strain, wherein the amounts of said plurality of chemical compounds, including said one or more cannabis terpenes with respect to one another in said composition, are about the same as the amounts of said plurality of chemical compounds with respect to one another in said cannabis strain.

12. The composition of claim 11, wherein the plurality of chemical compounds are selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements.

13. The composition of claim 11, wherein said plurality of chemical compounds comprises one or more cannabinoid compound.

14. The composition of claim 13, wherein the one or more cannabinoid compounds are selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), and active analogues and derivatives of any one thereof.

15. The composition of claim 10, wherein the one or more cannabinoid compounds are selected from the group consisting of Δ(9)-tetrahydrocannabinolic acid (Δ(9)-THCA), Δ(9)-cannabidiolic acid (Δ(9)-CBDA), and active analogues and derivatives of any one thereof.

* * * * *

SEQUENCE LISTING

```
<160> NUMBER OF SEQ ID NOS: 34

<210> SEQ ID NO 1
<211> LENGTH: 276
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3372906, library_id:2654

<400> SEQUENCE: 1

atgcttctcg caatatattc ccaccgatgt aacaagtcta aaacttaccc tcaaaacaac      60

caattgtata tgtctgtcct aaattcgaca atacacaatc ttagattcac ctttgacaca     120

accccaaaac cacttgttat cgtcactcct tcacatgtct cccatatcca aggcactatt     180

ctatgtccaa gaaaattggt ttgcaaattc aaactcgaaa cggtggtcat gattctgaag     240

gcatgtccca catatctcaa gtcccatttg ttatag                               276


<210> SEQ ID NO 2
<211> LENGTH: 1638
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3373261, library_id:2654

<400> SEQUENCE: 2

atgaattgct cagcattttc cttttggttt gtttgcaaaa taatattttt ctttctctca      60

ttccatatcc aaatttcaat agctaatcct cgagaaaact tccttaaatg cttctcaaaa     120

catattccca acaatgtagc aaatccaaaa ctcgtataca ctcaacacga ccaattgtat     180

atgtctatcc tgaattcgac aatacaaaat cttagattca tctctgatac aaccccaaaa     240

ccactcgtta ttgtcactcc ttcaaataac tcccatatcc aagcaactat tttatgctct     300

aagaaagttg gcttgcagat tcgaactcga agcggtggcc atgatgctga gggtatgtcc     360

tacatatctc aagtcccatt tgttgtagta gacttgagaa acatgcattc gatcaaaata     420

gatgttcata gccaaactgc gtgggttgaa gccggagcta cccttggaga agtttattat     480

tggatcaatg agaagaatga gaatcttagt tttcctggtg ggtattgccc tactgttggc     540

gtaggtggac actttagtgg aggaggctat ggagcattga tgcgaaatta tggccttgcg     600

gctgataata ttattgatgc acacttagtc aatgttgatg gaaaagttct agatcgaaaa     660

tccatgggag aagatctgtt ttgggctata cgtggtggtg gaggagaaaa ctttggaatc     720
```

```
attgcagcat ggaaaatcaa actggttgct gtcccatcaa agtctactat attcagtgtt    780

aaaaagaaca tggagataca tgggcttgtc aagttattta acaaatggca aaatattgct    840

tacaagtatg acaaagattt agtactcatg actcacttca taacaaagaa tattacagat    900

aatcatggga agaataagac tacagtacat ggttacttct cttcaatttt tcatggtgga    960

gtggatagtc tagtcgactt gatgaacaag agctttcgtg agttgggtat taaaaaaact   1020

gattgcaaag aatttagctg gattgataca accatcttct acagtggtgt tgtaaatttt   1080

aacactgcta attttaaaaa ggaaattttg cttgatagat cagctgggaa gaagacggct   1140

ttctcaatta agttagacta tgttaagaaa ccaattccag aaactgcaat ggtcaaaatt   1200

ttggaaaaat tatatgaaga agatgtagga gctgggatgt atgtgttgta cccttacggt   1260

ggtataatgg aggagatttc agaatcagca attccattcc ctcatcgagc tggaataatg   1320

tatgaacttt ggtacactgc ttcctgggag aagcaagaag ataatgaaaa gcatataaac   1380

tgggttcgaa gtgtttataa ttttacgact ccttatgtgt cccaaaatcc aagattggcg   1440

tatctcaatt atagggacct tgatttagga aaaactaatc atgcgagtcc taataattac   1500

acacaagcac gtatttgggg tgaaaagtat tttggtaaaa attttaacag gttagttaag   1560

gtgaaaacta aagttgatcc caataatttt tttagaaacg aacaaagtat cccacctctt   1620

ccaccgcatc atcattaa                                                 1638
```

```
<210> SEQ ID NO 3
<211> LENGTH: 1617
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3373508, library_id:2654

<400> SEQUENCE: 3

atgaagtact acttagcttt cttttcattg ttatcttttt gcattatagt tactaatgct     60

tctcaaccac atgaggactt ccttcaatgt ttgtcccaca atatctcaaa cacaaccact    120

ttggctgaac tcacatacac tcgaaacgac tcgtcgttta tctctgtaat gagctccaac    180

atacaaaacc taagattttc cttcccttca actccaaaac cactcgttat cgttacacct    240

tcaaacgcct cccatgtcca agcctctgtc tactgctcaa agatacatgg gttagagatc    300

cgaacacgaa gcggtggcca tgatttcgaa ggcctctctt acgtttctga agtcccattt    360

gtcataatag acttgagaaa cctaagttct atcaacgtaa acgtggatga aaaaactgct    420

tgggttgaag ccggagctac cattggtgaa gtttattata ggattgccga gaaaagtcga    480

aatctcggct ttcctgctgg attttgccct acggtaggcg ttggtggaca ctttagtgga    540

ggtggctatg gacctttggt gcgaaaatat ggcctagcag ctgataatat cattgatgct    600

tacattgtta atgttgatgg gaaaattctt gatcgagaat caatgggggga ggatttgttt    660

tgggccatac gtggtggtgg agcagcaagc tttggaatcg ttctcgcttg gaaaatcaga    720

ttggttcctg tcccatcaac agtgacaaca ttcattgtta atagggattt gggccaaaat    780

gagaccatga agcttgtgaa caagtggcaa tacattgctg ataagttgga tgatgatttg    840

gttatcttaa ttaggttctc gactgtgaat tctacccaaa ataataaggt tatactccaa    900

gctcaattct tgtcattgtt tcttggtgga gtggataatc ttctttcatt aatggaaaag    960

agttttcctg agtttggttt gaaaagagaa gattgcaatg aaatgagctg gattgagtct   1020
```

```
gtttcttatt ttgctggatt ccctattgga gctgagatgg aaaacttgct taatagaact   1080

caacaatggt tgttttcatt caaaggtaaa cttgactacg tgaagaaaac tataccagaa   1140

aatgtattga aaacaatgct tgaaaagtta tatgaagaag atgttggagt gggattcttt   1200

cagttgtttc cttatggtgg gaaaatgaat gagatttctg aatcagagat tccattctcc   1260

catagagccg gaaacctcta caaaattctc tactatgctc aatgggttca gaaaccagga   1320

gatgatgatg atgatgatgg gagtatcaat tggcctagaa gtgtttacaa gtacatgact   1380

ccttatgtgt ccaaaagccc aagaagtgca tatgtaaact atcgagatct tgacttgggt   1440

aaaaataacg acaagggacc cacgagttac acacaagcaa gtatttgggg tagaaagtat   1500

ttcgggaaag acaatttcaa gaggttagtt catgtgaaga ctaaagttga tccccaaaat   1560

ttcttcagga atgaacagag cattccacct cttccactac cactgccaag tccataa      1617
```

<210> SEQ ID NO 4
<211> LENGTH: 1233
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3373607, _id:2654

<400> SEQUENCE: 4

```
atgagaaatc tacgttcaat cactgtagac gtagatacca aaactgcatg ggttgaagct     60

ggagctacca ttggtgaact ttattatagg attgctgaga aaaatgggaa tctgagtttt    120

cctgctgggt actgtcgtac tgttggggta ggtgggcatt tcagtggagg aggctatgga    180

gcactgttgc gaaaatatgg ccttgcagct gataatatca ttgatgctca cttagtcaac    240

gcagatggag aattccttga ccgaaaatct atgggagaag atttgttttg ggccatacgt    300

ggtggtggtg gagcaagctt tggaatcatt ctcgcttgga aaatcagatt ggttgcagtt    360

ccatctaaag ttactatgtt ctctgttagt aaaaacttgg agatgaatga gactgtgaag    420

atatataaca aatggcaaaa tactgcttac aagtttgaca aagatttgtt actctttgtt    480

agcttcatga ctattaattc taccgattca caagggaaat acaagacaac tatacaagct    540

tcattctctt ctatatttct tggtagggtt gagagtctcc tcatattgat gcaaaagaaa    600

tttcctgagt tgggaattga aagaaaagat tgcctcgaaa agagctggat tgaaactgtc    660

gtttactttg atggtttttc aagtggggat acaccagaat ctttacttaa tacaacattt    720

caacaaaatg tatttttcaa ggtgaaatta gactatgtaa agaagccagt tccagaagtt    780

gtgatggtaa aacttttgga gaagttatat gaagaagatg taggtgtggg gtttcttatg    840

atgtaccctt atggtggtaa aatggatgag atttcagaat cagcaattcc attccctcat    900

cgagctggat ttatgtacaa aattttgtac ttgtctgcat gggagaaaga aggagaaagt    960

gaaaagcata tgaattgggt ccgaagtgca tataatttca tgtctcctta tgtgtctcaa   1020

aatccaagag ctacatatct caattatagg gaccttgatt tgggaacaaa taacgagaag   1080

ggtcctatta gttactcaca agcaagtgtt tggggtaaaa agtatttcgg tatgaacttt   1140

aagaggttag ttaatgtgaa aaccaaggtc gatccaagta atttctttag aaacgaacaa   1200

agcatcccac cacttctgtc gcgacgcctc taa                                1233
```

<210> SEQ ID NO 5

<211> LENGTH: 1171
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3375323, library_id:2654

<400> SEQUENCE: 5

```
atgagaaatc tacgttcaat cactgtagac gtagataaca aaactgcatg ggttgaatct     60

ggagctaccc ttggagaact ttattatagg attgctgaga aaaatgagaa tcttagtttt    120

cctggtggct attgccatag tgttggggtt ggtgggcatt tcagtggagg aggctatgga    180

gcattgatgc gaaaatatgg ccttgcagct gataatgtca ttgatgctca cttagtcaac    240

gctgatggag aattcgttga ccgaaaatct atgggagaag atttgttttg ggccattcgt    300

ggtggtggtg gagcaagctt tggaattgtt cttgcttgga aattagatt ggttcctgtg     360

ccatctaagg ttactgtatt atcagttagt aagaacttgc cgataaatga aactgtgaaa    420

atttataata agtggcaaaa tattgctcac aagtttgacc aagatttgtt gatggtagtt    480

aggttcttaa ctgtgaattc tactgatgag catgggaaga atatgacaac aatacaagct    540

acattctttt ctatttttct tggtagagtg gataattttc tttccttgat gcaaactaac    600

tttcctgagt tgggtgtagt aagaaaagat tgttttgaaa cgagttggat tgaaatgatc    660

tttttcttca atgaattctc aagtgaggat aaattggagg ttttgctcga tccaacaaat    720

gtagtaaagg gttatttcaa ggggaaactg gactacgtta ggaagccaat ttcagaaatt    780

gttatggtca aacttttgga aaagttatat gaagaagatg taggattggc atatattcaa    840

atgtaccctt atggtggtaa aatgagcgag attcctgaat ctgcaattcc attcccacat    900

agagctggag ttatgtacaa aattttatat tggtctcagt gggaaaaaga agaagaaagt    960

gaaaggcata cgaatcgggt tcgaagtgtt tataattaca tgactccata cgtgtccgaa   1020

aatccaagag cttcatatat taattataga gacctagatt tgggaacaaa taatgaaaaa   1080

ggtcctataa gttatgaaca agcaagcatt tgggggaaaa agtacttcaa taaaaatttt   1140

aagaaattag ttcaagtgaa aaccaaggtt g                                  1171
```

<210> SEQ ID NO 6
<211> LENGTH: 957
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3376354, library_id:2654

<400> SEQUENCE: 6

```
atgcgaaatt atggcctcgc ggctgataat atcattgatg cgcacttagt caatgttgat     60

ggaaaagttt tagatcgaaa atccatgggg gaagatttgt tttgggctat acgtggtggt    120

ggaggagaaa actttggaat cattgtagcg tggaaaatta gacttgttgc tgtcccatca    180

atgtctacta tattcagtgt taaaaagaac atggagatac atgagcttgt caagttagtt    240

aacaaatggc aaaatattgc ttacatgtat gaaaaagaat tattactctt tactcacttt    300

ataaccagga atattacaga taatcaaggg aagaataaga caacaataca cagttacttc    360

tcctccattt tccatggtgg agtggatagt gtagtcgact tgatgaacaa gagctttcct    420
```

```
gaattgggta ttaaaaaaat agattgcaaa cagttgagct ggattgatac tatcatcttc    480

tacagtggtc ttgtaaatta caacacaact aattttaaaa aagaaatttt gcttgataga    540

tcaggtgggc ggaaggcggc tttctcgatt aagttagact atgttaagaa accgattcca    600

gaaaccgcaa tggtcacaat tttggaaaaa ttatatgaag aagatgtagg agttgggatg    660

tttgtgtttt acccttatgg tggtataatg gatgagattt cagaatcagc aattccattc    720

cctcatcgag ctggaatcat gtatgaaatt tggtacatag cttcatggga gaagcaagaa    780

gataatgaaa agcatataaa ctggattcgg aatgtttata atttcacgac tccttatgtg    840

tcccaaaatc caagaatggc gtatctcaat tatagggacc ttgatttagg aaaaactaat    900

tttgagagac ctaataatta cacacaagca cgtatttggg gtgaaaagta ttttggt       957
```

<210> SEQ ID NO 7
<211> LENGTH: 483
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3378841, library_id:2654

<400> SEQUENCE: 7

```
atgaagtact caacattctg gtatgtttgc aagataatat tttttttct ctcattcaat     60

atccaaattt caatagctaa tcctcaagaa aacttcctta aatgcttctc acaatatatt    120

cccaccaatg taacaaatgc aaaactcgta tacactcaac acgaccaatt ttatatgtct    180

atcctaaatt cgaccataca aaatcttaga tttacctctg acacaacccc aaaaccactt    240

gttatcatca ctcctttaaa tgtctcccat atccaaggca ctattctatg ctccaaaaaa    300

gttggcttgc agattcgaac tcgaagcggt ggtcatgatg ctgagggcat gtcctacata    360

tctcaagtcc catttgttat agtagacttg agaaacatgc attcggtcaa aatagatgtt    420

catagccaaa ctgcatgggt tgaagccgga gctacccttg gagaagttta ttattggatc    480

aat                                                                  483
```

<210> SEQ ID NO 8
<211> LENGTH: 1143
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3379537, library_id:2654

<400> SEQUENCE: 8

```
atgtctgtcc tgaatttgac aatacaaaat cttagattta cctctgatac aaccccaaaa     60

ccactcgtta ttgtcactcc ttcaaatgtc tcccatatcc aagccactat tctatgctcc    120

aagaaagtgg gcttgcaaat tcgaactcga agcggtggcc atgatgctga gggtttgtcc    180

tacacatctc aagtcccatt tgttatagta gacttgagaa acatgcattc ggtgaaaata    240

gatattcgta gccaaattgc gtgggttgaa gccggagcta cccttggaga agtttattat    300

tggattaatg agaatcttag ttttcctggt gggtattgcc ctactgttgg cgtaggtgga    360

cactttagtg gaggaggcta tagagcatta atgcgaaatt atggcctcgc agctgataat    420
```

-continued

```
atcattgatg cacacttagt caatgttgat ggaaaagttc tagatcgaaa atccatgggg    480

gaagatctat tttgggctat acgtggtggt ggaggtgaaa actttggaat cattgcagcg    540

tggaaaatta gactggttgc tgtcccatca agggctacta tattcagtgt taaaaggaat    600

atggagatac atgggcttgt caagttattt aataaatggc aaaatattgc ttacaagtat    660

gacaaagatt tattactcat gactcacttc ataaccagga atattataga taatcaagga    720

aagaataaga ctacagtaca cggttacttc tcttgcattt tccatggtgg agtagatagt    780

ctagtcaact tgatgaacaa gagctttcct gagttgggta ttaaaaaaac tgattgcaaa    840

gaattgagct ggattgatac taccatcttc tacagtggtg ttgtaaatta taacactact    900

aattttcaaa aggaaatttt gcttgataga tcagctgggc agaaagtagc tttctcagtt    960

aagttagact acgttaagaa accaattcca gaaactgcaa ttgtcaaaat tttggagaaa   1020

ttgtatgaag aagatgtagg agttggggtg tatgtattgt acccttacgg tggtataatg   1080

gacaagatct cagaatcaac aattcctttc cctcatcgag ctggaatcat gtacgaagtt   1140

tga                                                                 1143
```

```
<210> SEQ ID NO 9
<211> LENGTH: 477
<212> TYPE: DNA
<213> ORGANISM: Cannabis sp.
<220> FEATURE:
<223> OTHER INFORMATION: Tetrahydrocannabinolic acid synthase
<220> FEATURE:
<221> NAME/KEY: misc_feature
<222> LOCATION: (0)...(0)
<223> OTHER INFORMATION: EST marker PE2EUKC3383039, library_id:2654

<400> SEQUENCE: 9

atgaagtact caacattctc tttttggttt ctttgcaaaa tattagtttc acttctctca     60

ttctctatcc aaacttctcg agctaatcca catgacaact ttcttcaatg cttctccaaa    120

catatcaaca acaataacaa taaatcaatt gtaaaagtca tacacactcc aaatgatcca    180

tcatatatct ctgtcctaaa ttcaactata caaaacctta gattcgcttc tccatcaaca    240

ccaaaaccac tagttatcat cacaccttca aatacatccc atgtccaagc ctgtgtttta    300

tgctccaaga aatatggctt gcagattcga actcgaagcg gtggtcatga tgctgagggc    360

atgtcctaca tatctcaagt cccatttgtt atagtagact tgagaaacat gcattcggtc    420

aaaatagatg ttcatagcca aactgcatgg gttgaagccg gagctaccct tggagaa       477
```

```
<210> SEQ ID NO 10
<211> LENGTH: 1470
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3373123, library_id:2654

<400> SEQUENCE: 10

atgtccactc aaatcttagc atcatcatca tcttcaaatg aaaacccaaa taaaattgtt     60

cgtcctacaa aaacatttca tccacatatt tggggagaac aattcttaca ttacaacatt    120

tcagaacaag atttgtattg tcaacaacaa aaggttgagg aattaaagga agtggttaga    180

agagaaatat ttggagaatc atcaatatca tcatcagctt attatgatgc ttggaaaaat    240

caattgaaga taattgatgt ggtagaacgt ttgggattgt cttatcattt tgaaactgaa    300
```

```
atagaaaata tgatagaaca aatctacaac aaaaccaata attttgatct tcttaaggat    360

gaagagttgc atgatgtttc cttgtgggtt agacttctac gacaacatgg atttagggtt    420

tcttctgata tatttaaaaa attcaaagat gaggatggaa actttaaaaa atgtttggta    480

agtgatactc ttggtttgct tagcttatat gaagcctcac atttgagttg tggtggagaa    540

aatatacttg atgaagcact tgctttcaca acaacacacc taaatgagtt tttggcgaag    600

aaaaaagaac accatgatga cgatgatcca ttatcgaaag aaatatatcg tgccctagag    660

aggcccttaa gaaagaccct agtgaatctc catgcaaggt atttcatttc aatatatgaa    720

aaagatgcct cacataacaa agtattgcta caacttgcaa agttagattt taatctatta    780

caatccctac acaaaaagga gcttagtgaa atcagcaggt ggtggaaaga atcaaacttt    840

gtacaaaaat tccctttttgc aagagataga attgtggagc tctatctttg gatgttagga    900

gtctattatg aaccccaata ctctttggca agaaatattt tagccaaaat catagctttt    960

tcctcaattg ctgatgatat ttatgatgca tatggaacat ttgaagaact tgaactccta   1020

actcaagcaa ttgaaaggtg ggatataaat tgtattgata cactcaatca agaatatttg   1080

aaaacatttt ataaggatct tttgaattgt tatgaagagt ttgagcaagt gcttacaaaa   1140

gaagaaactt atagagttca ttatgcaaaa gaagtgttta aagagttaat ccgatcatat   1200

tttgatgaag ctcgatggtt gaatagtgga cgtgtcccaa attttgaaga gtacatggaa   1260

tttgcaacca ttaattgtgg ttactatatg ttgatagtga gttctttggt tggaatgaaa   1320

acaagtattg taaccaaaga tgtttttgag tggctctcca aagatcgaaa gattattaga   1380

gcatctgtta ttatttgtag gctcatggat gacatagctg aacacaaggt aagaaaatca   1440

tcaaccacac aaacttatgt accattttag                                    1470
```

<210> SEQ ID NO 11
<211> LENGTH: 2364
<212> TYPE: DNA
<213> ORGANISM: Cannabis sp.
<220> FEATURE:
<223> OTHER INFORMATION: Ent-kaurene synthase B, chloroplast
<220> FEATURE:
<221> NAME/KEY: misc_feature
<222> LOCATION: (0)...(0)
<223> OTHER INFORMATION: EST marker PE2EUKC3373262, library_id:2654

<400> SEQUENCE: 11

```
atgtctcatt cattgcattc caacattagg tgctcctctt cttcttcctc atcagcttct     60

cccataccaa gactaaatgg aacaagtaaa agcaacatag ctgttttgaa gtttgaggag    120

accaaagaga gaataaagaa gatgttcaat aatgttgaac tctctgtctc gtcttatgac    180

actgcctggg tggcaatgat cccttcaaat tctgggcatc accctttctt tcctcaatgt    240

gtaaattggt tactagagaa tcagcactct gacggttcat ggggtcttcc tcatcgtcat    300

cccttgctta tgaaagatgc tcttttatct actttaacta gtgtacttgc aatgaagcga    360

tggggtgttg gcgaagaaca aatagacaag ggcttgtctt tcatagagga aaatatagct    420

tcagccattg atgagaagca atgttcacct attggatttg aagtaatatt tcctacaatg    480

attgattatg ccaaaaaatc agatctgaat attactcttg agccatccaa tcataatgac    540

ctagttcata acagaaaggt ttcacttgaa agagcctcag gaagctactc agagggtcat    600

gaagcatact tagtgtacat ttcagaaggt cttggaaagc cactggattg tgaaagagtc    660

tttaagtacc aaagaaaaaa tggttctctg tttaattctc catccaccac agctgttgct    720
```

```
tttacaaacc atgggaatgc tgactgtctt aagtatctct gctctgttgt agacaagttt    780

ggaagtgcag ttccaacagt atatcctcta gatatttatg ctcgtctctc aatggtggac    840

aatctccaaa ggttggggat agaacgattt ttcaaagagg aaatcagaag tgtactggat    900

gaaacataca aatattggct gcaaggagag gagtgtgttc tcttagatgc ttccacctgt    960

gcaatggcat ttcgtttatt gcgtgttaat ggatatgatg tctcttcaga tccattagtt   1020

cgattttcag aagattatat attcaattac cttggaaatc atacgaagga tatagatgct   1080

atcttggaaa tatttagagc atccgagatc atcatacacc caaatgaatc aatcttggag   1140

aagcaaaatt tctgtacaag tcattttcta gaacaagagt tattcagcat ttcaactagg   1200

ggagataaac tcaataaaaa tattggcaaa gtggtaagtg aagctcttaa gattcctttc   1260

tatgcaaact tggaacgact agcaagtaga agagccatag agtactatga cactgatagt   1320

acgaggattc tgaaaacttc atattgttcc tcaaatgttc ggagcaagga tttcctaata   1380

ttagcagttg aagacttcaa catgtgccaa tcaatacacc gtgaagaact caaaattctt   1440

tctaggtggg ttgtagagaa taggttggac aagctaaagt ttgctaggca gaagctggca   1500

tactgttact tttctgctgc tgctactctt tcttctcctg aattatctga tgcccgtata   1560

tcatgggcga aaaatggggt acttactaca gtggttgatg attttttga tgttggaggt   1620

tcagaagagg aactagtaaa cctcattcaa ttgttggaaa agtgggatgt agatgtcagt   1680

gttgattgtt tatcggagca agttgaaatt atttatttag cacttcatgg cacaatctct   1740

gaaattggag aaaaggcgtt cgtgtggcaa ggacgtagtg tgacaaatca cataatagag   1800

atttggctgg atttgctcaa gtctatgttg aaggaagctc aatggttgaa atacgagacc   1860

gtcccaacaa tagatgagta tatgaaaaat ggatacatat catttgcctt aggacctata   1920

gtccttccag cactttactt agttggacct atgctttctg aggatgttac aagacatcct   1980

gagctccatt atctatataa actcatgagc acttccggac gacttctcaa cgatatccac   2040

ggcttcaaga gagaatccaa agaagggaaa ctgaatatag tgtcattaag cctactggcg   2100

cgtggttttg gctctggttc ttcttctgaa gaagagatca ttaatgaaat gaaaagtgtt   2160

gtaaatggta agaggagaga attgctgagg ctagttttta aggaaaaaga tagcattgtt   2220

ccaagagctt gcaaggactt gttctggaaa atgagccaag tgttgcacct attttatgcc   2280

aatgacgacg gattcacctc aaatgagatg atcaatgtcg caaaagcaat aatcgaggag   2340

cccataattg aaaataaatt gtaa                                          2364
```

<210> SEQ ID NO 12
<211> LENGTH: 1572
<212> TYPE: DNA
<213> ORGANISM: Cannabis sp.
<220> FEATURE:
<223> OTHER INFORMATION: Beta myrcene/limonene synthase
<220> FEATURE:
<221> NAME/KEY: misc_feature
<222> LOCATION: (0)...(0)
<223> OTHER INFORMATION: EST marker PE2EUKC3373344, library_id:2654

<400> SEQUENCE: 12

```
atggtccttg gactggaaat taactcttta gccctacttg agctaattga tacattgcaa     60

aggcttggaa tatcttacca ttttaagaat gaaataaaca ctattttgaa gaaaaaatac    120

actgataatt atattaacaa taatattatt attactaacc ctaattataa taatttatat    180

gccattgctc tcgaatttag gcttctacgc caacatggct atacagtacc tcaagaaatt    240

tttaatgctt tcaaggataa gagagggaaa tttaaaacat gcttgagtga tgatattatg    300
```

```
ggagtattgt gtttatatga agcttcattc tatgctatga aacatgaaaa tattttggag    360

gaagcaagaa ttttttcaac taaatgtctt aaaaaataca tggagaaaat ggagaatgag    420

gaagagaaaa aaatattatt attagatgat aataatatta atagtaattt gctattaatt    480

aatcacgctt tcgagcttcc gcttcattgg agaataacaa gatcggaagc taggtggttc    540

attgacgaaa tatatgagaa aaaacaagac atgaattcga ctttgttcga gtttgcgaaa    600

ttagatttta atatagtgca atcaacacac caagaagatt tacaacattt atcgaggtgg    660

tggagggatt gtaaacttgg tgggaaattg aattttgcta gagatagatt gatggaagct    720

ttcttatggg atgttggact aaaattcgag ggagaattca gctattttag aagaataaat    780

gcaagattat ttgtgcttat aacaataatt gatgatattt atgatgtata tggaactttg    840

gaggaattag agcttttcac tagtgctgtt gaaagatggg atgtgaaatt aatcaatgag    900

ttaccagatt acatgaagat gcctttcttt gttttacaca ataccataaa tgagatgggg    960

ttcgatgtat tagtacaaca aaactttgtc aacattgaat accttaagaa atcgtgggta   1020

gatttatgta aatgttattt acaagaagca aaatggtatt atagtggata ccaaccaaca   1080

ttggaagaat acactgagtt gggttggctt tcaataggag catcagtaat tcttatgcat   1140

gcttattttt gtttcacaaa tcctataaca aaacaagact tgaaaagttt gcaattgcaa   1200

catcattatc ccaacataat taaacaagca tgcttgatta caaggcttgc agatgattta   1260

ggaacatctt cggatgaatt gaatagaggc gacgttccta aatcgattca atgttacatg   1320

tacgataata atgctaccga agacgaagct cgtgaacaca tcaagttctt gataagtgaa   1380

acatggaagg atatgaataa gaaagatgaa gatgagagtt gtttatcaga aaattttgtt   1440

gaagtttgca aaaatatggc tagaacagca ctattcatat atgagaatgg agatggacat   1500

ggttctcaga atagtttatc aaaagaacgt atttcaacct tgattattac tccaattaat   1560

attcctaaat aa                                                       1572
```

<210> SEQ ID NO 13
<211> LENGTH: 1734
<212> TYPE: DNA
<213> ORGANISM: Cannabis sp.
<220> FEATURE:
<223> OTHER INFORMATION: ( )-limonene synthase 2
<220> FEATURE:
<221> NAME/KEY: misc_feature
<222> LOCATION: (0)...(0)
<223> OTHER INFORMATION: EST marker PE2EUKC3373785, library_id:2654

<400> SEQUENCE: 13

```
atggtcaata gtacaaatat tactaataat actactatat ttgataatca tattcataga     60

agatcagcca attatgaacc tcccatttgg tcttttgatt acattcaatc tctttcatca    120

agccaatata agggagaaac atgtacaagt agattgaatg agctagaggc aaatgtgaaa    180

gagatattgt tagttgagat gaaatctaac tctttagctc aacttgagtt tattgatgca    240

ttgcaaagac ttggattatc ttaccgtttc gagactgaaa taaacactat tttaaatgaa    300

aagtactccg gtaatattat cgataaccct aattataatt tgtacgccac agctctcgaa    360

ttcaggcttc tacgccatca tggttatgat gtatctcaag aaattttcaa tgtgtttaag    420

gatgagatta caagcaagtt caaggcaaga acgagtggcg aagatataat tggagtattg    480

gctttatacg aagcttcatt ctatggcaaa aaaagtgaaa gtattttgga agaagctagg    540

gtttcctcaa tcgaatgtct cgaaaattac gtagcaacta tgacgatgga gcgaaacaaa    600
```

```
ccatcattat tagtcaatga ttatgatgat gataataata tgttattatt agtgaatcat    660
gccttggagc ttccacttta ttggagaata acaagatcag aagcaaggtg gttcattgat    720
ttatatgaaa aaaatcataa catgaattct actttgcttg aatttgccaa attggattac    780
aacatggtac aatccatata tcaagaagat ctaaaacatc tctcaaggtg gtggagccat    840
acaaaacttg gagagaaaat ggatttcttt agagatagat taatggagtg tttcttatgg    900
actgtgggaa tagcatgtga gccagaaaaa agctattata gaagaatgtc tggaagatta    960
tatgttctaa taacaacaat tgatgatata tatgatgttt atggaacatt ggaggaatta   1020
gagcttttca ctaatgcagt tgagagatgg gatgtgaaag caatggatga tttaccagaa   1080
tatatgagga tgcctttctt tcttttacac aataccataa acgaaatggc tttcgatgtg   1140
ttaggacacc aaaatttcct caacgttaaa ttccttaaga ggacgtgggt agatttctgt   1200
aaacatcaat tacaagaggc aaaatggttt cacagtggat acaaaccaac attcgaagaa   1260
tacattaaca atgcatggat ttcggtatca ggaccgatta ttcttatgga tgcttatttc   1320
tctcttacaa atcctgttac aaaagatgcc ataaatttac tggaattagg ttatccaccc   1380
ataatttacc atgcatccat gattctacga cttacagatg atctaggaac atcgaatgat   1440
gaaatgaaaa gaggtgatat tccgaaatca attcaatgtt acatgaacga tacaggtgtt   1500
tctgaagatg aagctcgaga tcatatgaag tttctaataa gtgaattatg gaaggaaata   1560
aataatgaag atgaaaatat ggactctcct ttctcaaaac aatttcttca aaattgtaaa   1620
aatcttgcta gaatatcaca atttatatat caatatggag atggacatgc ttctcaggat   1680
agtttatcaa aacaaagaat ttcagaattg ataattaatc atattccttc ttaa         1734
```

```
<210> SEQ ID NO 14
<211> LENGTH: 1600
<212> TYPE: DNA
<213> ORGANISM: Cannabis sp.
<220> FEATURE:
<223> OTHER INFORMATION: P(E)-nerolidol/(E,E)-geranyl linalool synthase
<220> FEATURE:
<221> NAME/KEY: misc_feature
<222> LOCATION: (0)...(0)
<223> OTHER INFORMATION: EST marker PE2EUKC3373853, library_id:2654

<400> SEQUENCE: 14
```

```
atgcatggct acaaagtttt tcctagtaac atctattgga ttttgaagaa tgaagatata     60
aaaaatcaca tagaatcaaa ctatgaatgc ttttcagtta cgatgttgaa tctttacaga    120
gctactgatc ttgcttttca tggtgaattt gagcttgatg aactaagaat attttcgaga    180
aaactacttc aaaagtctat tttagtagga gctcgacata caaatccttt taacaaactg    240
attgagaatg agttgagtct tccatggatg gctcgactag atcacttgga acatagactt    300
tttattgaac aaactaatga agctcaatca tctttatgga tgggaaagac ttctttccaa    360
aggttgtcga ggtttcacaa cgacaaacta gttcgtctag ccaccttaaa ttatgagttc    420
aaacaatcta tttacaagac cgaacttgaa caattaacaa ggtggtgtaa atattgggga    480
cttaatgaaa tgggatttgg tagagaaaaa agtacatact gttattttgc agtagcttca    540
gcttgttgtt ctttgcctta tgattctcca attcgattga tggttgcaaa gggtgctata    600
ataataacaa ttacagatga tttttttgat atgaaagaat ctctaatcac tgagttaaaa    660
acttttacta aggcctttca aaggtgggat ggtaaagagt tgagtggtgt tagtaagaaa    720
atatttgatg ccctagataa tcttgtaagt gaaatggcaa ctatgtacct tgaacaacaa    780
gaaaatagta atcatgacat aaccaattgg ctaagaaaaa tttggtatga aacgatttgt    840
```

```
tcatggctta ctgaatcgga gtggagtaaa aatgggattg taccaaccat ggatgaatat    900
cttaaagttg gaatgacttc catagcaact cacaccttgc ttcttccagc ttcttgtttt    960
gtaataaatt caactttacc ggtctactct caattacgac caattcaatg tgagagtgtt   1020
acaaaactcg tcatgactat ttgtcgtttg ttaaatgact tacaaagtta tgagaaggaa   1080
aaagaagaag gcaaaccaaa ctcaattact gtgtacatga agaacaattc tgaggtagaa   1140
atggaagaag cagtaaagta cgtgaaagag atattaaaca agaagaagaa agagttactc   1200
gaacatgtta tgattgatgg ctttaccaat ctttcaaaag agtgtaggca tctacacctc   1260
tcttgcttaa aagtatttca aatgttcttc aactcttcga atcgatatga ttcagacact   1320
gaaatgcttg aagacattag caaagcaatc tatgttcctt tgaaatcaat tgatcatgaa   1380
ggactcgaaa agaatctctt aaggcctcca aagtcaccga tgattgatct tactcgagtc   1440
aaatcaacga ccacaaaatg ttcgatgaac aagaataaat ttagtcaacc cactaaatgt   1500
tttgtgatca tgaatgaact ttctcttcat aaacataaaa aagttggcaa ttggaaaata   1560
gcgacaccta ttaggccttt acaactcaaa ttatgcctca                         1600
```

```
<210> SEQ ID NO 15
<211> LENGTH: 1647
<212> TYPE: DNA
<213> ORGANISM: Cannabis sp.
<220> FEATURE:
<223> OTHER INFORMATION: (3S)-linalool/(E)-nerolidol /(E,E)-geranyl
      linalool synthase
<220> FEATURE:
<221> NAME/KEY: misc_feature
<222> LOCATION: (0)...(0)
<223> OTHER INFORMATION: EST marker PE2EUKC3373917, library_id:2654

<400> SEQUENCE: 15
```

```
atgtcttctt acgcatcttt tcgtcccttt aaaccctcct catcactttc gagttctcaa     60
aacataatta gaaattttga cgagaactcc aaatatcata tcaggagtaa cggtgatctc    120
acaccacaaa aggatttaga taaatacagg gacgttttaa gaaaagcaga cccatttgat    180
gaaggtctga agatgattga tgctattcaa cggctaggaa ttgactatat cttcgaggaa    240
gagattgata aaattataca aagccagtct gcttataagt tttttagaga attcgaacat    300
gatcatcatc atcaagatct gtatgatgta gctcttcgtt ttcgactctt gagacaacac    360
ggtctcttcg ttcctgctga tattttcaac aagtacaagg acaataataa cggttgtttc    420
gacacgaggc taagagagga catcaagggt ttgctgagct tatatgaagc ctcccatcta    480
tgcatagagg gagaaaatat ccttgatgaa gctgctttat ttagtgctca acacttggaa    540
gcgtccatga cacgtcttca tcgttatgat caatatcagg ccaaatttgt ggcaactaca    600
cttcaaaatc ccactcacaa aagtttatcc aagttcacag ccaaggacct ttttggtgtc    660
tatcccagtg agaatgggta cataaatttg tttcaacaac tagcaaaagt tgaatttaat    720
agagttcagt ccctgcatag aatggaaatt gatcaagtca ccaggtggtg gcgagacatt    780
ggtttagcta aggaattaac tttcgcaaga gatcaaccgg tgaagtggta tatttggtcc    840
atggcctgcc taaccgatcc aaccttgtcg aaacaaaggg ttgcgcttac aaaatccatt    900
tcgtttatct atgtaataga tgatattttc gacatgtaca gttcacttga tgaactcatt    960
ctcttcaccc aggctgtctc tagctgggaa tatagtgcta tacaaaaact tccagactcc   1020
atgaagacat gctttagagc cctagataat atgatcaatg agtctagcca tacgatctat   1080
caaaagcgtg gatggagccc tttacactct cttcggaaga cgtgggcaag tttgtgcgaa   1140
```

```
gcctttttag tagaggcaaa atggtttgca tcaaggcacg taccaaaggc aaaagaatac   1200
ttggaaaatg gtgtggtcag ctcaggagtg cacgtagttc tggttcatat atttgttctc   1260
ttggatgaaa ccagtctcac ccaaaagaca ctggattttg tggaaaacat gccttccatc   1320
attacttcta cagcatcgat tcttaggctt tgggatgact ttggtagtgc caaggatgag   1380
aatcaagaag gacatgacgg atcttatgtg gagtgttaca tgaaggaatt aggaggcagt   1440
gttgaagatg cacgtgagga aatgatggaa aagatttcag atgcatggaa gtgcctcaat   1500
aaagaatgca tacttcgaaa tccagcgttt ccaccaccat tcctcaaagc ttctctcaat   1560
ctcgcaagat tagttccttt gatgtataat tatgatcaca accaacgcct accccacttg   1620
gaagaacata tcaaatcttt gttatag                                       1647
```

<210> SEQ ID NO 16
<211> LENGTH: 1719
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3374045, library_id:2654

<400> SEQUENCE: 16

```
atgtccactc aaatcttagc atcatcatca tcttcaaatg aaaacccaaa taaaattgtt     60
cgtcctacaa aaacatttca tccacatatt tggggagaac aattcttaca ttacaacatt    120
tcagaacaag atttgtattg tcaacaacaa aaggttgagg aattaaagga agtggttaga    180
agagaaatat ttggagaatc atcaatatca tcatcagctt attatgatgc ttggaaaaat    240
caattgaaga taattgatgt ggtagaacgt ttgggattgt cttatcattt tgaaactgaa    300
atagaaaata tgatagaaca aatctacaac aaaaccaata attttgatct tcttaaggat    360
gaagagttgc atgatgtttc cttgtgggtt agacttctac gacaacatgg atttagggtt    420
tcttctgata tatttaaaaa attcaaagat gaggatggaa actttaaaaa atgtttggta    480
agtgatactc ttggtttgct tagcttatat gaagcctcac atttgagttg tggtggagaa    540
aatatacttg atgaagcact tgctttcaca acaacacacc taaatgagtt tttggcgaag    600
aaaaaagaac accatgatga cgatgatcca ttatcgaaag aaatatatcg tgccctagag    660
aggcccttaa gaaagaccct agtgaatctt catactaagc atttcatttc gatatacgaa    720
aaagatgcct cacataacaa agtattgcta caacttgcaa agttagattt taatctatta    780
caatccctac acaaaaagga gcttagtgaa atcagcaggt ggtggaaaga atcaaacttt    840
gtacaaaaat tccctttttgc aagagataga attgtggagc tctatctttg gatgttagga    900
gtctattatg aaccccaata ctctttggca agaaatattt tagccaaaat catagctttt    960
tcctcaattg ctgatgatat ttatgatgca tatggaacat ttgaagaact tgaactccta   1020
actcaagcaa ttgaaaggtg ggatataaat tgtattgata cactcaatca agaatatttg   1080
aaaacatttt ataaggatct tttgaattgt tatgaagagt ttgagcaagt gcttacaaaa   1140
gaagaaactt atagagttca ttatgcaaaa gaagtgttta aagagttaat ccgatcatat   1200
tttgatgaag ctcgatggtt gaatagtgga cgtgtcccaa attttgaaga gtacatggaa   1260
tttgcaacca ttaattgtgg ttactatatg ttgatagtga gttctttggt tggaatgaaa   1320
acaagtattg taaccaaaga tgtttttgag tggctctcca aagatcgaaa gattattaga   1380
```

```
gcatctgtta ttatttgtag gctcatggat gacatagctg aacacaagtt tgagaaagac   1440

aaatatgatg aagattctgc cattgaatcg tatatgatgc aacatggtgt ttgtgaagaa   1500

gaagcctatg atgaactcaa taagcttata attaatgcat ggaaagaaat aaatgaagag   1560

tttttgaagc caactaaatt agcttcaccc atattacttc gtgttcttaa tttttctagg   1620

gttatggatc ttctctacaa aaatggtgat aactatacac aagttggaaa agtcactaaa   1680

gatagtgttg ctgtcttgct cattgatcca attccataa                          1719
```

```
<210> SEQ ID NO 17
<211> LENGTH: 1671
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3374046, library_id:2654

<400> SEQUENCE: 17

atgtcatatc aagttttagc ctcatcacaa aatgacaaag tatcaaaaat tgttcgtcca     60

acaacaactt atcaaccttc tatttggggg gagagatttc tccaatatag tatttcagac    120

caagacttta gctataaaaa gcagcgagtt gacgaattaa aggaagtggt aaggagagag    180

gtatttttag aatgttatga taatgtttca tatgtgttga agatagtgga tgatgttcaa    240

cgtttgggat tgtcgtatca ttttgaaaat gaaatagaaa aagcgctaca acacatttac    300

gataacacta ttcatcaaaa ccacaaagat gaagatttac atgacacttc tacccgcttt    360

agactattgc gccaacatgg atttatggtt tcatctaata tatttaaaat atttaaagat    420

gagcaaggga attttaagga gtgcttgata actgacattc ttggtttgct gagcttatat    480

gaggcctcac atttaagcta tattggcgag aatatattaa atgaagcact tgctttcacc    540

accactcacc ttcatcagtt tgtgaaaaat gaaaaaacac atccattatc aaatgaagta    600

ttactagcct tgcagagacc tataagaaag agcctagaga ggctccacgc caggcattac    660

atttcatctt acgaaaacaa gatttctcat aacaaaacat tgctagaact tgcaaagttg    720

gatttcaatc tattacaatg tttgcataga aaagagctta gtcaaatttc caggtggtgg    780

aaagaaatag actttgtaca caaactacct tttgcaagag ataggattgt ggagctatac    840

ctttggctat taggagtttt tcatgaacct gaattgtcac tggcaagaat tatttcaaca    900

aaagttattg cattggcctc agttgcagat gatatttatg atgcatatgg tacatttgaa    960

gagcttgagc tccttactga atcaattaat aggtgggact taaattgtgc ggatcaactt   1020

cgtccagaat gtttacagac attttataag gttcttttaa attgttatga agaatttgag   1080

agtgagcttg gaaaggagga aagttacaaa gtttactacg caagagaagc gatgaaaaga   1140

ttacttggag catatttcag tgaagctcga tggttgcacg aaggatattt ccctagcttc   1200

gatgagcatt tgaaggtttc tttgatttct tgtggataca ccatgatgat agtgacctct   1260

ttaattggca tgaaagattg tgtaacaaag caagattttg agtggctctc aaaagacccc   1320

aagataatga gagattgcaa tatcctttgt aggttcatgg atgacatagt ctctcataag   1380

tttgagcaac aaagagatca ttcaccgtct accgttgaga gttacatgag gcaatatggg   1440

gtgtcagaac aagaggcatg tgatgagcta agaaagcaag tgattaattc atggaaagaa   1500

ataaacaaag cattcctcag gccttctaat gtgccttatc cagttttatc tcttgttctc   1560

aatttttcga gagtaatgga tcttctctac aaagatggtg atggctatac gcatattgga   1620
```

aaagagacaa aaaatagtgt tgttgcgtta cttatagatc aaatcccatg a 1671

<210> SEQ ID NO 18
<211> LENGTH: 1857
<212> TYPE: DNA
<213> ORGANISM: Cannabis sp.
<220> FEATURE:
<223> OTHER INFORMATION: Beta myrcene/limonene synthase
<220> FEATURE:
<221> NAME/KEY: misc_feature
<222> LOCATION: (0)...(0)
<223> OTHER INFORMATION: EST marker PE2EUKC3374480, library_id:2654

<400> SEQUENCE: 18
atgcattgca taacccttaa acaccaaatt tctccattac tccctaatat ttgcagtact 60
actaattttg gtgtattttt tagaccaaaa ttatatacta attataatat tattaatggt 120
ggtacaaaat caagattatc aagtgcatgc taccccatcc aatgtgctgt ggtcaatagt 180
tctaatgcaa ttattgatcg acgatcagcc aactttgagc cctccatttg gtctttcgat 240
tatattcaat ctcttacaag tcaatataag ggagaacctt atacaagtcg agtgaaaaaa 300
cttgagagag atgtgaaaaa aatattagtt gagatggaaa actctttagc tcaacttgaa 360
ctcattgata cattgcaaag acttggaata tcttaccgtt ttgagaatga aataaattct 420
attttgaaca aaaaatatct caatattaat aatcctaatt ataatttata tgctattgct 480
cttcaattta ggcttctacg tcaacatggc tatgcagtac ctcaagaaat ttttaatcag 540
ttgaaggacg agatagaaaa aatcaaagaa aacataaatg gtaatgatat catgggaata 600
ttagccttat acgaagcttc tttttatgag aaaaaagacg aaagtatttt aaaggaagct 660
agaattttca caactaaatg tctcaaaaac tacactataa tgatatcaga gcaaaaaaag 720
ttaatgattg ataatgatta tgattatgat atcgaagtag tgaatcatgc cttagagctc 780
ccacttcatc ggaggaccac aagaacagaa gcaaagtggt tcattgacgc atatgcgaaa 840
aaacaagaca tgaatcctat gttgcttgag ttagccaaac tcgatttcaa catagtacaa 900
tcaacacatc atgaagatct aaaacatata ttcaggtggt ggagacatac taaacttgga 960
gagaaattga attttgcaag agatcgattg atggaatgtt tcttatggaa tattggaata 1020
agatttgagt caaaattcag ctattttaga acaaaaactg ccaaattatt tgagctagta 1080
acatttatag atgatatata tgatgtttat ggaacattgg atgaattaga gcttttcacc 1140
aaagctgttg agagatggga tgtgaaaatg ataaatgagt taccagaata catgaagatg 1200
ccttatcttg ttttacacaa taccataaat gatatggtct ttgaggtgtt aagagaccaa 1260
ggaatctcca tcaacattca ataccttaag aaaacgtggg tcgatatgtg taaaagtttc 1320
ttgcaagagg caaaatggta ctatagtgga tacacaccaa caatggaaga atatattgaa 1380
aatggttgga tttcagtagg agcaccagtt attcttgtgc atgcttattt ttttcacgca 1440
aataataatc gtacaattac aaatactaaa gagattttcg aatgcttgga atatggttat 1500
tatcctgcca ttattcgtca cagtgccata atattacgat ttacaaatga cctagcaaca 1560
tcatcggagg aattgaaaag aggtgatgct ccgacatcaa ttcaatgtta catgcaagaa 1620
aaaaatgtat ctgaagaaga agctcgtgaa catgttaagt ttttaataaa tgaagcatgg 1680
aaggagatga ataatgatgt tggattatat ccaatctcat tgactgaaga tgctacaaac 1740
tttgctaaga tgggattttt catatatcaa catggtgatg gtcatagttc tcaagataat 1800
caatccaaac aaaaaatttc atccttgatt attgaaccta ttcccctata tacataa 1857

<210> SEQ ID NO 19
<211> LENGTH: 1725
<212> TYPE: DNA
<213> ORGANISM: Cannabis sp.
<220> FEATURE:
<223> OTHER INFORMATION: ( )-limonene synthase 2
<220> FEATURE:
<221> NAME/KEY: misc_feature
<222> LOCATION: (0)...(0)
<223> OTHER INFORMATION: EST marker PE2EUKC3374792, library_id:2654

<400> SEQUENCE: 19

```
atgacgcagt taggagtaat ctccagtagt actacaatat tcaaagaaca accggaagca     60
attgtccgac gatcaggaaa ctacaaaccc acgttgtggg atgctcattt tttcaaatca    120
ctccaagtca tatatacgga ggaaagctat gggaaaagaa tcaatgagct gaaagaagat    180
gtgagaagaa ttcttgagaa ggaggctgaa aatcctttag ttaagcttga acagatcaat    240
gatttgagca gacttggaat atcttatcac tttgaagatc aaattaagac aatattaaac    300
ctgacattta acaataataa tgcattgtgg aagaaagata atttgtatgc cactgctctt    360
catttcaaac tccttcgaca atatggattc agtcctgtat cttcagaggt tttcaatgct    420
ttcaaagacg agaaaaagga gttcaaagag agtttgagta aggatgtgaa aggaatggta    480
tgtctatatg aggcttcatt ctattcattt aggggtgaac ccatattaga tgaagcaaga    540
gacttcacaa ccaaacatct caaacaatac ttgatgacaa ggcaaagtca aactaaaaca    600
gttgaccatc atgatgatga tgatcatgat cttgtgaaac tggtagagca tgccttggat    660
cttccactcc attggagatt gccaagattg gaggctaggt ggtttattga tatgtatgct    720
gaaaggaatt atgatatgaa tccaactttt cttgactttg ctaaacttga ctataacttc    780
gttcagtcag cataccaaaa agagctcaaa tatatttcaa ggtggtggag tggttctaga    840
ttgacagaaa ggctaccatt tgctagagac agagtagtgg aaattttcta ttctgcagtg    900
gcactaaaat atgaggcaga atttggattt gttagaactg tgatgacaaa aattggtctc    960
ttgctaacac tcatggacga tatatatgat gtgtatggta cactagatga gcttcagctt   1020
tttctagagg caattgagag gtggaatata aatgaactgg atcagctacc cgattacatg   1080
aagatattgt ttgttgcttt ttataacaat gtgaatgaga tatcttatta tgtcctcaaa   1140
gaaaatggga ttcacaccat caaatatctg aagaaagcgt tgggtgatct gtgtaaatgc   1200
tatatggagg aggcaaaatg gtttcacagt ggacacatac caagtttaga agaattcatt   1260
gagaatggat ggaaatcaat tacaatacct ctttgtctta tctatcatta ttgcttaatt   1320
acaacttcaa ttacagaaca agacatggaa cacttgcttc aatatccaac cattttacgt   1380
gtctcaggaa ctgtttttcg atttatagat gacttgggaa cctcatcaga tgaacttgaa   1440
agaggagata atccttcatc aattcaatgc tacatgcgtg aaaagggtgt tagtgaaaat   1500
gaaagccgtg aacacatatg gaatttaatt agtgaaggat ggaaggaaat taatgaagtt   1560
aaagcttcaa actctcccata ctctcaagtg tttattgaat ctgccattga ttttgttaga   1620
ggagcaatgg agatgtacca caagggtgat ggttttggta ctaatcaaga ccgatatctt   1680
aagaccaaag ttgtcaacat gttcttcgat ccaattccaa tttaa                   1725
```

<210> SEQ ID NO 20
<211> LENGTH: 1821
<212> TYPE: DNA
<213> ORGANISM: Cannabis sp.
<220> FEATURE:
<223> OTHER INFORMATION: P(E)-nerolidol/(E,E)-geranyl linalool synthase

```
<220> FEATURE:
<221> NAME/KEY: misc_feature
<222> LOCATION: (0)...(0)
<223> OTHER INFORMATION: EST marker PE2EUKC3374920, library_id:2654

<400> SEQUENCE: 20

atgaatttgc tatcatatct tgaagcgttg ccttcatcgt attttaaaga agattattct     60

aatacaatta taaagaattt gtgtgaagaa ggctctttat tccaatcgcc atcggccact    120

gcatgtgctt tcatggctac tcgaaatttc aaatgcttgc attatttgca aaccctagct    180

gaaacattca caaacaataa taatgttacg acaattccca ccacatatcc caacaatgaa    240

gatcttataa agctttgcat tatcaacctc atcgaaaggt tagggttggc tgagtatttc    300

actgtggaga tcgaggaagt tcttcaacaa gtttataaga attatatgaa acatgatgaa    360

ttattttctt acaaaaatgt ggcaacttta gagttacatc tactcaaaga atcattagct    420

tttaggcttc taagaatgca tggctacaaa gtatttccta gtaacatatg ttggttccta    480

aagaatgagg aaataaaaaa ctacatagaa ttcaactctg aatacttttt tgttgcaatg    540

ctaaatcttt acagagctac tgatcttgct tttcatggtg aatttgagct tgatgaacta    600

agaacatttt caagaaaatt acttgagaaa tctatttcag aaggagctca acatacatat    660

ccctttaaga aactgattga gcatgagtta agtcttccat ggatggctcg actagatcac    720

ctcgaacata ggtttttat cgaacaaact aataaagctt tatggatggg aaagacatct    780

tcacaaaggt tatcaaagtt ttacaatgat aaattacttc gtctagccac tttaaactac    840

gagttcaaac agtatattta caagagtgaa cttgaacagt taacaaggtg gaataatgaa    900

gggttgagtg gtgttagtaa aaagatattt gatgccctag ataatcttgt aagggaaatg    960

tcaactatgt accttgaaca acaagaaaaa agtcatgaag acataaccag ctacataaga   1020

aaaatttggt atgaaacgat ttgttcatgg cttactgaat ctgaatggag taaaagtggg   1080

attgtaccaa ccatggaaga atattttaaa gtttcaatga cttctgtagc aactcatacc   1140

ttgcttcttc cagcttcatt tcttctgaaa ccgaccttaa aaaaatctca attacaatta   1200

atggagtatg aaagtgttac taaattggtc atgattattt gtcgtttgtt gaatgactta   1260

caaagttctg agagggaaag agaagaaggc aaaccaaact caattacagt ttacatgaag   1320

aataattttg agatagagaa taaggaagaa gtagtaaagt acttgaaaga gatattaaac   1380

gataagaaga aggagttcct tgagcatgtt ttgattgatg acaatggctt taccaatctt   1440

tctaaagagt gtaggcttct acacttatct tgcttaaaag tattccaaat gttctttaac   1500

tcttcaaatc gatatgattc agacactgaa ttgcttgaag acattaacaa agcgatttac   1560

attcctttga aatcgattaa tcatgaagga acattagaaa agaatctcgt aaagcctcca   1620

aagccatcga tgattgatct tcctcgaatc aaatcgtcat caccgaccaa gaaatgtttg   1680

atgaacatga attactttag ccaaccctct aaacattttt tcatgaatga actaatttcc   1740

tttcataaaa ataaaaaagt tgacaattgg aaaatagcta cacctattat gccattaaaa   1800

gtcaacttgt gcttcatttg a                                             1821


<210> SEQ ID NO 21
<211> LENGTH: 1479
<212> TYPE: DNA
<213> ORGANISM: Cannabis sp.
<220> FEATURE:
<223> OTHER INFORMATION: P(E)-nerolidol/(E,E)-geranyl linalool synthase
<220> FEATURE:
<221> NAME/KEY: misc_feature
<222> LOCATION: (0)...(0)
```

<223> OTHER INFORMATION: EST marker PE2EUKC3374958, library_id:2654

<400> SEQUENCE: 21

```
atgatatatg tagttcccac cacatatccc aacaataaag atcttataaa gctttgcatt      60
atcaacctca tcgaaaggtt agggttggct gagtatttca ctgtggagat cgaagaagtt     120
cttcaacaag tttataagaa ttacatgaaa catgatgaat tattttctta caaaaatgtg     180
gcaactttag agttacatct actcaaagaa tcattagctt ttaggcttct aagaatgcat     240
ggctacaaag tatttcctag taacatatgt tggttcctaa agaatgagga aataaaaaac     300
tacatagaat tcaactctga atactttttt gttgcaatgc taaatcttta cagagctact     360
gatcttgctt ttcatggtga atttgagctt gatgaactaa gaacattttc aagaaaatta     420
cttgagaaat ctatttcaga aggagctcaa catacaaatc cctttaagaa actgattgag     480
catgagttaa gtcttccatg gatggctcga ctagatcacc tcgaacatag actttttatc     540
gaacaaacta ataaagctca atcatcttta tggatgggaa agacttcttt ccaaaggttg     600
tcgaggtttc acaacgacaa actagttcgt ctagccacct taaattatga gttcaaacaa     660
tctatttaca agaccgaact tgaacaatta acaaggtggt gtaaatattg gggacttaat     720
gaaatgggat ttggtagaga aaaaagtaca tacaattatt ttgcagtagc ttgtgcttgc     780
tgttatttgc cttatgattc tccaattcga ttgatgatta caaagggtgc tataatagta     840
acggttgctg atgatttttt tgatatgaaa ggctctctat tcactgattt aaaattcttc     900
actaaggcaa ttcaaaggtg gaataatgaa gggttgagtg gtgttagtaa aaagatattt     960
gatgccctag ataatcttgt aagggaaatg tcaactatgt accttgaaca acaagaaaaa    1020
agtcatgaag acataaccag ctacataaga aaaatttggt atgaaacgat ttgttcatgg    1080
cttactgaat ctgaatggag taaaagtggg attgtaccaa ccatggaaga atattttaaa    1140
gtttcaatga cttctgtagc aactcatacc ttgcttcttc cagcttcatt tcttctgaaa    1200
ccgaccttaa aaaaatctca attacaatta atggagtatg aaagtgttac taaattggtc    1260
atgattattt gtcgtttgtt gaatgactta caaagttctg agagggaaag agaagaaggc    1320
aaaccaaact caattacagt ttacatgaag aataattttg agatagagaa taaggaagaa    1380
gtagtaaagt acttgaaaga gatattaaac gataagaaga aggagttcct tgagcatgtt    1440
ttgattgatg acaatggctt taccaatctt tctaaagaa                           1479
```

<210> SEQ ID NO 22
<211> LENGTH: 1659
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3376119, library_id:2654

<400> SEQUENCE: 22

```
atgtcaaata ttcaagtctt agcttcatct caattaagtg acaaaattat tgctcgtcca      60
acaacaaatt ttcacccttc tatttggggc gatcgattcc tccattacaa tgtttcagaa     120
caagacttgg tttgcaaaca agaaagaatt gaagaattaa tacaagttgt gaagaaagag     180
atattatctt caaatcatga tcaattgaag ttgattgaca atctccaacg tttgggatta     240
tcacatcatt ttgagagtga aattgagaaa ttgttggaac aattaagtat cggcactcat     300
catcaaaatc atcaagatct acatgatgct tctctttggt ttagattatt aagacaacat     360
```

```
ggatttaatg tttcatcaaa tatatttgaa aaatttaagg acgatgaagg taactttaag    420
aaaagcttga taaccgatgt ttcgggtttg cttaatttgt atgaggcttc acacttgagt    480
tatgttggag aaagcatact agatgaagca cttgctttca caaccactca ccttaaggct    540
attgtggcaa atagtaaaga tcatccatta tcacatcaaa tatccaaagc cttggaaagg    600
ccactaagaa tgaccttaga gaggcttcat gctaggtttt acatctcaat ctatgaaaag    660
gatgcctctc ataacaaagt attgctagag cttgcaaagt tagacttcaa tctacttcaa    720
tgtttccaca aaaaggagct tagtgaaatt gtgaggtggt ggaaggagca tgagtttgca    780
aagaaattcc cttttgcaag agataggatg gtggaactgt atttttggat attgggtgtt    840
tattatgaac ccaaatactc tcgagcaaga aaacttctaa ccaaagtcat tgcattgacc    900
tcaatcactg atgatactta tgatgcatat ggtactattg atgagcttca gcttcttacc    960
aaagcaatgc agaggtggga cataaattgt atggataaac ttgagccaga atatttaaag   1020
acatattata aggtaatgtt ggaatcttat gaagaatttg aaaaggagct taaaaaggaa   1080
gaattataca aacttgagta tgcaaaagaa gagatgaaaa gaattattgg agcttatttt   1140
gaagaagctc gatggttaaa tgaaggatat ttgccaagct tcgatgagca tttgagagtc   1200
tcttatattt cttctggtta cgttttgttg atagccacaa gttatgtagg aatgcatgat   1260
attgtaacac atgaaactct aaattggctc tccaaagacc ctaagattgt ttcagcttct   1320
actctcctct caagattcat ggatgacata ggctctcgca agtttgaaca agagagaaat   1380
cacgtactat ctacagtgga atgttacatg aagcaatatg aggtttcaga ggaagaagca   1440
attaaagaac ttaataaaag agtggccaat tgttggaaag aaataaatga agactttatt   1500
agaccaacta gtgtgccttt tcctatttta tttcgtatta ttaatttgac caagacagct   1560
gattttatgt acagagaagg tggtgaccaa tatacacatg ttggaaaggt gttgaaagat   1620
agcattgctg ctttacttat agatccaatc ccatattaa                          1659
```

<210> SEQ ID NO 23
<211> LENGTH: 1857
<212> TYPE: DNA
<213> ORGANISM: Cannabis sp.
<220> FEATURE:
<223> OTHER INFORMATION: Beta myrcene/limonene synthase
<220> FEATURE:
<221> NAME/KEY: misc_feature
<222> LOCATION: (0)...(0)
<223> OTHER INFORMATION: EST marker PE2EUKC3376254, library_id:2654

<400> SEQUENCE: 23

```
atgcattgca taacccttaa acaccaaatt tctccattac tccctaatat ttgcagtact     60
actaattttg gtgtattttt tagaccaaaa ttatatacta attataatat tattaatggt    120
ggtacaaaat caagattatc aagtgcatgc taccccatcc aatgtgctgt ggtcaatagt    180
tctaatgcaa ttattgatcg acgatcagcc aactttgagc cctccatttg gtctttcgat    240
tatattcaat ctcttacaag tcaatataag ggagaacctt atacaagtcg agtgaaaaaa    300
cttgagagag atgtgaaaaa aatattagtt gagatggaaa actctttagc tcaacttgaa    360
ctcattgaca cgttacaaag acttggagta tcttatcgtt ttgagaatga aataaatact    420
attttaaaag aaaaatatgt caatattaat ggtaatatta ataaccctaa ttataattta    480
tatgccactg ctcttgaatt taggcttcta cgtcaacatg gttatgctgt acctcaagag    540
acttttaatt attttaagga cgagacagga aaattcaaaa caaacataag tggtgatatc    600
```

attggagtat tggccttata tgaagcttca ttctatgaaa aaaaaggcga aaacatttta 660
gaggaagcta gaattttcac aactgaacgt ctcaaaaact acataatgat atcagagcaa 720
aagaaattga tgattaataa taattatgat tattattacg atattgaagt agtgaatcat 780
gctttggagc tcccacttca tcgaaggacc acaagaatag aagctaagtg gttcatcgat 840
atgtacaaga aaaaacaaga catgaatcct attttgcttg agtttgccaa actcgatttc 900
aacatgatac aatcaacaca tcatgaagat ttgaaacata tattcaggtg gtggaggcat 960
actaaacttg gtgagaaatt gaattttgca agagatcgat tgatggaatg ttttttatgg 1020
aaagttggaa taagatttga gccaaaattc agttatttta gaacaacaac tgtcaaatta 1080
cttgagctaa taacattaat tgatgatata tatgatgttt atggaacatt agatgaatta 1140
gagcttttca ccaaagctat tgagagatgg gatgtggaaa tgataaatga attaccagaa 1200
tacatgaaga tgccttatat tgttttacac aatacaataa atgaaatggt atttgagata 1260
ttaagagatc aacaaatcac catcaaaatt caatacttaa agaaaacgtg ggtagatatg 1320
tgtagatgtt ttctacaaga agcaaaatgg tactacagtg gatacacacc aacattggaa 1380
gaatatattg aaaatggttg gatttcagtg ggagcaccag ttcttattgt gcatgcttat 1440
ttttctcatt caaataataa taaagagatt tttgaatgct tggaacatgg ttattatcct 1500
accataattc gtcacagtgc cataataata cgacttacaa atgacctagc aacatcatct 1560
gaggaactga aaagaggtga tgctccgacg tcaattcaat gttacatgca agaaaaaaat 1620
atatgtgaag aggaagctcg tgaacatatt aagtttttaa taagtgaagc gtggaaggag 1680
atgaatatca gtgaatctga tgatggatta atatatccaa tctcattgat tgaagatgcg 1740
agaaactttg ctaggatagg attattcatg tatcaacatg gtgatggtca cagttctcag 1800
gataatctat ccaaagaaag aatttcatcc tttattatta aacctattcc cctatag 1857

<210> SEQ ID NO 24
<211> LENGTH: 1722
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3376800, library_id:2654

<400> SEQUENCE: 24
atgtccactc aaatcttagc atcatcatca tcttcaaatg aaaacccaaa taaaattgtt 60
cgtcctacaa aaacatttca tccacatatt tggggagaac aattcttaca ttacaacatt 120
tcagaacaag atttgtattg tcaacaacaa aaggttgagg aattaaagga agtggttaga 180
agagaaatat ttggagaatc atcaatatca tcatcagctt attatgatgc ttggaaaaat 240
caattgaaga taattgatgt ggtagaacgt ttgggattgt cttatcattt tgaaactgaa 300
atagaaaata tgatagaaca aatctacaac aaaaccaata attttgatct tcttaaggat 360
gaagagttgc atgatgtttc cttgtgggtt agacttctac gacaacatgg atttagggtt 420
tcttctgata tatttaaaaa attcaaagat gaggatggaa actttaaaaa atgtttggta 480
agtgatactc ttggtttgct tagcttatat gaagcctcac atttgagttg tggtggagaa 540
aatatacttg atgaagcact tgctttcaca acaacacacc taaatgagtt tttggcgaag 600
aaaaaagaac accatgatga cgatgatcca ttatcgaaag aaatatatcg tgccctagag 660
aggcccttaa gaaagaccct agtgaatctc catgcaaggt atttcatttc aatatatgaa 720

```
aaagatgcct cacataacaa agtattgcta caacttgcaa agttagattt caatctatta    780

caatccatgc acaaaaagga gcttagtgaa atctcaaggt ggtggaagga attagacagt    840

gcacacaact ttccatttgc aagaaatagg attgtggaac tatacatttg gatattagga    900

gtctattatg aaccccaata ctcttttgca agaaatattt tagtgaagat catagcactt    960

tcctcaatcg ctgatgatat ttatgattca tatggtatat ttgaagaaca taagctcctt   1020

attgaagcaa ttgataggtg ggacaaaaat tgtatggata aactccatcc agaatacttg   1080

cagaaatatt ataagatact tttgcaatct tttgaggaat ttgaacaaga gtttgaaaag   1140

gaggaaactt acaaagttta ctatggaaaa gaaacgttta aaagattatt aagaggttat   1200

tttgaggaag ctcgatggtt gaatgaagga tacatgccaa gtttggagga gcatttaaaa   1260

gtttctttgg ttacttctgg ttatttcatg ttgatggctt gctctttagt tggaatgaaa   1320

agtaacaata ttgtaaccaa acaagttttc gagtggctct ccaaagaccc caagattgtt   1380

agggcaagcg ctagtgtttg caggtacatg gatgacgtgg ctggtcacaa gaatgagcaa   1440

gagagaaatc atataccatc tacaatagaa tgttacatga agcaatatgg tgtatcagaa   1500

gaagaagcat gtgatgaaat gaataggcga gtggttattg catggaaaga aataaacgaa   1560

gagtttctca aaccaactga agcagcttca cctatattag ttcgtgctct gaatcttgct   1620

agggttatgg atcttctcta caaaaatggt gataactata cacaagttgg aaaagtcact   1680

aaagatagtg ttgctgtctt gctcattgat ccaattccat aa                      1722
```

<210> SEQ ID NO 25
<211> LENGTH: 1839
<212> TYPE: DNA
<213> ORGANISM: Cannabis sp.
<220> FEATURE:
<223> OTHER INFORMATION: (R)-limonene synthase
<220> FEATURE:
<221> NAME/KEY: misc_feature
<222> LOCATION: (0)...(0)
<223> OTHER INFORMATION: EST marker PE2EUKC3376880, library_id:2654

<400> SEQUENCE: 25

```
atgtcatcga ttatttattc cccgtttact tctctacttc cactaaagcc aatatcatca     60

gcatcatcaa cagcaacaat taatacaaga ttaaaaaacc gattccgatc atcaatacta    120

gtagtactac gaccccagca aagacgctca gctaagtacc atcctacagt ttgggaaaat    180

aagcatatcg actctttctt tactccctac aactatgagt tacactctga acgactacaa    240

gagttgaagc aagttacgag tacttcactt agaaccacaa aagacccttg tattctctta    300

aagcttattg attctatcca aaggttggga ctcgaatatc acttcgaaaa tgagattaaa    360

gatgctgttt ctttcattta cgcacataat gatcaaacta ccagtaatga tctcttcatg    420

acagcactta gatttcgtat tcttaggcaa catggcttat ttgttggctc agatgtgttt    480

gacagattta gaggcagaga tgggaaattc ttggacagct taagcagtaa caagcatgga    540

attttgagtt tgtatgaagc ttcacacctt ggaatggctg aagaaaatgt tttggaggaa    600

gccaagagtt tcaccaccaa aaggctaaga tatttctcag ctgggaaaat ggataatact    660

ttgtttggta agcaagtgaa acaatcactg gaagttccac tgtattggag gatgccaaga    720

tctgaagcta ggaatttcat tgatctctac caaatggatg agacaaagag tgtgactttg    780

cttgagttgg ctaagttgga ttataatctg gtccaatctg tgcatcaaaa tgagcttaag    840

gagttgggaa ggtggtggga aaatttggga ttcaagaaaa atctaccttt tgcaagagat    900
```

cgtgtggtgg agaactattt gtgggccgtg ggaatcgtat ctgagccaca gttctccaaa 960
tgcaggatag gcttaaccaa gttcgtttgc atattaacag caatagatga tgtttatgac 1020
atatatggat cattagatga gcttgaactt ttcacaaatg cagtagaaag ctgggacata 1080
agggcaataa gggatgaatt tcctctttat ttgaaaacat gctatcttgg catgcttaat 1140
tttggtaatg aagtgatcga tgatgttctt caaaaccatg gcttgaatat ttcctcctac 1200
attaaagaag agtggttaaa tctctgcaaa tcatatcttg tagaagcaag gtggttttat 1260
aatgattata caccaagttt gaatgaatac ttggaaaatt catctacttc agttggtggt 1320
catgcagcta tagttcatgc ttgtatttta atcttagatg gctccatacc cgaaacctta 1380
ctggattaca atttcaacca ttttcactct aagctgattt attggtcatc tctcataaca 1440
aggcttagtg atgatttagg aacttcaaag gatgagctta aaagaggaga tgtgaagaaa 1500
tcagtggagt gctacatggc agagaaagga atatgggaag aagaagaagc aataaatcac 1560
ataaaagaat tgagaagaaa ttcatggaaa atggtgaaca aggagataat aattgggaat 1620
aattgcttgc caaaaataat ggtgaagatg tgcttgaaca tggcaagaac tgctcaattc 1680
atattccaac atggtgatgg aattggcaca tcaactgggg ccaccaaaca tcgtttagcc 1740
tcattgattg tcaaacctgt acacatcgat ccatgttcca aaccaattaa tggacttgga 1800
gactcacata caaccataaa aactaaaata aaaaaataa 1839

<210> SEQ ID NO 26
<211> LENGTH: 1728
<212> TYPE: DNA
<213> ORGANISM: Cannabis sp.
<220> FEATURE:
<223> OTHER INFORMATION: Beta myrcene/limonene synthase
<220> FEATURE:
<221> NAME/KEY: misc_feature
<222> LOCATION: (0)...(0)
<223> OTHER INFORMATION: EST marker PE2EUKC3376881, library_id:2654

<400> SEQUENCE: 26
atgtcactat caggactaat ctccactact actttcaaag aacaaccagc aatagtccgt 60
cgatcaggaa actacaaacc cccattgtgg gatgctcatt ttatccaatc actccaagtc 120
atatatacgg aggaaagcta tgggaaaaga atcaatgagc tgaaagaaga tgtgagaaga 180
attcttgaga aggaggctga aaatccttta gttaagcttg aacagattaa tgatttgagc 240
agacttggaa tatcttatca ctttgaagat caaattaaga caatattaaa cctgacattt 300
aacaataata atgcattgtg gaagaaagat aatctgtatg ccactgctct tcatttcaaa 360
ctccttagac aatatggatt caatcctgta tcttcagagg ttttcaatgc tttcaaagac 420
gagaaaaagg agttcaaaga gagtttgagt aaggatgtga aaggaatggt atgtctatat 480
gaggcttcat tctattcatt taggggtgaa cccatattag atgaagcaag agatttcaca 540
acaaaacatc tcaaacaata cttgatgatg acgaggcaag gtaaaactat atctgttgac 600
catgatgata ataatgattt aatggtgaaa ttagtggagc atgctttgga gcttccagtg 660
cattggagaa tgaaaaggtt ggaggcaagg tggtttattg atatgtatgc tgaaatgtct 720
catcatcatc atatgaattc aacttttctt caacttgcta aactagattt taacgttgta 780
caatcaacat accaagaaga ccttaaacat gctgtaaggt ggtggaaaac tactagtcta 840
ggagaaaggt taccctttgc aagagatagg atagttgaaa cgttcttatg gagtgtggga 900
gttaaatttg agccacagtt tagatattgc cgaaaaatgc tcacaaagat gggtcaattg 960
gtaacctcaa tggacgatat atttgacgtg tatggtacgc ttgatgagct aagcctcttt 1020

```
caagacgcat tggaaaggtg ggatataaat acgatagacc aacttccaga ttacatgaag   1080
atattttttt tggctgctta taatgtggtg aatgaaatgg cgtatgacgt gctaaaacaa   1140
aatgggattc tcattatcaa atatttaaag aaaacgtgga cggatttatg taaatgttac   1200
atgttggagg caaattggta tcatagtgga tacacaccaa gcttggaaga atacattaaa   1260
aatggatgga tatcaattgc agaaccctta cttctagtca atctttattg ccttataacc   1320
aatccaataa aagaagatga catggactgc ttgcttcaat atcccacctt tattcgtatc   1380
tcaggaatca ttgttcgact tgttgatgat ttaggaactt catcggatga actgaaaaga   1440
ggagacaatc ctaaatcgat tcaatgctat atgaaagaaa atggtatttg tgatgaaaag   1500
aatggccgtg aacacataag gaatttaatc agtgaaacat ggaaggaaat gaatgaagct   1560
cgagtgggtg agtctccatt ttctcaagct tttattgaaa ctgccataga tttcgttagg   1620
acagcaatga tgatatacca aaaggagcaa gatggggttg gtactaatat tgatcattac   1680
acaaaagatg gaatcatttc cttgttcttc acttccattc ccatttga               1728
```

```
<210> SEQ ID NO 27
<211> LENGTH: 1704
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3377036, library_id:2654

<400> SEQUENCE: 27
```

```
atgtcgtctc aaatcttagc aacctcatcc aaaaatgaca atatacataa aattgttcgg     60
ccaacaacaa attatcatcc ttctatttgg ggagaccgat tttgcatta cgatattcca    120
aaagaagaat tgagttataa acaaggccaa gttgaagaat tgaaaaaagt ggtaagaaag    180
gagatatttg gagaattctt atgtgatgat tggaataatc gattgaagtt aattgatgtg    240
gtgcaacgtt tgggattgtc ctatcatttt gagagtgaaa tacaaaatga gcttcaacac    300
atttacaaca aaataagcat taatgataat aatttcaaac atgaaacttt gcatgatgct    360
tctattcggt ttagacttct acgacaacat ggatataggg tttctttaga tatatttgac    420
aagttcaaag atgagaatgg caactttaaa gaatgtttgg cgagtgacac cgttggtttg    480
cttagcttat atgaggcctc acatttgagc tgtgttggag aaaatttact agatgaagcc    540
ctttctttca ctaccaaaca cctaactgaa tttttggaaa ataataaaaa agaacacccc    600
aatgatgatc cattatcaaa ggaaatatct cgagccctag agaggccctt aagaaagacc    660
ctagtgaatc tccatgcaag gtatttcatt tcaatatatg aaaaagatgc ctcacataac    720
aaagtattgc tacaacttgc aaagttagat ttcaatctat tacaatccat gcacaaaaag    780
gagcttagtg aaatctcaag gtggtggaag gaattagaca gtgcacacaa ctttccattt    840
gcaagaaata ggattgtgga actatacatt tggatattag gagtctatta tgaaccccaa    900
tactcttttg caagaaatat tttagtgaag atcatagcac tttcctcaat cgctgatgat    960
atttatgatt catatggtat atttgaagaa cataagctcc ttattgaagc aattgatagg   1020
tgggacaaaa attgtatgga taaactccat ccagaatact tgcagaaata ttataagata   1080
cttttgcaat cttttgagga atttgaacaa gagtttgaaa aggaggaaac ttacaaagtt   1140
tactatggaa aagaaacgtt taaaagatta ttaagaggtt attttgagga agctcgatgg   1200
```

```
ttgaatgaag gatacatgcc aagtttggag gagcatttaa aagtttcttt ggttacttct   1260

ggttatttca tgttgatggc ttgctcttta gttggaatga aaagtaacaa tattgtaacc   1320

aaacaagttt tcgagtggct ctccaaagac cccaagattg ttagggcaag cgctagtgtt   1380

tgcaggtaca tggatgacgt ggctggtcac aagaatgagc aagagagaaa tcatatacca   1440

tctacaatag aatgttacat gaagcaatat ggtgtatcag aagaagaagc atgtgatgaa   1500

atgaataggc gagtggttat tgcatggaaa gaaataaacg aagagtttct caaaccaact   1560

gaagcagctt cacctatatt agttcgtgct ctgaatcttg ctagggttat ggatcttctc   1620

tacaaaaatg gtgataacta tacacaagtt ggaaaagtca ctaaagatag tgttgctgtc   1680

ttgctcattg atccaattcc ataa                                          1704
```

<210> SEQ ID NO 28
<211> LENGTH: 1374
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3377775, library_id:2654

<400> SEQUENCE: 28

```
atgtcaaata ttcaagtctt agcttcatct caattaagtg acaaaattat tgctcgtcca     60

acaacaaatt ttcacccttc tatttggggc gatcgattcc tccattacaa tgtttcagaa    120

caagacttgg tttgcaaaca agaaagaatt gaagaattaa tacaagttgt gaagaaagag    180

atattatctt caaatcatga tcaattgaag ttgattgaca atctccaacg tttgggatta    240

tcacatcatt ttgagagtga aattgagaaa ttgttggaac aattaagtat cggcactcat    300

catcaaaatc atcaagatct acatgatgct tctctttggt ttagattatt aagacaacat    360

ggatttaatg tttcatcaaa tatatttgaa aaatttaagg acgatgaagg taactttaag    420

aaaagcttga taaccgacgt ttcgggttta cttagtttgt atgaggcttc acacttgagt    480

tatgttggag aaagcatact agatgaagca cttgctttca caaccactca ccttaaggct    540

attgtggcaa atagtaaaga tcatccatta tcacatcaaa tatccaaagc cttggaaagg    600

ccactaagaa tgaccttaga gaggcttcat gctaggtttt acatctcaat ctatgaaaag    660

gatgcctctc ataacaaagt attgctagag cttgcaaagt tagacttcaa tctacttcaa    720

tgtttccaca aaaaggagct tagtgaaatt gtgaggtggt ggaaggagca tgagtttgca    780

aagaaattcc cttttgcaag agataggatg gtggaactgt atttttggat attgggtgtt    840

tattatgaac ccaaatactc tcgagcaaga aaacttctaa ccaaagtcat tgcattgacc    900

tcaatcactg atgatattta tgatgcatat ggtactattg atgagcttga gcttcttaca    960

aaagcaatgc aaaggtggga cataacttgt atggataaac ttgagccaga atatttaaag   1020

acatattata aggtaatgtt ggaatcttat gaagaatttg aaaaggagct taaaaaggaa   1080

gaattataca aacttgagta tgcaaaagaa gagatgaaaa gaattattgg agcttatttt   1140

gaagaagctc gatggttaaa tgaaggatat ttgccaagct tcgatgagca tttgagagtc   1200

tcttatattt cttctggtta cgttttgttg atagccacaa gttatgtagg aatgcatgat   1260

attgtaacac atgaaactct aaattggctc tccaaagacc ctaagattgt ttcagcttct   1320

actctcctct caagattcat ggatgacata ggctctcgca agagaaggtg gtga          1374
```

```
<210> SEQ ID NO 29
<211> LENGTH: 1620
<212> TYPE: DNA
<213> ORGANISM: Cannabis sp.
<220> FEATURE:
<223> OTHER INFORMATION: (3S)-linalool/(E)-nerolidol /(E,E)-geranyl
      linalool synthase
<220> FEATURE:
<221> NAME/KEY: misc_feature
<222> LOCATION: (0)...(0)
<223> OTHER INFORMATION: EST marker PE2EUKC3377954, library_id:2654

<400> SEQUENCE: 29

atgtcaacaa aatgccagag tatatcatca tcatcatcac caccattatt gtcaatagat     60

catgatccag ggatggtcgc tgattattat gacaattata agagtactac ctcggaagag    120

ctgttgatca aaaaggttga aatggcatta cgaaaaccta ctgatgatca aagttacaaa    180

atgaggctaa tagatagcat ccaacggttg ggagttggcc attatttcga agaagaaatc    240

aaagtaatcc ttcagatgtt gtcagatttc aattccggcc aagatgacct ctttaacacg    300

gggcttcgtt ttcggctact caggcataat ggctttccaa ctacctcaga tgtttttgac    360

aaattcatca accaaaaagg agaaatagag gatgtaataa tgggccaaga tacattgggt    420

atgctgagct tgtatgaggc atcctacctt gcagcaaatt gtgaagaatc attggtcaag    480

gcaatggaat tcacaagatc tcatctgaaa aattcaatgc ctttcataac ccaaaagcta    540

caaaatcaag ttgccaaagc cttggagctc cctagacacc taaggatggc accattagaa    600

gctcgaaact acatcgacga atacggcaaa gaattaaacc attgccctgc tcttcttgac    660

ttagccaagt tagaatttaa cgagcttcag tcactccaca aaagagaatt aaccgagatc    720

ataaggtggt ggaaacagtt gggtctggtt gagaaacttg gttttgcaag agatcgaccc    780

ttagaatgtt ttttatgggt agtgggaata ttccctggga aatgctattc caacgtccgg    840

attgagctgg ccaaaactgt ttcaatctta ctagtcattg atgatatcta cgacacttac    900

ggatctttgg atgaactcca cttgttcaat catgcaattc taagatggga tcttggtgca    960

atggacaagc ttcctgagta catgaaaata tgttacatgg cactatacaa tactactaat   1020

gaaattggct acagagttct caaagaacat ggattatgcg ttacacaaca cttaaagaaa   1080

gtgtggttag acatatttga tgcatttcta accgaagcag aatggttcga caaaaaatac   1140

actccaactc tagagcaata tttaacaaac ggcgtaacta gtggaggatc ctacatggcc   1200

ttagtgcact catttttcct cataggtcat ggtattacag accaaactat atcaatgatg   1260

cacccatatc ctgagatctt ctcccactca ggcaaaattc taagactttg ggatgatttg   1320

ggaacagcca aggaggagca agagagagga gatgttgctt ctagcataga ttgttatatg   1380

aaagaagaga atattgaatc cgaagatgag gccagaaaac acatcaagaa actgattaga   1440

agatcgtgga tagagctaaa cggagagttg aaggctccta gtgcattgcc tcggtcgatc   1500

accacggcct gttttgacct tgctagaaca gcccaagtca tctatcaaca tggagatgat   1560

caaagctttt taagcgtaga agatcatgta caatctttgt tttttcgacc ctgtcaatga   1620


<210> SEQ ID NO 30
<211> LENGTH: 1716
<212> TYPE: DNA
<213> ORGANISM: Cannabis sp.
<220> FEATURE:
<223> OTHER INFORMATION: ( )-delta-cadinene synthase isozyme A
<220> FEATURE:
<221> NAME/KEY: misc_feature
<222> LOCATION: (0)...(0)
<223> OTHER INFORMATION: EST marker PE2EUKC3378831, library_id:2654
```

<400> SEQUENCE: 30

```
atgtctagtc aagtgttagc ttcatctcaa aaaaatgaca aaacacaaaa catcattcga     60
ccaacaacaa aatttcaccc accaatttgg ggagatcgat tcctccatta caatatttca    120
gaacaagagt tggaatataa agagggacaa gttgaagaat tgaaagaagt tgttaggaaa    180
gagatattcc atggaaataa taaaagaaat attattaatg tttcgaaaca attaaagtta    240
attgatgatg tggaacgttt gggattatct tatcattttg aaagtgaaat agaaaaaaag    300
ctacaacaca tttatgaaat tactaccaat aatattgatc atcaagatca acactactac    360
tactccaacc atgatgaaga tctacatgat gtctctattc gatttagatt actacgacaa    420
catggattta acatttcatc taatatattt gagaaattca aagatgagag tggtaagttt    480
aaggaaagct tgaaaagtga cattgaaggt atgcttagct tgtatgaagc ttcatacttg    540
agctatgttg aagaaaatat actagatgag gctcttgctt tcactaccac caatcttaag    600
ttagtggcca acaaaaaaga acatccatta tcacatgaaa tatccttagc cttatatagg    660
cctttgagaa aaaccctagt gaggctttat gctaggcatt acatttcaat ctatgagaaa    720
caaccttctc ataacaaagt attgctacaa tttgcaaagt tggacttcaa tctactacaa    780
tctttgcata agaaggagct tagtgaaatt tccaggtggt ggaaagaatt agacttggca    840
aacaaactac catttgcaag aaataggatt gtggagctat acctttggat actaggagtc    900
tttcatgaac ctcaattctc tcttgcaaga aaaatcttaa ttaaagccat ttcaatggcc    960
tcagttgcag atgatattta tgatgcatat ggtacatttg aagaacttga gctcctcacc   1020
gaagcaattc tcaggtggga cataagtttt atagataaac ttagtccaga ttatttgaag   1080
acatattata aggtattttt gaattcttat gaagaatgtg aaaaagatct taaaaaggaa   1140
gagagataca aacttcacta tgcaaaagaa tcgatgaaaa aattaataca agcttatttc   1200
catgaagcac aatggttgaa ccaaggacat ttcccaagct ttgatgagca tttgaaagtt   1260
tcttttgtgt cttctggtta cccaatgttg attgagacct cttttgttgg aatgcaagat   1320
gttaaaacaa atcaagtatt tgaatggctc tctacacaac caaagatttt tagagcttgc   1380
actatcattt ctagattcat ggatgaccta gtttctcgta agttcgagca agagaggaat   1440
cacgtaccat ctacagtaga ttgctacatg aagcaatatg gtgtatcgga acaagaggca   1500
tgtgatgagc tcaataaaca agtggttaat ctatggaaag aaataaacca agagtttctt   1560
aggccaactt ctatgccttc atctatctta gttagaattc ttaatttcac aaaagtgctt   1620
gacattatct acaaagaagg tgatggctat acacatgttg gaaaattggt taaggacagt   1680
gttgctgcgt tgcttataga tcccatccca ttatag                             1716
```

<210> SEQ ID NO 31
<211> LENGTH: 1872
<212> TYPE: DNA
<213> ORGANISM: Cannabis sp.
<220> FEATURE:
<223> OTHER INFORMATION: Beta myrcene/limonene synthase
<220> FEATURE:
<221> NAME/KEY: misc_feature
<222> LOCATION: (0)...(0)
<223> OTHER INFORMATION: EST marker PE2EUKC3379063, library_id:2654

<400> SEQUENCE: 31

```
atgcagtgca tagcttttca ccaatttgct tcatcatcat ccctccctat ttggagtagt     60
attgataatc gttttacacc aaaaacttct attacttcta tttcaaaacc aaaaccaaaa    120
```

```
ctaaaatcaa aatcaaactt gaaatcgaga tcgagatcaa gtacttgcta ccccatacaa    180

tgtactgtgg tcgataaccc tagttctacg attactaata atagtgatcg aagatcagcc    240

aactatggac ctcccatttg gtcttttgat tttgttcaat ctcttccaat ccaatataag    300

ggtgaatctt atacaagtcg attaaataag ttggagaaag atgtgaaaag gatgctaatt    360

ggagtggaaa actctttagc ccaacttgaa ctaattgata caatacaaag acttggaata    420

tcttatcgtt ttgaaaatga aatcatttct attttgaaag aaaaattcac caataataat    480

aacaacccta atcctattaa ttatgattta tatgctactg ctctccaatt taggcttcta    540

cgccaatatg gatttgaagt acctcaagaa attttcaata attttaaaaa tcacaagaca    600

ggagagttca aggcaaatat aagtaatgat attatgggag cattgggctt atatgaagct    660

tcattccatg ggaaaaaggg tgaaagtatt ttggaagaag caagaatttt cacaacaaaa    720

tgtctcaaaa aatacaaatt aatgtcaagt agtaataata ataatatgac attaatatca    780

ttattagtga atcatgcttt ggagatgcca cttcaatgga gaatcacaag atcagaagct    840

aaatggttta ttgaagaaat atatgaaaga aaacaagaca tgaatccaac tttacttgag    900

tttgccaaat tggatttcaa tatgctgcaa tcaacatatc aagaggagct caaagtactc    960

tctaggtggt ggaaggattc taaacttgga gagaaattgc ctttcgttag agatagattg   1020

gtggagtgtt tcttatggca agttggagta agatttgagc cacaattcag ttactttaga   1080

ataatggata caaaactcta tgttctatta acaataattg atgatatgca tgacatttat   1140

ggaacattgg aggaactaca acttttcact aatgctcttc aaagatggga tttgaaagaa   1200

ttagataagt taccagatta tatgaagaca gctttctact ttacatacaa tttcacaaat   1260

gaattggcat ttgatgtatt acaagaacat ggttttgttc acattgaata cttcaagaaa   1320

ctgatggtag agttgtgtaa acatcatttg caagaggcaa aatggtttta tagtggatac   1380

aaaccaacat tgcaagaata tgttgagaat ggatggttgt ctgtgggagg acaagttatt   1440

cttatgcatg catatttcgc ttttacaaat cctgttacca aagaggcatt ggaatgtcta   1500

aaagacggtc atcctaacat agttcgccat gcatcgataa tattacgact tgcagatgat   1560

ctaggaacat tgtcggatga actgaaaaga ggcgatgttc ctaaatcaat tcaatgttat   1620

atgcacgata ctggtgcttc tgaagatgaa gctcgtgagc acataaaata tttaataagt   1680

gaatcatgga aggagatgaa taatgaagat ggaaatatta actctttttt ctcaaatgaa   1740

tttgttcaag tttgcaaaaa tcttggtaga gcgtcacaat tcatgtatca gtatggcgat   1800

ggacatgctt ctcagaataa tctatcgaaa gagcgcgttt tagggttgat tattactcct   1860

atccccatgt aa                                                       1872
```

<210> SEQ ID NO 32
<211> LENGTH: 1923
<212> TYPE: DNA
<213> ORGANISM: Cannabis sp.
<220> FEATURE:
<223> OTHER INFORMATION: ( )-limonene synthase 2
<220> FEATURE:
<221> NAME/KEY: misc_feature
<222> LOCATION: (0)...(0)
<223> OTHER INFORMATION: EST marker PE2EUKC3379603, library_id:2654

<400> SEQUENCE: 32

```
atggctgcat tagtgtccac tgtaagtagt attattaggt ggaatagtaa taataataat     60

aataataact tcactagatc tgtgaaatca tgtttaagtt caaattacca taataataat    120

aatattattc ataataaaac tgtattaatg tccaccaata ataataataa taataatcag    180
```

```
aagaatagtt ctcgaagatc agcaaactat caaccccccac tttggcaatt tgattatgta    240

caatcacttt cttctccttt caaggatgaa gcatatgtca aaagagttga gaaactaaag    300

gaagaagtaa gagtgatggt gaagagagca agagaggagg agaagccttt atctcaactt    360

gagctaattg atgtattgca aagacttgga atctcttatc actttgagga tgaaattaat    420

gatatattga aacatatata taacaacaat aatgtgtaca acaccaataa taatgtgtat    480

gccaattctc ttgaatttag actcctacga caacatggtt atccggtgtc tcaagaaatt    540

tttagtacgt gcaaagatga aagaggcaat tttatggtgt gtaccaatga tatcaaagga    600

atgttatctt tatatgaagc ttcattctat ttggtagaaa atgaagatgg tattttggaa    660

gagacaagag aaaaaacaaa aaaatatctt gaggaataca taatcatgat catggaaaaa    720

caacaatcat tattagatca aaataataat aattatgatt atgattatga ttatgaacta    780

gtgagccatg cattggagct tccacttcat tggagaatgt tgagattgga gagtaggtgg    840

tttattgatg tgtatgagaa gagactagac atgaacccta ctctacttac cttagctaaa    900

ctagatttca acattgtcca atcaatatac caagatgatc ttaaacatgt cttcagctgg    960

tgggaaagca ctgatatggg aaagaagttg gaatttgcaa gagatagaac aatggtgaat   1020

ttcttatgga cagtaggagt tgcatttgag ccacatttca aaagttttag aagaatgatt   1080

acaaaagtaa atgctttaat aacagtaata gatgacatat atgatgttta tggtacacta   1140

gatgaattgg agctcttcac taatgcagtt gagagatggg atattagtgc tatggatggg   1200

ctccctgagt atatgaagac atgttttctt gctttataca atttcataaa tgatcttcca   1260

tttgatgtgt taaaaggaga agaaggcctc catataataa aattccttca gaaatcgtgg   1320

gcagatcttt gcaaatctta tttaagagaa gcaagatggt attataatgg atacacacca   1380

agctttgaag agtacattga gaatgcatgg atatcaatat cagggcctgt tatactatca   1440

catttatact tttttgtagt gaatccaaac aaggaaaatg ccttattaag tacttgcttt   1500

gatggatacc ctaccataat acgacattca tcgatgattt tacgacttaa agatgatatg   1560

ggaacttcaa cggatgaatt gaaaagaggc gatgttccta aatcaatcca atgcaaaatg   1620

tatgaagatg gtatatctga agaggaagct cgtcaacgta ttaagttatt aataagtgaa   1680

acatggaagc ttattaataa agattacata aatttggatg atgatgatga tggtggtgat   1740

gactactctc caatgttcta taagtctaat aatattaata aggctttcat tgaaatgtgt   1800

ttaaaccttg gtagaatggc acattgcatt tatcaatatg gagatggaca tggaattcaa   1860

gatcgccaaa caaaagatca tgtactatca ttacttattc accctattcc tcttactcaa   1920

tag                                                                 1923
```

<210> SEQ ID NO 33
<211> LENGTH: 1533
<212> TYPE: DNA
<213> ORGANISM: Cannabis sp.
<220> FEATURE:
<223> OTHER INFORMATION: (E)-beta-ocimene/(E,E)-alpha-farnesene synthase
<220> FEATURE:
<221> NAME/KEY: misc_feature
<222> LOCATION: (0)...(0)
<223> OTHER INFORMATION: EST marker PE2EUKC3385636, library_id:2654

<400> SEQUENCE: 33

```
atgctagagc tgattaacac catcagaaaa ctaagcttga catatcattt cgaagacgaa     60

gtcaagaaag ttcttgacaa aatatcatct tccaattact actacaataa taaagacatt    120
```

```
aaagatcccc gcctcgtagg agacgatctc tatctcgctg cattatattt caggctcctt     180

aggcttcatg gatatcaagt ttcacaagac atatttgttg gctacaatag tgtggattac     240

aaaaaaggtg gtgggacaca taatatcaca tcaacagagg tgaaagtgat gatagagctt     300

ttagaggcct cacatgtagc ttttgagtgt gaggacactc taactgaggc taaagctttg     360

atggaagaaa acctcaaaat tgcctttcct gacaactgca acaaatatat tcccaaacat     420

gaggtggttc atgctttgga acttccatct cattggaggg ttcagtggtt tgatgtaaaa     480

tggcaaatag aagcttatcg tcaacatggt gacccggata ccaacactac aactactact     540

agtctcttgg ttgatttagc caaattaaac tttaacataa ttcaagccac acttcaaaaa     600

gatcttaggg agttgtccag ttggtggaag aatgtgggcc tttcagagaa gttggaattt     660

gcgagagata ggttggtcga gagcttcatg tgtactgtgg gactggcttt tcagcctgaa     720

tacaaaagtc tgagaaaatg tcttaccaaa gtggtcaatt tcatactcat tgttgatgat     780

gtttatgatg tttatggctc attggaagag ctgagacact tcaccaatgc cgttaatagg     840

tgggatgtcc gggaaactga ggaacttcca gattgcatga agatttgttt ccaagcactc     900

taccatacta catgtgaaat tgctagtgaa attgagacta agaatggttg caaattagtt     960

ttacctaatc taaagggagc gtggacagac ttttgtaaat cactattaat ggaggcagaa    1020

tggtaccaca aggggtacat cccatccctt gaggagtatt tgagcaatgc atggatttca    1080

tcttcggggc ctcttcttct tcttcattca tatcttgcta tgccaaatca gactaatacg    1140

gcctcttctc ttgacataag caaagatctt gtctacaaca tttctctcat cattcgacta    1200

tgcaacgatt taggaacttc agcggctgaa caggaaagag gagatgctgc atcttctatc    1260

gtatgttata tgcaagaaac gaagagtagt gaagaggagg cccgaaagca tatccgagaa    1320

atgattagaa aaacatggaa gaagatcaac aagaaatgct ttagtacttg cggcagtagt    1380

tcactatcat tatcatttat agatattgcc cttaacactg ctcgagtggc acatagcctc    1440

taccaatctg gagatgcctt cagtgctcaa catacagact ataagactca tattctctcc    1500

ttactcgttc accctctcat tcccaataag taa                                 1533
```

<210> SEQ ID NO 34
<211> LENGTH: 2145
<212> TYPE: DNA
<213> ORGANISM: Cannabis sp.
<220> FEATURE:
<223> OTHER INFORMATION: Copalyl diphosphate synthase 1
<220> FEATURE:
<221> NAME/KEY: misc_feature
<222> LOCATION: (0)...(0)
<223> OTHER INFORMATION: EST marker PE2EUKC3398153, library_id:2654

<400> SEQUENCE: 34

```
atgttggaga gtatggatga gggagagata agcatttcag cgtacgacac agcatgggta      60

gcccttgtgg aagatattca tgggagtggc ttacctcaat tcccatcgag tctccaatgg     120

atcgccacac atcagctctc cgacggttct tggggcgatg ctgacatttt ctccgcacac     180

gatcgcctca tcaacacttt ggcttgtgtt gttgctttga aatcttggaa cctttatccc     240

gaaaaatgtc aaaaaggtat ggccttttc aatgcaaata taagtaagct tgagagggag      300

aatccggaac acatgcctat tggtttcgaa gtggctttcc cttctttact tgaaatagct     360

cgaaaattaa accttgaagt gcctgaggat tctcctgtgt taaaagtcat atatgctagg     420

agagatttca agctcacaag gattccgagg gacataatgc acacagtgcc cacgacgcta     480

ctccatagct tggaaggaat ggtaggtctg gactgggaaa agcttttgaa actgcagtcc     540
```

-continued

```
caagatgggt cattcttgtt ctcaccatcc tcaactgctt ttgcactcat ggagaccaaa    600

gaccgaaatt gcttgcaata tttaactaaa gcggtccaaa ggttcaacgg gggtgtccca    660

aatgtttacc cggttgactt gttcgagcac ctttgggttg cggatcggtt gcagcgcttg    720

ggaatatcaa gattctttga gccacaaatt gaggaatgta tcgattatgt attcagaaat    780

tggactgaga aaggaattgg ctgggcaaga aattccaagg ttgaagatat tgacgataca    840

gcaatgggtt tcagactact aagattgcat ggtcacaaag tttctgccga tgtgttccaa    900

cactttaaga aaggtgacga ttttttctgc tttcggggcc agtcaactca agcagtgact    960

gggatgtata acctttttag agcttctcag ttggttttcc ctggagaaaa aattcttgaa   1020

gatgccatgg aattctcatc gaaatttctt agaaaaaaac aggcgtccaa tgaattgcta   1080

gataaatgga tcataacaaa ggacttacct ggtgaggtgg gtttcgcatt ggaggttcca   1140

tggaatgcaa acttacctcg agtagagacc agattctaca ttgaacagta tggtggacaa   1200

aatgatgttt ggattggcaa gacactctac agaatgcgaa aagttaacaa tgacgaatat   1260

ctagagttag caaaacttga ttacaacatt tgccaagctt tgcattcgat tgagtggcac   1320

aatttgctaa aatggtaccg agattgtaag ttggaaaatt atggagtgag cagaaggaac   1380

ctcctcttgg cctatttctt tgctgcggcc agtattttcg aaccggagag ggccgatgag   1440

cggcttgcat gggctaaaac ggcagcactg atgcaggcca tccaatctca tttcgatgac   1500

cagaaagctt cttcggagca tcgtatagct tttgtctctg cttttaaaag gagttgtaac   1560

atgccatcgt atttgattac aagggtgtcg aacataagtg atacagatca tggccttctt   1620

agaacgttga tgacgactct cagccacctc tctttggaca caatgatgct gtatggtcgg   1680

gacatcaccc accatttacg tcaagcttgg gaaaagtggc tggtgaagtg gcaagagggt   1740

ggtgatggac attacgaaga agaagcagaa ttattgatcc aaacaataaa ccttagctca   1800

ggccgtacac ttgtgaaggc cctcttgctg tcaaatcctc actatgaaaa actcttcagt   1860

accacaaaca aagtttgctg caaaattcgt cactttcaaa gacaaaggca tagggccaag   1920

gcaaatcaaa atggagaatt taacagaaac atcttaacac cagaaataga gtcagatatg   1980

caagaggttg tgcaattggt gctacaaaaa tcttcagatg acatcaacac aaaaattaag   2040

cagacatttc tactggtggc caagtctttt tattatgctg cctactgtga ttctaagacc   2100

atcaatttcc acattggcaa agtaatattt gagactgtgg actga                   2145
```